(12) United States Patent
Zhang et al.

(10) Patent No.: US 8,321,002 B2
(45) Date of Patent: Nov. 27, 2012

(54) ARRHYTHMIA DISCRIMINATION USING ECG'S SENSED FROM MULTIPLE IMPLANTED ELECTRODES

(75) Inventors: Yi Zhang, Plymouth, MN (US); Carlos A. Ricci, Apple Valley, MN (US); Jeffrey E. Stahmann, Ramsey, MN (US); Aaron McCabe, Minneapolis, MN (US); Scott Meyer, Lakeville, MN (US); Yinghong Yu, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 13/027,608

(22) Filed: Feb. 15, 2011

(65) Prior Publication Data

US 2011/0137192 A1    Jun. 9, 2011

Related U.S. Application Data

(63) Continuation of application No. 11/125,020, filed on May 9, 2005, now Pat. No. 7,917,196.

(51) Int. Cl.
  *A61B 5/0464* (2006.01)
(52) U.S. Cl. ..................................................... 600/512
(58) Field of Classification Search .................... 600/512
  See application file for complete search history.

(56) References Cited

U.S. PATENT DOCUMENTS

| | | |
|---|---|---|
| 3,920,005 A | 11/1975 | Gombrich et al. |
| 4,388,927 A | 6/1983 | Schober |
| 4,550,221 A | 10/1985 | Mabusth |
| 4,686,332 A | 8/1987 | Greanias et al. |
| 4,953,551 A | 9/1990 | Mehra et al. |
| 5,133,353 A | 7/1992 | Hauser |
| 5,170,784 A | 12/1992 | Ramon et al. |
| 5,179,945 A | 1/1993 | Van Hofwegen et al. |
| 5,209,229 A | 5/1993 | Gilli |
| 5,222,493 A | 6/1993 | Sholder |
| 5,231,990 A | 8/1993 | Gauglitz |

(Continued)

FOREIGN PATENT DOCUMENTS

EP    0468720    1/1992

(Continued)

OTHER PUBLICATIONS

File History for U.S. Appl. No. 10/955,397 as retrieved from U.S. Patent and Trademark Office PAIR System on Feb. 13, 2011, 473 pages.

(Continued)

*Primary Examiner* — Tammie K Heller
(74) *Attorney, Agent, or Firm* — Hollingsworth Davis, LLC

(57) ABSTRACT

Cardiac monitoring and/or stimulation methods and systems provide for monitoring, diagnosing, defibrillation and pacing therapies, or a combination of these capabilities, including cardiac systems incorporating or cooperating with neuro-stimulating devices, drug pumps, or other therapies. Embodiments of the present invention relate generally to implantable medical devices employing automated cardiac activation sequence monitoring and/or tracking for arrhythmia discrimination. Embodiments of the invention are directed to devices and methods involving sensing a plurality of composite cardiac signals using a plurality of implantable electrodes. A source separation is performed using the sensed plurality of composite cardiac signals and the separation produces one or more cardiac signal vectors associated with one or more cardiac activation sequences that is indicative of ischemia. A change of the one or more cardiac signal vectors is detected using the one or more cardiac signal vectors. Cardiac arrhythmias are discriminated using the one or more cardiac signal vectors.

18 Claims, 26 Drawing Sheets

U.S. PATENT DOCUMENTS

| | | | |
|---|---|---|---|
| 5,261,400 A | 11/1993 | Bardy | |
| 5,271,411 A | 12/1993 | Ripley et al. | |
| 5,292,338 A | 3/1994 | Bardy | |
| 5,300,106 A | 4/1994 | Dahl et al. | |
| 5,312,445 A | 5/1994 | Nappholz et al. | |
| 5,314,430 A | 5/1994 | Bardy | |
| 5,314,459 A | 5/1994 | Swanson et al. | |
| 5,318,597 A | 6/1994 | Hauck et al. | |
| 5,331,966 A | 7/1994 | Bennett et al. | |
| 5,331,996 A | 7/1994 | Ziehm | |
| 5,333,095 A | 7/1994 | Stevenson et al. | |
| 5,350,410 A | 9/1994 | Kleks et al. | |
| 5,372,606 A | 12/1994 | Lang et al. | |
| 5,376,106 A | 12/1994 | Stahmann et al. | |
| 5,411,525 A | 5/1995 | Swanson et al. | |
| 5,411,533 A | 5/1995 | Dubreuil et al. | |
| 5,411,539 A | 5/1995 | Neisz | |
| 5,431,693 A | 7/1995 | Schroeppel | |
| 5,439,482 A | 8/1995 | Adams et al. | |
| 5,441,518 A | 8/1995 | Adams et al. | |
| 5,443,485 A | 8/1995 | Housworth et al. | |
| 5,468,254 A | 11/1995 | Hahn et al. | |
| 5,520,191 A | 5/1996 | Karlsson et al. | |
| 5,531,779 A | 7/1996 | Dahl et al. | |
| 5,605,158 A | 2/1997 | Snell | |
| 5,620,466 A | 4/1997 | Haefner et al. | |
| 5,626,620 A | 5/1997 | Kieval et al. | |
| 5,634,938 A | 6/1997 | Swanson et al. | |
| 5,641,326 A | 6/1997 | Adams | |
| 5,650,759 A | 7/1997 | Hittman et al. | |
| 5,662,688 A | 9/1997 | Haefner et al. | |
| 5,674,254 A | 10/1997 | van Krieken | |
| 5,683,431 A | 11/1997 | Wang | |
| 5,683,434 A | 11/1997 | Archer | |
| 5,697,953 A | 12/1997 | Kroll et al. | |
| 5,697,959 A | 12/1997 | Poore | |
| 5,704,365 A | 1/1998 | Albrecht et al. | |
| 5,724,984 A | 3/1998 | Arnold et al. | |
| 5,735,882 A | 4/1998 | Rottenberg et al. | |
| 5,803,084 A | 9/1998 | Olson | |
| 5,827,326 A | 10/1998 | Kroll et al. | |
| 5,844,506 A | 12/1998 | Binstead | |
| 5,861,013 A | 1/1999 | Peck et al. | |
| 5,871,512 A | 2/1999 | Hemming et al. | |
| 5,873,898 A | 2/1999 | Hemming et al. | |
| 5,895,414 A | 4/1999 | Sanchez-Zambrano | |
| 5,957,956 A | 9/1999 | Kroll et al. | |
| 5,983,138 A | 11/1999 | Kramer | |
| 5,987,352 A | 11/1999 | Klein et al. | |
| 6,049,730 A | 4/2000 | Kristbjarmarson | |
| 6,084,253 A | 7/2000 | Turner, Jr. | |
| 6,101,416 A | 8/2000 | Sloman | |
| 6,115,628 A | 9/2000 | Stadler et al. | |
| 6,128,535 A | 10/2000 | Maarse | |
| 6,134,473 A | 10/2000 | Hemming et al. | |
| 6,144,880 A | 11/2000 | Ding | |
| 6,147,680 A | 11/2000 | Tareev | |
| 6,148,230 A | 11/2000 | KenKnight | |
| 6,163,724 A | 12/2000 | Hemming et al. | |
| 6,169,921 B1 | 1/2001 | KenKnight et al. | |
| 6,175,766 B1 | 1/2001 | Bornzin et al. | |
| 6,192,273 B1 * | 2/2001 | Igel et al. | 607/14 |
| 6,192,275 B1 | 2/2001 | Zhu et al. | |
| 6,227,072 B1 | 5/2001 | Ritchey et al. | |
| 6,253,102 B1 | 6/2001 | Hsu et al. | |
| 6,266,554 B1 | 7/2001 | Hsu et al. | |
| 6,267,778 B1 | 7/2001 | Cohen | |
| 6,275,731 B1 | 8/2001 | Zhu et al. | |
| 6,280,462 B1 | 8/2001 | Hauser et al. | |
| 6,282,440 B1 | 8/2001 | Brodnick et al. | |
| 6,301,503 B1 | 10/2001 | Hsu et al. | |
| 6,324,421 B1 | 11/2001 | Stadler et al. | |
| 6,324,427 B1 | 11/2001 | Florio | |
| 6,351,673 B1 | 2/2002 | Ding et al. | |
| 6,360,127 B1 | 3/2002 | Ding et al. | |
| 6,371,922 B1 | 4/2002 | Baumann et al. | |
| 6,409,675 B1 | 6/2002 | Turcott | |
| 6,415,174 B1 | 7/2002 | Bebehani et al. | |
| 6,418,340 B1 | 7/2002 | Conley et al. | |
| 6,424,234 B1 | 7/2002 | Stevenson | |
| 6,438,409 B1 | 8/2002 | Malik et al. | |
| 6,449,503 B1 | 9/2002 | Hsu | |
| 6,456,481 B1 | 9/2002 | Stevenson | |
| 6,456,880 B1 | 9/2002 | Park et al. | |
| 6,491,639 B1 | 12/2002 | Turcott | |
| 6,496,715 B1 | 12/2002 | Lee et al. | |
| 6,505,067 B1 | 1/2003 | Lee et al. | |
| 6,505,071 B1 | 1/2003 | Zhu et al. | |
| 6,512,940 B1 | 1/2003 | Brabec et al. | |
| 6,512,953 B2 | 1/2003 | Florio et al. | |
| 6,522,915 B1 | 2/2003 | Ceballos et al. | |
| 6,564,106 B2 | 5/2003 | Guck et al. | |
| 6,567,701 B2 | 5/2003 | Vonk | |
| 6,607,509 B2 | 8/2003 | Bobroff et al. | |
| 6,609,027 B2 | 8/2003 | Kroll et al. | |
| 6,615,082 B1 | 9/2003 | Mandell | |
| 6,615,083 B2 | 9/2003 | Kupper | |
| 6,622,046 B2 | 9/2003 | Fraley et al. | |
| 6,625,490 B1 | 9/2003 | McClure et al. | |
| 6,631,290 B1 | 10/2003 | Guck et al. | |
| 6,690,967 B2 | 2/2004 | Meij | |
| 6,701,170 B2 | 3/2004 | Stetson | |
| 6,708,058 B2 | 3/2004 | Kim et al. | |
| 6,725,085 B2 | 4/2004 | Schwartzman et al. | |
| 6,754,523 B2 | 6/2004 | Toole | |
| 6,754,528 B2 | 6/2004 | Bardy et al. | |
| 6,760,615 B2 | 7/2004 | Ferek-Petric | |
| 6,766,190 B2 | 7/2004 | Ferek-Petric | |
| 6,768,923 B2 | 7/2004 | Ding et al. | |
| 6,778,860 B2 | 8/2004 | Ostroff et al. | |
| 6,788,974 B2 | 9/2004 | Bardy et al. | |
| 6,834,204 B2 | 12/2004 | Ostroff et al. | |
| 6,856,835 B2 | 2/2005 | Bardy et al. | |
| 6,865,417 B2 | 3/2005 | Rissmann et al. | |
| 6,866,044 B2 | 3/2005 | Bardy et al. | |
| 6,871,096 B2 | 3/2005 | Hill | |
| 6,884,218 B2 | 4/2005 | Olson et al. | |
| 6,888,538 B2 | 5/2005 | Ely et al. | |
| 6,889,079 B2 | 5/2005 | Bocek et al. | |
| 6,904,315 B2 | 6/2005 | Panken et al. | |
| 6,925,324 B2 | 8/2005 | Shusterman | |
| 6,925,330 B2 | 8/2005 | Kleine | |
| 6,927,721 B2 | 8/2005 | Ostroff | |
| 6,937,907 B2 | 8/2005 | Bardy et al. | |
| 6,944,579 B2 | 9/2005 | Shimizu | |
| 6,950,702 B2 | 9/2005 | Sweeney | |
| 6,950,705 B2 | 9/2005 | Bardy et al. | |
| 6,952,608 B2 | 10/2005 | Ostroff | |
| 6,952,610 B2 | 10/2005 | Ostroff | |
| 6,954,670 B2 | 10/2005 | Ostroff | |
| 6,961,619 B2 | 11/2005 | Casey | |
| 6,973,350 B1 | 12/2005 | Levine et al. | |
| 6,983,264 B2 | 1/2006 | Shimizu | |
| 6,988,003 B2 | 1/2006 | Bardy et al. | |
| 6,993,379 B1 | 1/2006 | Kroll | |
| 6,993,389 B2 | 1/2006 | Ding | |
| 7,027,861 B2 | 4/2006 | Thompson | |
| 7,027,868 B2 | 4/2006 | Rueter et al. | |
| 7,039,459 B2 | 5/2006 | Bardy | |
| 7,039,465 B2 | 5/2006 | Bardy | |
| 7,043,299 B2 | 5/2006 | Erlinger | |
| 7,050,851 B2 | 5/2006 | Plombon et al. | |
| 7,065,400 B2 | 6/2006 | Schechter | |
| 7,065,407 B2 | 6/2006 | Bardy | |
| 7,065,410 B2 | 6/2006 | Bardy et al. | |
| 7,069,080 B2 | 6/2006 | Bardy | |
| 7,076,296 B2 | 7/2006 | Rissmann et al. | |
| 7,079,988 B2 | 7/2006 | Albera | |
| 7,085,599 B2 | 8/2006 | Kim et al. | |
| 7,090,682 B2 | 8/2006 | Sanders et al. | |
| 7,092,754 B2 | 8/2006 | Bardy et al. | |
| 7,096,064 B2 | 8/2006 | Deno et al. | |
| 7,107,093 B2 | 9/2006 | Burnes | |
| 7,110,817 B2 | 9/2006 | Yu et al. | |
| 7,120,495 B2 | 10/2006 | Bardy et al. | |
| 7,123,960 B2 | 10/2006 | Ding | |
| 7,129,935 B2 | 10/2006 | Mackey | |

| | | | |
|---|---|---|---|
| 7,144,586 B2 | 12/2006 | Levy et al. |
| 7,146,206 B2 | 12/2006 | Glass et al. |
| 7,146,212 B2 | 12/2006 | Bardy et al. |
| 7,149,575 B2 | 12/2006 | Ostroff et al. |
| 7,158,830 B2 | 1/2007 | Yu |
| 7,181,285 B2 | 2/2007 | Lindh |
| 7,184,835 B2 | 2/2007 | Kramer et al. |
| 7,194,302 B2 | 3/2007 | Bardy et al. |
| 7,194,309 B2 | 3/2007 | Ostroff et al. |
| 7,203,540 B2 | 4/2007 | Ding et al. |
| 7,228,173 B2 | 6/2007 | Cazares |
| 7,228,174 B2 | 6/2007 | Burnes |
| 7,236,819 B2 | 6/2007 | Brockway |
| 7,242,978 B2 | 7/2007 | Cao |
| 7,245,962 B2 | 7/2007 | Ciaccio et al. |
| 7,248,925 B2 | 7/2007 | Bruhns et al. |
| 7,263,399 B2 | 8/2007 | Carlson |
| 7,277,754 B2 | 10/2007 | McCabe et al. |
| 7,299,086 B2 | 11/2007 | McCabe et al. |
| 7,310,554 B2 | 12/2007 | Kramer |
| 7,359,749 B2 | 4/2008 | Quenet et al. |
| 7,457,664 B2 | 11/2008 | Zhang et al. |
| 7,509,170 B2 | 3/2009 | Zhang et al. |
| 7,558,628 B2 | 7/2009 | Yonce et al. |
| 7,580,741 B2 | 8/2009 | Cazares et al. |
| 7,653,431 B2 | 1/2010 | Cazares et al. |
| 2002/0035377 A1 | 3/2002 | Bardy et al. |
| 2002/0035378 A1 | 3/2002 | Bardy et al. |
| 2002/0035379 A1 | 3/2002 | Bardy et al. |
| 2002/0035381 A1 | 3/2002 | Bardy et al. |
| 2002/0082658 A1 | 6/2002 | Heinrich et al. |
| 2002/0095184 A1 | 7/2002 | Bardy et al. |
| 2002/0095188 A1 | 7/2002 | Mower |
| 2002/0107544 A1 | 8/2002 | Ostroff et al. |
| 2002/0107545 A1 | 8/2002 | Rissmann et al. |
| 2002/0138111 A1 | 9/2002 | Greenhut et al. |
| 2002/0183798 A1 | 12/2002 | Vonk |
| 2003/0023175 A1 | 1/2003 | Arzbaecher et al. |
| 2003/0050671 A1 | 3/2003 | Bradley |
| 2003/0083710 A1 | 5/2003 | Ternes et al. |
| 2003/0083711 A1 | 5/2003 | Yonce et al. |
| 2003/0100925 A1 | 5/2003 | Pape et al. |
| 2003/0204214 A1 | 10/2003 | Ferek-Patric |
| 2003/0212436 A1 | 11/2003 | Brown |
| 2004/0064159 A1 | 4/2004 | Hoijer et al. |
| 2004/0127950 A1 | 7/2004 | Kim et al. |
| 2004/0158293 A1 | 8/2004 | Yonce et al. |
| 2004/0171959 A1 | 9/2004 | Stadler et al. |
| 2004/0215240 A1 | 10/2004 | Lovett et al. |
| 2004/0243014 A1 | 12/2004 | Lee et al. |
| 2005/0010120 A1 | 1/2005 | Jung |
| 2005/0038478 A1 | 2/2005 | Klepfer et al. |
| 2005/0065587 A1 | 3/2005 | Gryzwa |
| 2005/0107839 A1 | 5/2005 | Sanders |
| 2005/0288600 A1 | 12/2005 | Zhang et al. |
| 2006/0069322 A1 | 3/2006 | Zhang et al. |
| 2006/0074331 A1 | 4/2006 | Kim et al. |
| 2006/0111747 A1 | 5/2006 | Cazares et al. |
| 2006/0116593 A1 | 6/2006 | Zhang et al. |
| 2006/0253043 A1 | 11/2006 | Zhang et al. |
| 2006/0253044 A1 | 11/2006 | Zhang et al. |
| 2006/0259086 A1 | 11/2006 | Yu et al. |
| 2007/0027488 A1 | 2/2007 | Kaiser et al. |
| 2007/0049974 A1 | 3/2007 | Li et al. |
| 2007/0191901 A1 | 8/2007 | Schecter |
| 2008/0004665 A1 | 1/2008 | McCabe et al. |
| 2008/0009909 A1 | 1/2008 | Sathaye et al. |
| 2008/0045851 A1 | 2/2008 | Cazares et al. |
| 2008/0097537 A1 | 4/2008 | Duann et al. |
| 2009/0076557 A1 | 3/2009 | Zhang et al. |
| 2009/0198301 A1 | 8/2009 | Zhang et al. |
| 2010/0298729 A1 | 11/2010 | Zhang et al. |

FOREIGN PATENT DOCUMENTS

| | | |
|---|---|---|
| EP | 0560569 | 9/1993 |
| EP | 1038498 | 9/2000 |
| EP | 1350539 | 10/2003 |
| EP | 1629863 | 3/2006 |
| WO | WO9217240 | 10/1992 |
| WO | WO9220402 | 11/1992 |
| WO | WO0240097 | 5/2002 |
| WO | WO0247761 | 6/2002 |
| WO | WO03003905 | 1/2003 |
| WO | WO03028550 | 4/2003 |
| WO | WO2005058412 | 6/2005 |
| WO | WO2005089865 | 9/2005 |
| WO | WO2006065707 | 6/2006 |
| WO | WO2008005270 | 1/2008 |

OTHER PUBLICATIONS

File History for U.S. Appl. No. 10/876,008 as retrieved from U.S. Patent and Trademark Office PAIR System on Feb. 13, 2011, 518 pages.

File History for U.S. Appl. No. 11/124,972 as retrieved from U.S. Patent and Trademark Office PAIR System on Feb. 13, 2011, 240 pages.

File History for U.S. Appl. No. 11/125,068 as retrieved from U.S. Patent and Trademark Office PAIR System on Feb. 13, 2011, 336 pages.

File History for U.S. Appl. No. 12/276,070 as retrieved from U.S. Patent and Trademark Office PAIR System on Feb. 13, 2011, 304 pages.

File History for U.S. Appl. No. 11/079,744 as retrieved from U.S. Patent and Trademark Office PAIR System on Feb. 13, 2011, 371 pages.

File History for U.S. Appl. No. 11/124,950 as retrieved from U.S. Patent and Trademark Office PAIR System on Feb. 13, 2011, 386 pages.

File History for U.S. Appl. No. 11/125,020 as retrieved from U.S. Patent and Trademark Office PAIR System on Feb. 13, 2011, 454 pages.

International Search Report and Written Opinion dated Nov. 2, 2005 from PCT Application No. PCT/US05/22575, 12 pages.

International Preliminary Report on Patentability dated Jan. 11, 2007 from PCT Application No. PCT/US05/22575, 7 pages.

International Search Report and Written Opinion dated Feb. 27, 2006 from PCT Application No. PCT/US05/35638, 10 pages.

International Preliminary Report on Patentability dated Apr. 3, 2007 from PCT Application No. PCT/US05/35638, 6 pages.

Acar et al., "SVD-based on-line exercise ECG signal orthogonalization", IEEE Transactions on Biomedical Engineering, vol. 46, No. 3, Mar. 1999. Abstract only.

Belouchrani et al., Blind Source Separation Based on Time-Frequency Signal Representations, IEEE Transactions on Signal Processing, vol. 46, No. 11, pp. 2888-2897 (Nov. 1998).

Cohen et al. Capture Management Efficacy in children and young adults with endocardial and unipolar epicardial systems. Europace, vol. 6, pp. 248-255, 2004.

Pierre Comon, Independent component analysis, A new concept?, Signal Processing, vol. 36, No. 3, pp. 287-314, (Apr. 1994).

Gallois, et al., Multi-Channel Analysis of the EEG Signals and Statistic Particularities for Epileptic Seizure Forecast, Second Joint EMBS/BMES Conference, pp. 208-215 (Oct. 23-26, 2002).

Gradaus et al., Nonthoracotomy Implantable Cardioverter Defibrillator Placement in Children: Use of a Subcutaneous Array Leads and Abdominally Placed Implantable Cardioverter Defibrillators in Children, J. of Cardiovascular Electrophysiology, vol. 12, No. 3, pp. 356-360 (Mar. 2001).

Hartz et al., New Approach to Defibrillator Insertion, J. Thoracic Cardiovascular Surgery, vol. 97, pp. 920-922 (1989).

A. Hyvärinen and E. Oja, Independent Component Analysis: A Tutorial, Helsinski Univ. of Technology, Apr. 1999.

Kolettis et al., Submammary Implantation of a Cardioverter-Defibrillator with a Nonthoractomy Lead System, Am. Heart J., vol. 126, pp. 1222-1223 (Nov. 1993).

Krahn et al. Recurrent syncope. Experience with an implantable loop record. Cardiol. Clin., vol. 15(2), May 1997, pp. 316-326.

Leng et al., Lead Configuration for Defibrillator Implantation in a Patient with Congenital Heart Disease and a Mechanical Prosthetic Tricuspid Valve, PACE, vol. 24, pp. 1291-1292, Aug. 2001.

Park & Pollock, Use of an Implantable Cardioverter Defibrillator in an Eight-Month-Old Infant with Ventricular Fibrillation Arising from a Myocardial Fibroma, PACE, vol. 22, No. 1, pp. 138-139 Jan. 1999.

Rieta, et al., Atrial Activity Extraction Based on Blind Source Separation as an Alternative to QRST Cancellation for Atrial Fibrillation Analysis, Computers in Cardiology, vol. 27, pp. 69-72 (2000).

Schuder et al., Experimental Ventricular Defibrillation with an Automatic and Completely Implanted System, Trans. Am. Soc. Artif. Int. Organs, vol. 16, pp. 207-212 (1970).

Schuder et al., Transthoracic Ventricular Defibrillation in the Dog with Truncated and Untruncated Exponential Stimuli, IEEE Trans. On Bio-Medical Engin., vol. BME-18, No. 6, pp. 410-415 Nov. 1971.

Schuder et al., Ventricular Defibrillation in the Dog Using Implanted and Partially Implanted Electrode Systems, Am. J. of Cardiology, vol. 33, pp. 243-247 Feb. 1974.

Smits et al., Defibrillation Threshold (DFT) Model of a Fully Subcutaneous ICD System, Europace Supplements, vol. 2, Jun. 2001 at col. 778, p. B83.

Splett et al., Determination of Pacing Capture in Implantable Defibrillators: Benefit of Evoked Response Detection Using RV Coil to Can Vector, PACE, vol. 23, pp. 1645-1650, Nov. 2000.

Stirbis et al., Optimizing the Shape of Implanted Artificial Pacemakers, Kaunas Medical Institute. Translated from Meditsinskaya Tekhnika, No. 6, pp. 25-27 (1986). Abstract only.

Wilkoff BL, et al., Preventing Shocks after ICD Implantation: Can a Strategy of Standardized ICD Programming Match Physician Tailored?, Late Breaking Trials, HRS, 2005.

Zarzoso et al., Noninvasive Fetal Electrocardiogram Extraction: Blind Separation Versus Adaptive Noise Cancellation, IEEE Transactions on Biomedical Engineering, vol. 48, No. 1, pp. 12-18, Jan. 2001.

Zarzoso et al., Blind Separation of Independent Sources for Virtually Any Source Probability Density Function, IEEE Transactions on Signal Processing, vol. 47, No. 9, pp. 2419-2432 (Sep. 1999).

Office Action dated Apr. 2, 2012 from U.S. Appl. No. 13/027,612, 13 pages.

File History for U.S. Appl. No. 12/409,348 as retrieved from the U.S. Patent and Trademark Office PAIR System on May 24, 2012, 334 pages.

File History for U.S. Appl. No. 12/847,657.

File History for U.S. Appl. No. 13/027,612.

Office Action dated Sep. 17, 2012 for U.S. Appl. No. 13/027,612, 8 pages.

* cited by examiner

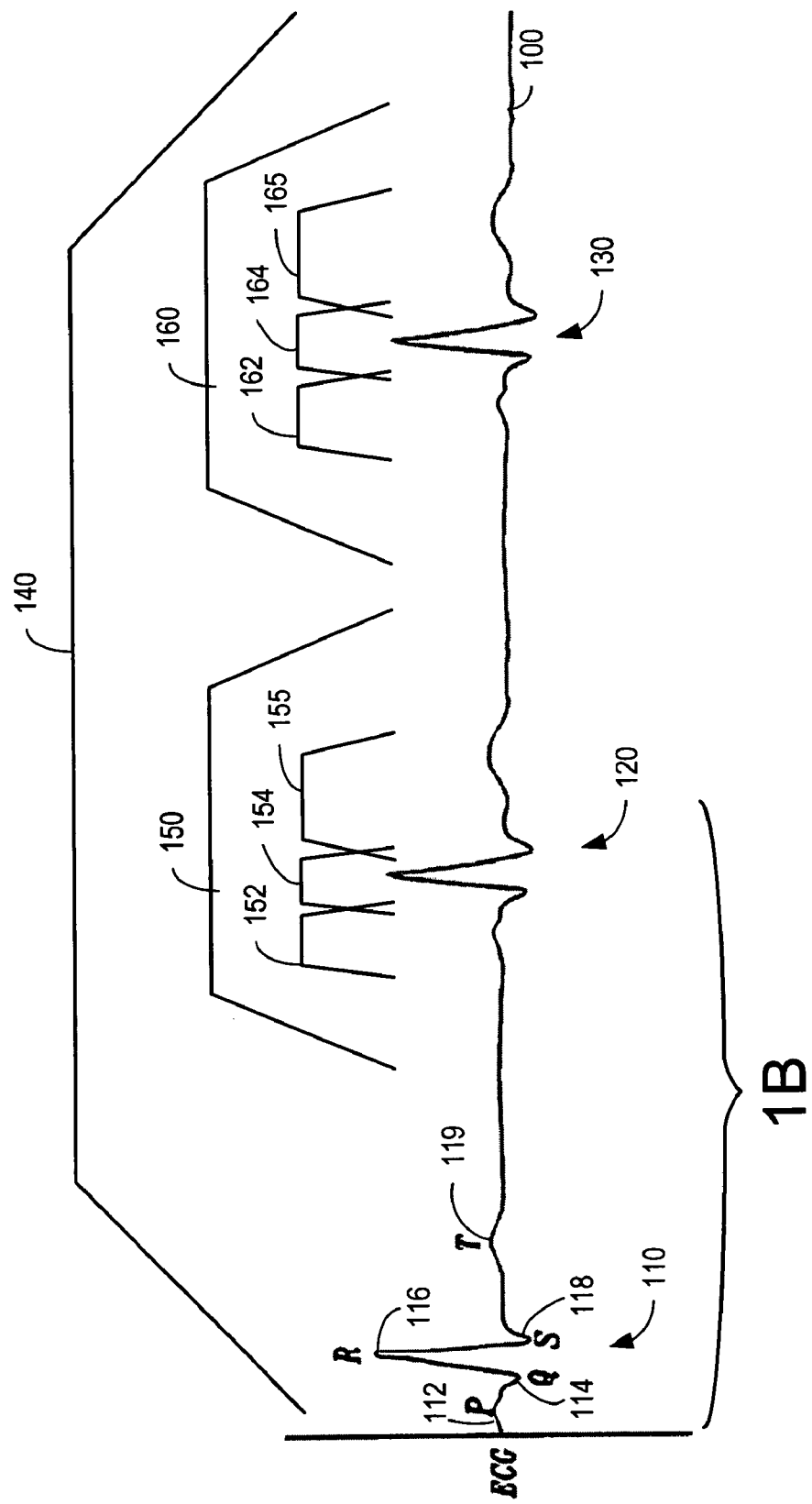

ARRHYTHMIA DISCRIMINATION USING ECG'S SENSED FROM MULTIPLE IMPLANTED ELECTRODES

RELATED APPLICATIONS

This application is a continuation of U.S. patent Publication Ser. No. 11/125,020, filed on May 9, 2005, now U.S. Pat. No. 7,917,196, to which Applicant claims priority under 35 U.S.C. §120, and which is incorporated herein by reference in its entirety.

FIELD OF THE INVENTION

The present invention relates generally to implantable medical devices employing cardiac signal separation and, more particularly, to cardiac sensing and/or stimulation devices employing cardiac activation sequence monitoring and tracking for arrhythmia discrimination.

BACKGROUND

The healthy heart produces regular, synchronized contractions. Rhythmic contractions of the heart are normally initiated by the sinoatrial (SA) node, which is a group of specialized cells located in the upper right atrium. The SA node is the normal pacemaker of the heart, typically initiating 60-100 heartbeats per minute. When the SA node is pacing the heart normally, the heart is said to be in normal sinus rhythm.

If the heart's electrical activity becomes uncoordinated or irregular, the heart is denoted to be arrhythmic. Cardiac arrhythmia impairs cardiac efficiency and may be a potential life-threatening event. Cardiac arrhythmias have a number of etiological sources, including tissue damage due to myocardial infarction, infection, or degradation of the heart's ability to generate or synchronize the electrical impulses that coordinate contractions.

Bradycardia occurs when the heart rhythm is too slow. This condition may be caused, for example, by impaired function of the SA node, denoted sick sinus syndrome, or by delayed propagation or blockage of the electrical impulse between the atria and ventricles. Bradycardia produces a heart rate that is too slow to maintain adequate circulation.

When the heart rate is too rapid, the condition is denoted tachycardia. Tachycardia may have its origin in either the atria or the ventricles. Tachycardias occurring in the atria of the heart, for example, include atrial fibrillation and atrial flutter. Both conditions are characterized by rapid contractions of the atria. Besides being hemodynamically inefficient, the rapid contractions of the atria may also adversely affect the ventricular rate.

Ventricular tachycardia occurs, for example, when electrical activity arises in the ventricular myocardium at a rate more rapid than the normal sinus rhythm. Ventricular tachycardia may quickly degenerate into ventricular fibrillation. Ventricular fibrillation is a condition denoted by extremely rapid, uncoordinated electrical activity within the ventricular tissue. The rapid and erratic excitation of the ventricular tissue prevents synchronized contractions and impairs the heart's ability to effectively pump blood to the body, which is a fatal condition unless the heart is returned to sinus rhythm within a few minutes.

Implantable cardiac rhythm management systems have been used as an effective treatment for patients with serious arrhythmias, as well as for patients with conditions such as heart failure. These systems typically include one or more leads and circuitry to sense signals from one or more interior and/or exterior surfaces of the heart. Such systems also include circuitry for generating electrical pulses that are applied to cardiac tissue at one or more interior and/or exterior surfaces of the heart. For example, leads extending into the patient's heart are connected to electrodes that contact the myocardium for sensing the heart's electrical signals and for delivering pulses to the heart in accordance with various therapies for treating arrhythmias.

Typical implantable cardioverter/defibrillators include one or more endocardial leads to which at least one defibrillation electrode is connected. Such implantable cardioverter/defibrillators are capable of delivering high-energy shocks to the heart, interrupting the ventricular tachyarrhythmia or ventricular fibrillation, and allowing the heart to resume normal sinus rhythm. Implantable cardioverter/defibrillators may also include pacing functionality.

SUMMARY

The present invention is directed to cardiac monitoring and/or stimulation methods and systems that provide monitoring, diagnosing, defibrillation therapies, pacing therapies, or a combination of these capabilities, including cardiac systems incorporating or working in cooperation with neuro-stimulating devices, drug pumps, or other therapies. Embodiments of the present invention relate generally to implantable medical devices employing cardiac signal separation and, more particularly, to cardiac monitoring and/or stimulation devices employing automated cardiac activation sequence monitoring and/or tracking for arrhythmia discrimination.

Embodiments of the invention are directed to devices and methods involving sensing a plurality of composite cardiac signals using a plurality of implantable electrodes. A source separation is performed using the sensed plurality of composite cardiac signals and the separation produces one or more cardiac signal vectors associated with one or more cardiac activation sequences that is indicative of arrhythmia. A change of the one or more cardiac signal vectors is detected using the one or more cardiac signal vectors. Cardiac arrhythmias are discriminated using the one or more cardiac signal vectors.

Specific embodiments are directed to discriminating between one or more of: arrhythmia and non-arrhythmia; supra-ventricular tachycardia and ventricular tachycardia; polymorphic ventricular tachycardia and monomorphic ventricular tachycardia; left-ventricular tachycardia and right-ventricular tachycardia; and premature atrial contraction and premature ventricular contraction. Further embodiments determine the beat-to-beat variance of a characteristic of the one or more cardiac signal vectors to aid in discrimination.

Example embodiments include discriminating premature atrial contraction by detecting a positive phase of a dominant orientation of the one or more cardiac signal vectors, and discriminating premature ventricular contraction by detecting a negative phase of a dominant orientation of one or more cardiac signal vectors. Further embodiments may establish a baseline from the performed source separation, wherein the change may be detected using a subsequent source separation. Examples of detected changes in accordance with embodiments of the present invention include one or more of: a phase angle change of the one or more cardiac signal vectors, a magnitude change of the one or more cardiac signal vectors, a variance change of the one or more cardiac signal vectors, a power spectral density change of the phase of the one or more cardiac signal vectors, a power spectral density change of the magnitude of the one or more cardiac signal vectors, a trajectory change of the one or more cardiac signal vectors, a temporal profile change of the one or more cardiac signal vectors, a rate of change of phase angle of the one or more cardiac signal vectors, a rate of change of magnitude of the one or more cardiac signal vectors, a rate of change of variance of the one or more cardiac signal vectors, a rate of change of temporal profile of the one or more cardiac signal vectors, a trend of the phase angle of the one or more cardiac signal vectors, a trend of the magnitude of the one or more cardiac signal vectors, a trend of the variance of the one or more cardiac signal vectors, and a trend of the temporal profile of the one or more cardiac signal vectors.

Other embodiments of methods in accordance with the present invention involve sensing a plurality of composite cardiac signals using a plurality of implantable electrodes, performing a source separation that produces a plurality of vectors, and selecting one or more vectors from the plurality of vectors associated with the specific segment of a cardiac cycle. Information associated with the selected one or more vectors is stored and used to track the selected one or more vectors, which may be used for discriminating cardiac arrhythmias.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

BRIEF DESCRIPTION OF THE DRAWINGS

FIGS. 1A and 1B are pictorial diagrams of an electrocardiogram (ECG) waveform for three consecutive heartbeats (FIG. 1A) and a magnified portion of the ECG waveform for the first two consecutive heartbeats (FIG. 1B);

Figure 1B:
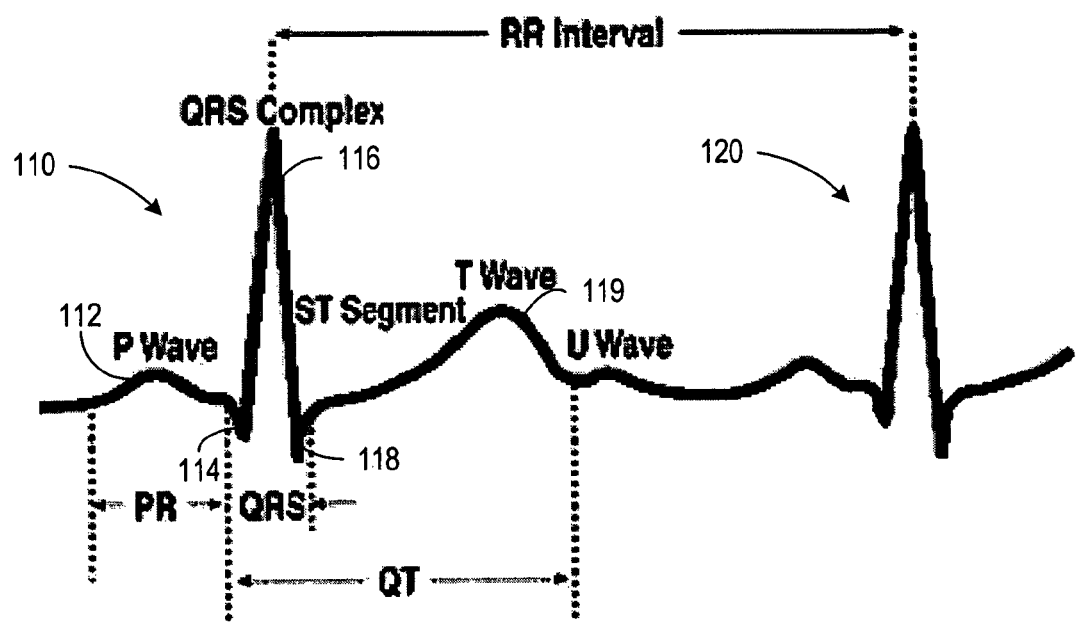

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings, which form a part hereof, and in which is shown by way of illustration, various embodiments in which the invention may be practiced. It is to be understood that other embodiments may be utilized, and structural and functional changes may be made without departing from the scope of the present invention.

An implanted device according to the present invention may include one or more of the features, structures, methods, or combinations thereof described hereinbelow. For example, a cardiac monitor or a cardiac stimulator may be implemented to include one or more of the advantageous features and/or processes described below. It is intended that such a monitor, stimulator, or other implanted or partially implanted device need not include all of the features described herein, but may be implemented to include selected features that provide for unique structures and/or functionality. Such a device may be implemented to provide a variety of therapeutic or diagnostic functions.

A wide variety of implantable cardiac monitoring and/or stimulation devices may be configured to implement a cardiac activation sequence monitoring and/or tracking methodology of the present invention. A non-limiting, representative list of such devices includes cardiac monitors, pacemakers, cardiovertors, defibrillators, resynchronizers, and other cardiac monitoring and therapy delivery devices, including cardiac devices that include or work in coordination with neurostimulating devices, drug pumps, or other therapies. These devices may be configured with a variety of electrode arrangements, including transvenous, endocardial, and epicardial electrodes (i.e., intrathoracic electrodes), and/or subcutaneous, non-intrathoracic electrodes, including can, header, and indifferent electrodes, and subcutaneous array or lead electrodes (i.e., non-intrathoracic electrodes).

Methods and systems in accordance with the present invention employ cardiac signal separation for arrhythmia discrimination using cardiac activation sequence information. Composite cardiac signals are sensed using multiple implantable electrodes. Signal separation is used to produce cardiac activation signal vectors associated with one or more cardiac activation sequences. A change in the signal vector may be detected using subsequent separations. The change may be used to diagnose, detect, predict, quantify, and/or qualify an event such as ischemia, an arrhythmia, a myocardial infarction, or other pathologic change. Information associated with the vectors may be stored and used to track the vectors.

Embodiments of the present invention may be implemented in the context of a wide variety of cardiac devices, such as those listed above, and are referred to herein generally as patient-internal medical devices (PIMD) for convenience. A PIMD implemented in accordance with the present invention may incorporate one or more of the electrode types identified above and/or combinations thereof.

Cardiac activation sequence monitoring and/or tracking systems of the present invention employ more than two electrodes of varying location, and possibly of varying configuration. In one embodiment, for example, two or more electrodes may conveniently be located on the PIMD header, whereas the can of the PIMD itself may be the third electrode. In another embodiment, one electrode may be located on the PIMD header, another is the can electrode, and a third may be a PIMD antenna used for RF telemetry.

Electrocardiogram (ECG) signals originate from electrophysiological signals originating in and propagated through the cardiac tissue, which provide for the cardiac muscle contraction that pumps blood through the body. A sensed ECG signal is effectively a superposition of all the depolarizations occurring within the heart that are associated with cardiac contraction, along with noise components. The propagation of the depolarizations through the heart may be referred to as a depolarization wavefront. The sequence of depolarization wavefront propagation through the chambers of the heart, providing the sequential timing of the heart's pumping, is designated an activation sequence.

A signal separation algorithm may be implemented to separate activation sequence components of ECG signals, and produce one or more cardiac signal vectors associated with all or a portion of one or more cardiac activation sequences based on the separation. The activation sequence components may be considered as the signal sources that make up the ECG signals, and the signal separation process may be referred to as a source separation process or simply source separation. One illustrative signal source separation methodology useful for producing cardiac signal vectors associated with cardiac activation sequences is designated blind source separation, which will be described in further detail below.

In general, the quality of the electrocardiogram or electrogram sensed from one pair of electrodes of a PIMD depends on the orientation of the electrodes with respect to the depolarization wavefront produced by the heart. The signal sensed on an electrode bi-pole is the projection of the ECG vector in the direction of the bi-pole. Cardiac activation sequence monitoring and/or tracking algorithms of the present invention advantageously exploit the strong correlation of signals from a common origin (the heart) across spatially distributed electrodes to detect, monitor, and/or track ischemia.

Referring to FIGS. 1A and 1B, an ECG waveform 100 describes the activation sequence of a patient's heart as recorded, for example, by a bi-polar cardiac sensing electrode. The graph of FIG. 1A illustrates an example of the ECG waveform 100 for three heartbeats, denoted as a first heartbeat 110, a second heartbeat 120, and a third heartbeat 130. FIG. 1B is a magnified view of the first two heartbeats 110, 120 of the ECG waveform identified by bracket 1B in FIG. 1A.

Referring to the first heartbeat 110, the portion of the ECG waveform representing depolarization of the atrial muscle fibers is referred to as a P-wave 112. Depolarization of the ventricular muscle fibers is collectively represented by a Q 114, R 116, and S 118 waves of the ECG waveform 100, typically referred to as the QRS complex, which is a well-known morphologic feature of electrocardiograms. Finally, the portion of the waveform representing repolarization of the ventricular muscle fibers is known as a T wave 119. Between contractions, the ECG waveform returns to an isopotential level.

The sensed ECG waveform 100 illustrated in FIGS. 1A and 1B is typical of a far-field ECG signal, effectively a superposition of all the depolarizations occurring within the heart that result in contraction. The ECG waveform 100 may also be obtained indirectly, such as by using a signal separation methodology. Signal separation methodologies, such as blind source separation (BSS), are able to separate signals from individual sources that are mixed together into a composite signal. The main principle of signal separation works on the premise that spatially distributed electrodes collect components of a signal from a common origin (e.g., the heart) with the result that these components may be strongly correlated to each other. In addition, these components may also be weakly correlated to components of another origin (e.g., noise). A signal separation algorithm may be implemented to separate these components according to their sources and produce one or more cardiac signal vectors associated with all or a portion of one or more cardiac activation sequences based on the source separation.

Figure 2:
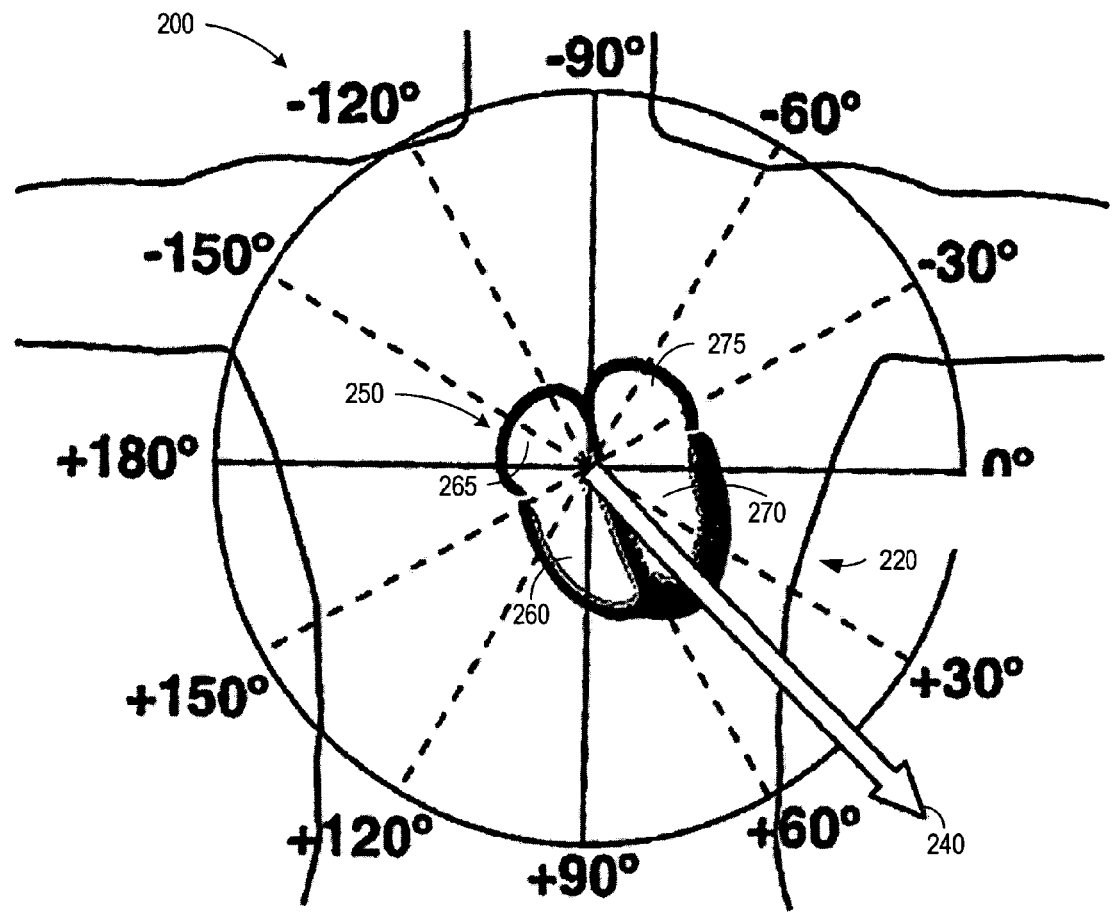
FIG. 2 is a polar plot of a cardiac vector superimposed over a frontal view of a thorax, with the origin of the polar plot located at the atrioventricular (AV) node of a patient's heart.

FIG. 2 illustrates a convenient reference for describing cardiac signal vectors associated with a depolarization wavefront. FIG. 2 is a polar plot 200 of a cardiac vector 240 superimposed over a frontal view of a thorax 220, with the origin of the polar plot located at a patient's heart 250, specifically, the atrioventricular (AV) node of the heart 250. The heart 250 is a four-chambered pump that is largely composed of a special type of striated muscle, called myocardium. Two major pumps operate in the heart, and they are a right ventricle 260, which pumps blood into pulmonary circulation, and a left ventricle 270, which pumps blood into the systemic circulation. Each of these pumps is connected to its associated atrium, called a right atrium 265 and a left atrium 275.

The cardiac vector 240 is describable as having an angle, in degrees, about a circle of the polar plot 200, and having a magnitude, illustrated as a distance from the origin of the tip of the cardiac vector 240. The polar plot 200 is divided into halves by a horizontal line indicating 0 degrees on the patient's left, and +/−180 degrees on the patient's right, and further divided into quadrants by a vertical line indicated by −90 degrees at the patient's head and +90 degrees on the bottom. The cardiac vector 240 is projectable onto the two-dimensional plane designated by the polar plot 200.

The cardiac vector 240 is a measure of all or a portion of the projection of a heart's activation sequence onto the polar plot 200. The heart possesses a specialized conduction system that ensures, under normal conditions, that the overall timing of ventricular and atrial pumping is optimal for producing cardiac output, the amount of blood pumped by the heart per minute. As described earlier, the normal pacemaker of the heart is a self-firing unit located in the right atrium called the sinoatrial node. The electrical depolarization generated by this structure activates contraction of the two atria. The depolarization wavefront then reaches the specialized conduction system using conducting pathways within and between the atria. The depolarization is conducted to the atrioventricular node, and transmitted down a rapid conduction system composed of the right and left bundle branches, to stimulate contraction of the two ventricles.

The normal pacemaker and rapid conduction system are influenced by intrinsic automatic activity and by the autonomic nervous system, which modulates heart rate and the speed with which electrical depolarizations are conducted through the specialized conduction system. There are many diseases that interfere with the specialized conduction system of the heart, and many result in abnormally fast, slow, or irregular heart rhythms.

Figure 3A:
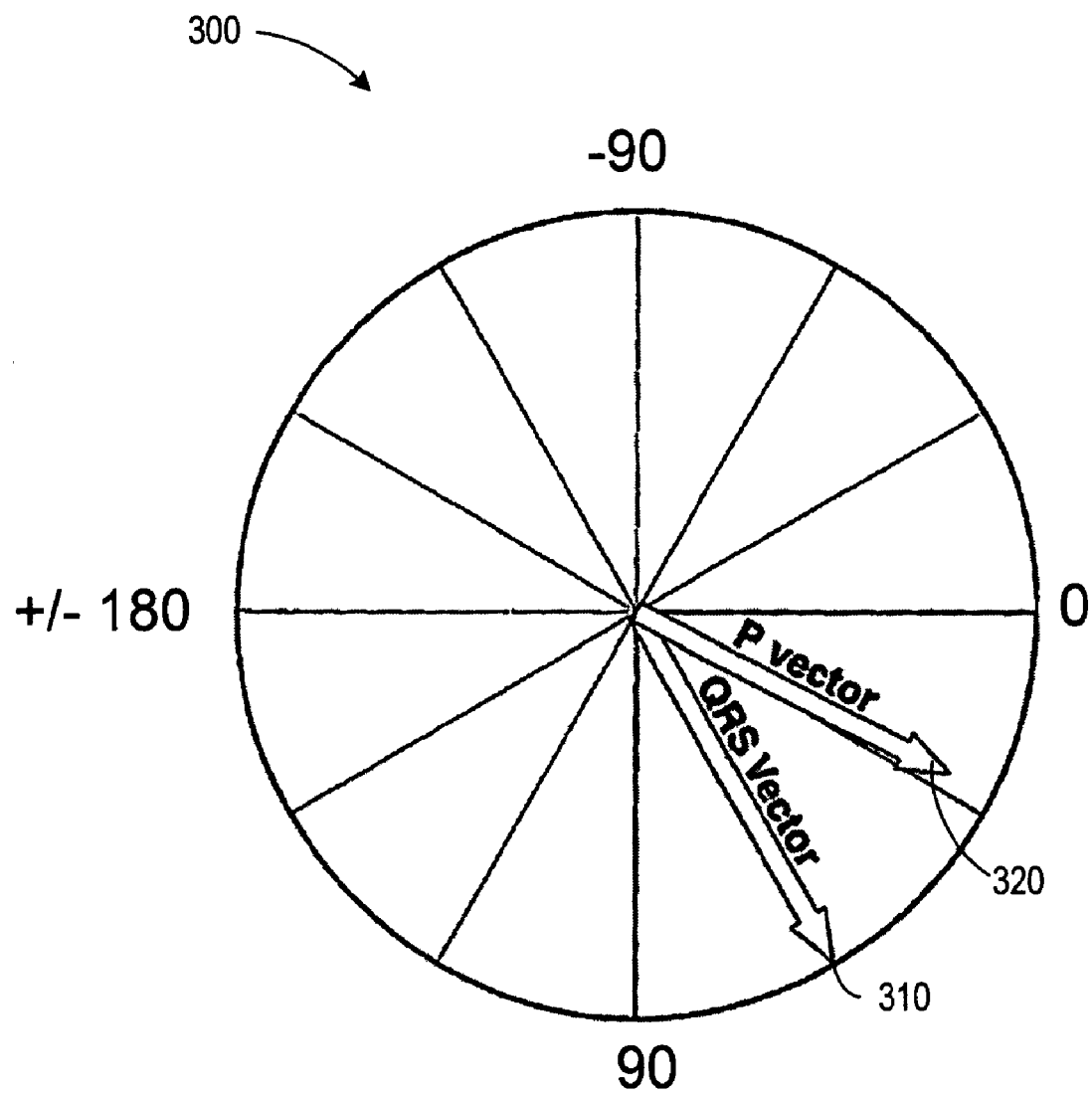
FIG. 3A is a polar plot of cardiac vectors obtained using a source separation in accordance with the present invention.

The cardiac vector 240 may be, for example, associated with the entire cardiac cycle, and describe the mean magnitude and mean angle of the cardiac cycle. Referring now to FIG. 3A, a polar plot 300 is illustrated of separate portions of the cardiac cycle that may make up the cardiac vector 240 of FIG. 2. As is illustrated in FIG. 3A, a QRS vector 310 and a P vector 320 are illustrated having approximately 60 degree and 30 degree angles, respectively. The QRS vector 310 may also be referred to as the QRS axis, and changes in the direction of the QRS vector may be referred to as QRS axis deviations.

The QRS vector 310 represents the projection of the mean magnitude and angle of the depolarization wavefront during the QRS portion of the cardiac cycle onto the polar plot 300. The P vector 320 represents the projection of the mean magnitude and angle of the depolarization wavefront during the P portion of the cardiac cycle onto the polar plot 300. The projection of any portion of the depolarization wavefront may be represented as a vector on the polar plot 300.

Further, any number of cardiac cycles may be combined to provide a statistical sample that may be represented by a vector as a projection onto the polar plot 300. Likewise, portions of the cardiac cycle over multiple cardiac cycles may also be combined, such as combining a weighted summation of only the P portion of the cardiac cycle over multiple cardiac cycles, for example.

Referring now to FIGS. 1 through 3A, the first, second, and third cardiac cycles 110, 120, and 130 may be analyzed using a window 140 (FIG. 1) applied concurrently to signals sensed by three or more cardiac sense electrodes. The ECG waveform signals 100 from all the sense electrodes, during the window 140, may be provided to a signal processor. The signal processor may then perform a source separation that provides the cardiac vector 240 (FIG. 2). The cardiac vector 240 then represents the orientation and magnitude of the cardiac vector that is effectively an average over all three cardiac cycles 110, 120, and 130.

Other windows are also useful. For example, a window 150 and a window 160 may provide each full cardiac cycle, such as the cardiac cycle 120 and the cardiac cycle 130 illustrated in FIG. 1, to a controller for analysis. The windows 150, 160 may be useful for beat-to-beat analysis, where the angle, magnitude, or other useful parameter from the separated cardiac vector 240 is compared between consecutive beats, or trended, for example.

Examples of other useful windows include a P-window 152, a QRS window 154, and an ST window 155 (FIG. 1) that provide within-beat vector analysis capability, such as by providing the P-vector 320 and the QRS-vector 310 illustrated in FIG. 3A. Providing a P-window 162 and/or a QRS-window 164, and/or an ST window 165 to subsequent beats, such as to the consecutive cardiac cycle 130 illustrated in FIG. 1, provides for subsequent separations that may provide information for tracking and monitoring changes and/or trends of windowed portions of the cardiac cycle or statistical samples of P, QRS, or T waves over more than 1 beat.

Figure 3B:
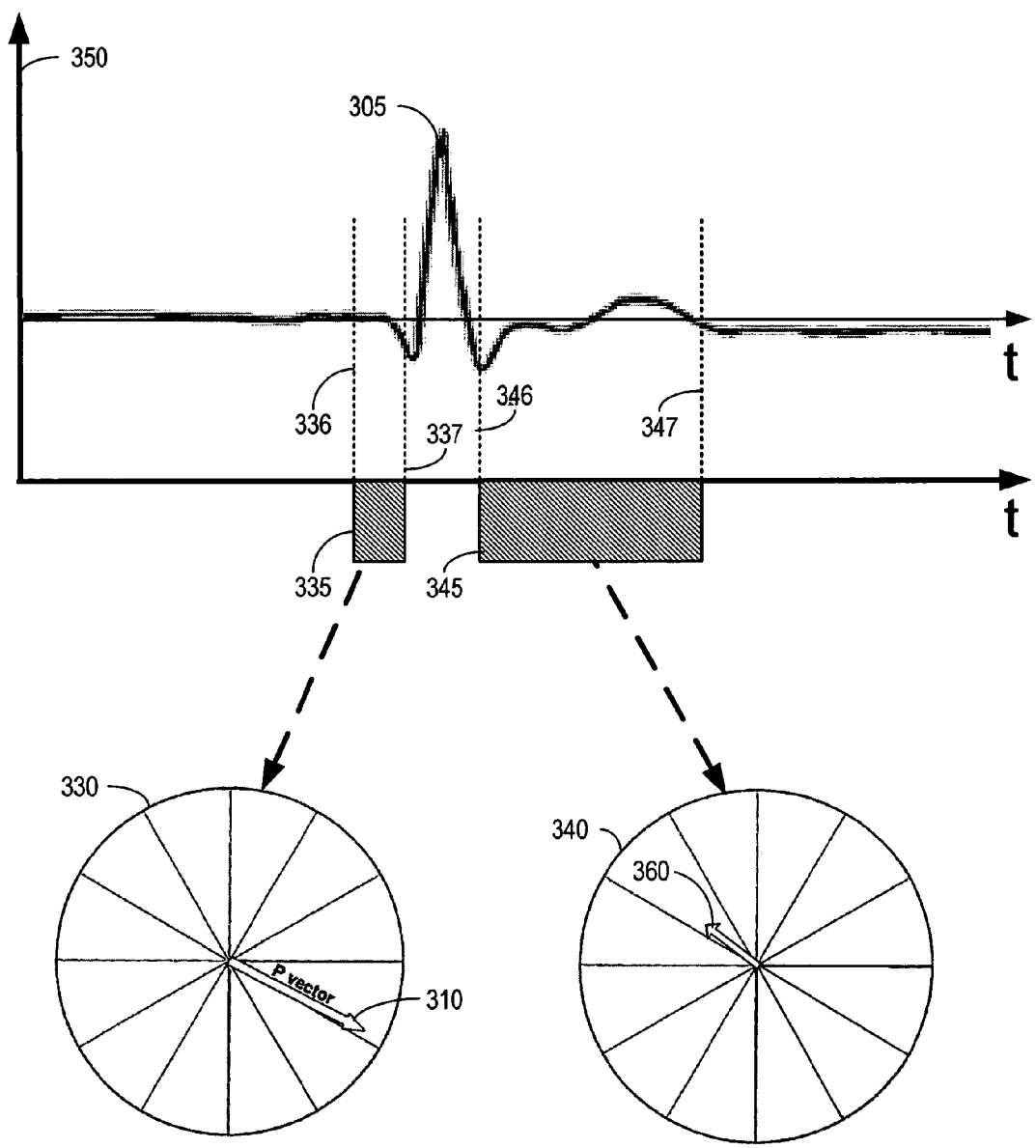
FIG. 3B illustrates polar plots of cardiac vectors obtained from selected portions of an electrocardiogram using source separation in accordance with the present invention.

Referring now to FIG. 3B, polar plots of cardiac vectors obtained from selected portions of an electrocardiogram are illustrated. In general, it may be desirable to define one or more detection windows associated with particular segments of a given patient's cardiac cycle. The detection windows may be associated with cardiac signal features, such as P, QRS, ST, and T wave features, for example. The detection windows may also be associated with other portions of the cardiac cycle that change in character as a result of changes in the pathology of a patient's heart. Such detection windows may be defined as fixed or triggerable windows.

Detection windows may include unit step functions to initiate and terminate the window, or may be tapered or otherwise initiate and terminate using smoothing functions such as Bartlett, Bessel, Butterworth, Hanning, Hamming, Chebyshev, Welch, or other functions and/or filters. The detection windows associated with particular cardiac signal features or segments may have widths sufficient to sense cardiac vectors resulting from normal or expected cardiac activity. Aberrant or unexpected cardiac activity may result in the failure of a given cardiac vector to fall within a range indicative of normal cardiac behavior. Detection of a given cardiac vector beyond a normal range may trigger one or more operations, including increased monitoring or diagnostic operations, therapy delivery, patient or physician alerting, communication of warning and/or device/physiological data to an external system (e.g., advanced patient management system) or other responsive operation.

An ECG signal 305 is plotted in FIG. 3B as a signal amplitude 350 on the ordinate versus time on the abscissa. One cardiac cycle is illustrated. The P portion of the ECG signal 305 may be defined using a P-window 335 that opens at a time 336 and closes at a time 337. A source separation performed on the ECG signal 305 within the P-window 335 produces the P vector 310 illustrated on a polar plot 330. The angle of the P vector 310 indicates the angle of the vector summation of the depolarization wavefront during the time of the P-window 335 for the ECG signal 305.

The ST portion of the ECG signal 305 may be defined using an ST-window 345 that opens at a time 346 and closes at a time 347. A source separation performed on the ECG signal 305 within the ST-window 345 produces the ST vector 360 illustrated on a polar plot 340. The angle of the ST vector 360 indicates the angle of the vector summation of the depolarization wavefront during the time of the ST-window 345 for the ECG signal 305.

The P vector 310 and the ST vector 360 may be acquired as baselines, for future comparisons. If baselines for the P vector 310 and the ST vector 360 are already established, the P vector 310 and ST vector 360 may be compared relative to their baselines for monitoring and tracking purposes. As indicated above, detection of P vector 310 or ST vector 360 beyond a predetermined range may trigger one or more responsive operations.

Cardiac activation sequence monitoring and tracking, to monitor changes and/or trends as described above, may be useful to determine initial activation sequences, and track acute and chronic changes in the activation sequences. Information from the patient's activation sequence is valuable for identification, discrimination, and trending of conditions such as conduction anomalies (e.g. AV block, bundle branch block, retrograde conduction) and cardiac arrhythmias (e.g. discriminating between supraventricular tachycardia versus ventricular tachycardia, reentrant supraventricular tachycardia versus atrial fibrillation, or other desirable discrimination.) In addition to baseline establishment, monitoring, and tracking, activation sequence information may also be useful for determining pace capture for autocapture/autothreshold algorithms, adjustment, optimization, or initiation of cardiac resynchronization therapy, and optimization or initiation of anti-arrhythmia therapies, for example.

Figure 4:
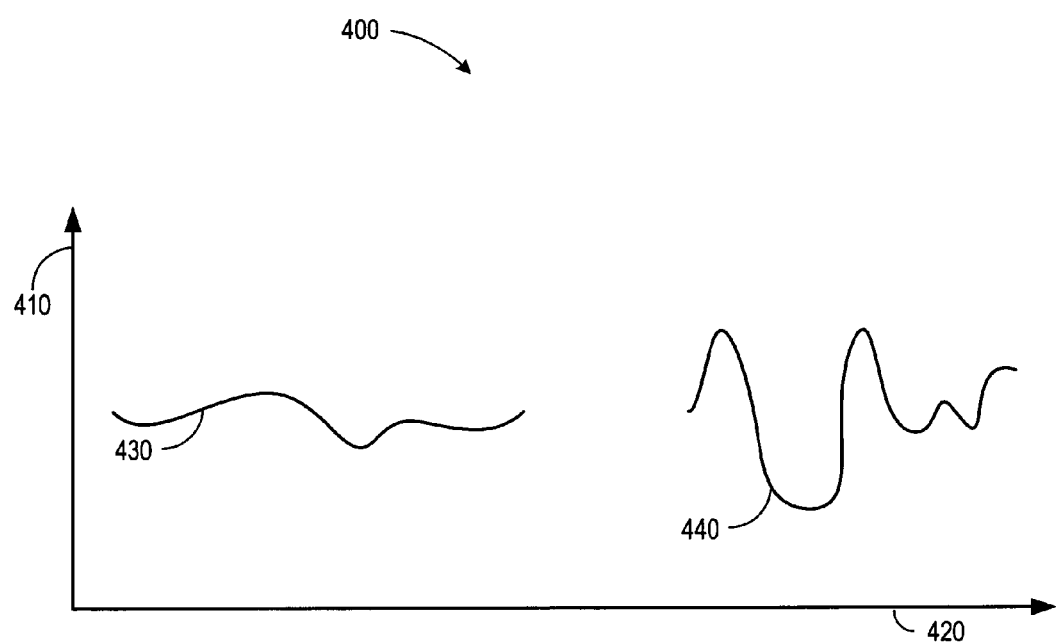
FIG. 4 is a graph of temporal profiles of a cardiac vector useful for diagnosing a cardiac disease in accordance with the present invention.

FIG. 4 illustrates another convenient reference for describing cardiac signal vectors associated with a depolarization wavefront. FIG. 4 is a graph 400 of temporal profiles of a measure of a cardiac vector useful for diagnosing diseases and anomalous conditions in accordance with the present invention. The graph 400 contains a first temporal profile 430 of a cardiac vector, and a second temporal profile 440 of the same cardiac vector after a change has occurred. An abscissa 420 of the graph 400 is time related, and an ordinate 410 of the graph 400 is related to a measure of the cardiac vector.

The ordinate 410 may be, for example, the angle of the cardiac vector. A non-limiting, non-exhaustive list of measures of a vector useful for the ordinate 410 includes: angle; magnitude; variance; power spectral density; rate of change of angle; rate of change of magnitude; rate of change of variance; or other measure indicative of a change in the cardiac activation sequence. As an example, consider the angle of the P vector 320 illustrated in FIG. 3A. In this example, the ordinate 410 would be indicated in degrees, with the first temporal profile 430 varying from around 30 degrees. The abscissa 420 may be time, designated in cardiac cycles, with a measure made of the P vector 320 for every cardiac cycle. The angle of the P vector 320 may be plotted on the graph 400 at any interval of cardiac cycles, thereby displaying variance and trends in the angle of the P vector 320 over many cardiac cycles.

After some change occurs, such as a pathological change in the patient's heart, the second temporal profile 440 may be plotted using cardiac cycles occurring after the change. As is evident in the second temporal profile 440 versus the first temporal profile 430, the variance of the second temporal profile 440 is significantly larger than the variance of the first temporal profile 430. Changes such as this may be detected and used for arrhythmia discrimination in accordance with the present invention.

Figure 5A:
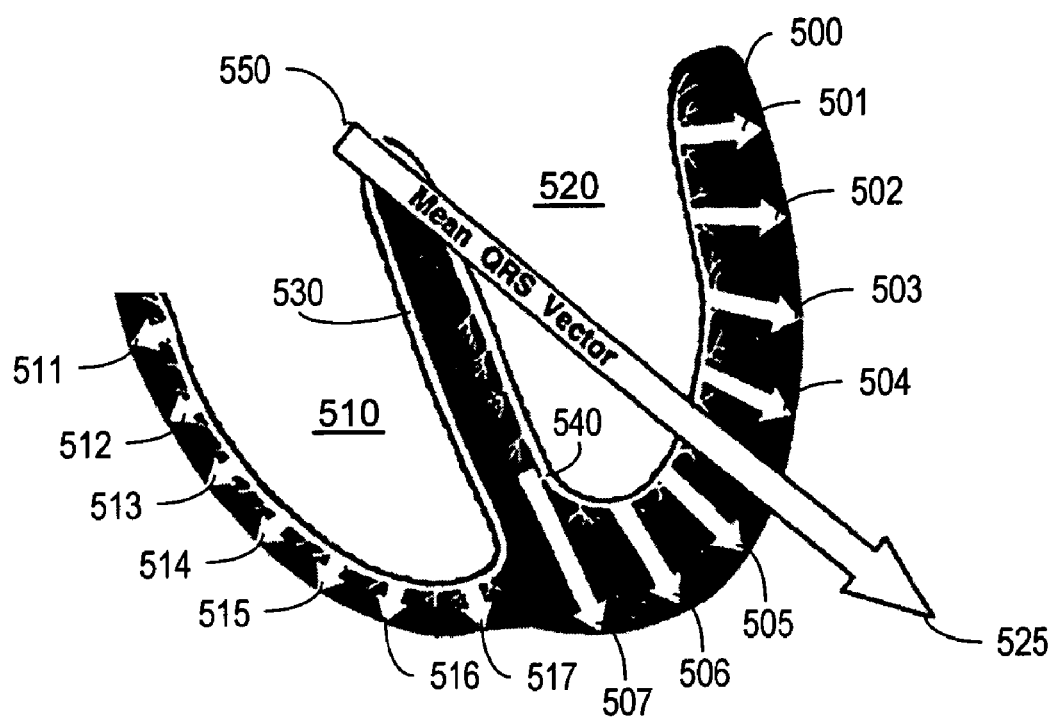
FIGS. 5A through 5D illustrate cardiac vectors superimposed over a sectional view of the ventricles of a patient's heart.

FIGS. 5A through 5D illustrate cardiac vectors superimposed over a sectional view of the ventricles of a patient's heart 500. Referring to FIG. 5A, the ventricular portion of a patient's heart is illustrated having a right ventricle 510 and a left ventricle 520 separated by the heart's septum. The specialized conduction system includes an atrioventricular node 550, which is used as the origin for cardiac vectors, such as a mean QRS vector 525.

A right bundle branch 530 conducts the depolarization wavefront from the atrioventricular node 550 to the wall of the right ventricle 510. Illustrated in the wall of the right ventricle 510 are a series of vectors 511-517, indicating the magnitude and angle of a local portion of the depolarization wavefront as it travels along the right ventricle 510.

A left bundle branch 540 conducts the depolarization wavefront from the atrioventricular node 550 to the wall of the left ventricle 520. Illustrated in the wall of the left ventricle 510 are a series of vectors 501-507, indicating the magnitude and angle of a local portion of the depolarization wavefront as it travels along the left ventricle 520.

The mean QRS vector 525 is the vector summation of the vectors 511-517 and the vectors 501-507. The mean QRS vector 525 may be typical of a healthy heart, here illustrated at about 40 degrees angle if using the polar plot of FIG. 3A. The mean QRS vector 525 varies from patient to patient depending on, for example, patient posture, and normal anatomical variation.

Figure 5B:
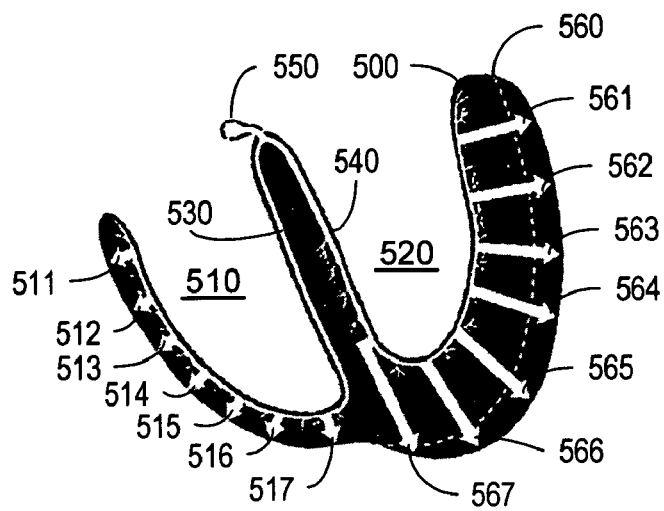

Referring now to FIG. 5B, the wall of the left ventricle 520 is enlarged, or hypertrophied, relative to FIG. 5A. In FIG. 5B, a dotted line 560 represents the wall of the left ventricle 520 in FIG. 5A, before hypertrophy. A series of local vectors 561-567 illustrate the larger local contribution to the mean QRS vector 525 from the hypertrophy related vectors 561-567 relative to the normal series of left ventricle vectors 501-507.

Figure 5C:
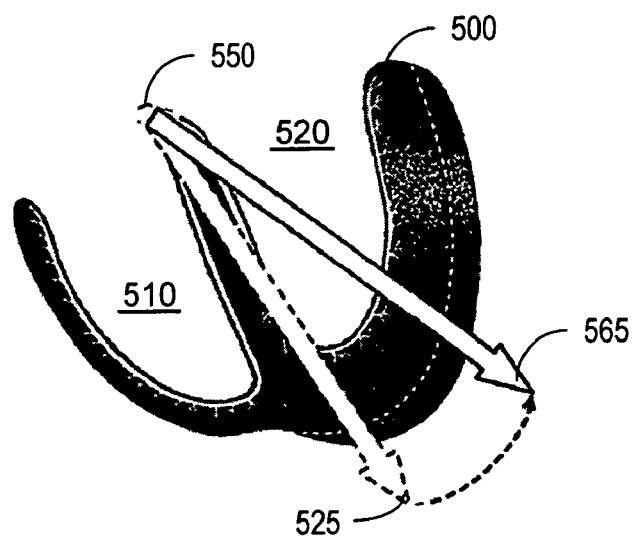

FIG. 5C illustrates how the mean QRS vector 525 from a normal heart may change to a mean hypertrophied QRS vector 565 after hypertrophy has occurred. For example, a PIMD may be implanted in a patient, and an initial analysis provides a baseline mean QRS vector 525 for the patient, indicative of a normal condition of the left ventricle 520. After a period of time, the patient's heart may be subject to hypertrophy. An analysis performed post-hypertrophy may result in finding the mean hypertrophied QRS vector 565. This change may be used to diagnose, verify and/or monitor hypertrophy of the patient's left ventricle.

Figure 5D:
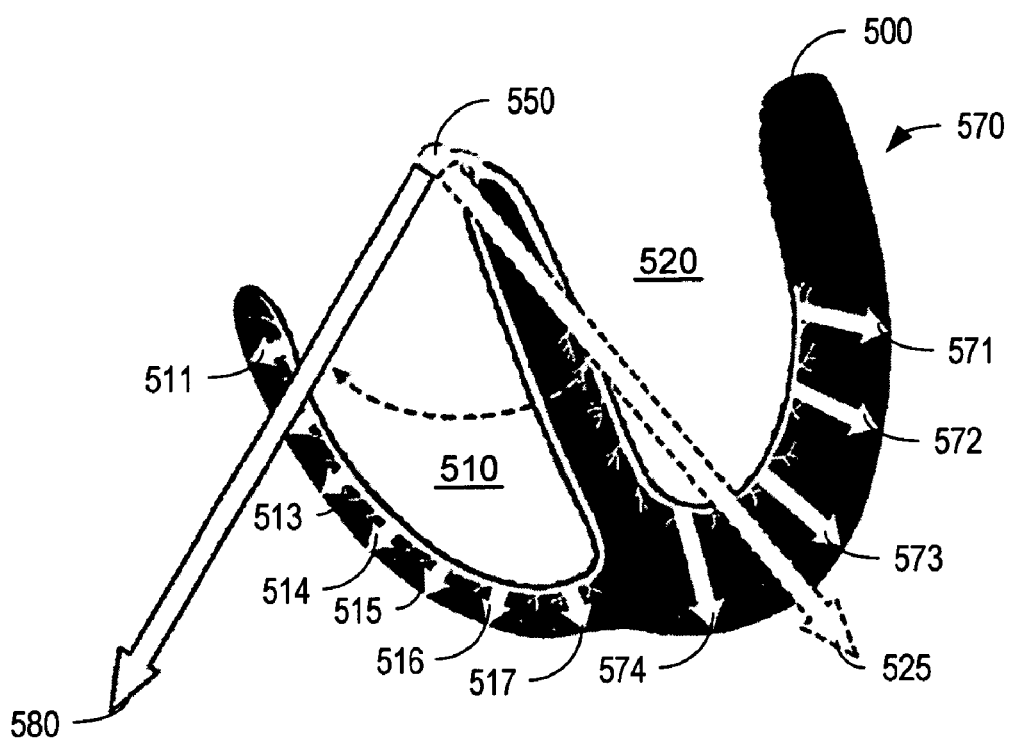

Another example of a pathological change that may be diagnosed and/or verified using embodiments of the present invention is a lessening or loss of blood supply to a portion of the heart, such as through a transient ischemia or myocardial infarction. The sectional view in FIG. 5D illustrates the left ventricle 520 having an infarcted portion 570 of the ventricular wall. As is evident in the infarcted portion 570, no depolarization is occurring, so only local depolarization vectors 571-574 contribute to the mean cardiac vector from the left ventricle 520. The infarction results in a change, for example, of the detected mean QRS vector 525 to an infarcted mean QRS vector 580. Other vectors such as the ST vector may also show the change. This change is evident as the angle of the cardiac vector moves from the second quadrant before infarction, to the third quadrant after infarction.

A PIMD that detects a change such as is illustrated in FIG. 5D has the potential to alert the patient and/or physician to a loss or lessening of blood supply to a portion of the heart muscle before permanent damage occurs. Early detection may result in greatly reduced morbidity from these kinds of events.

Figure 6A:
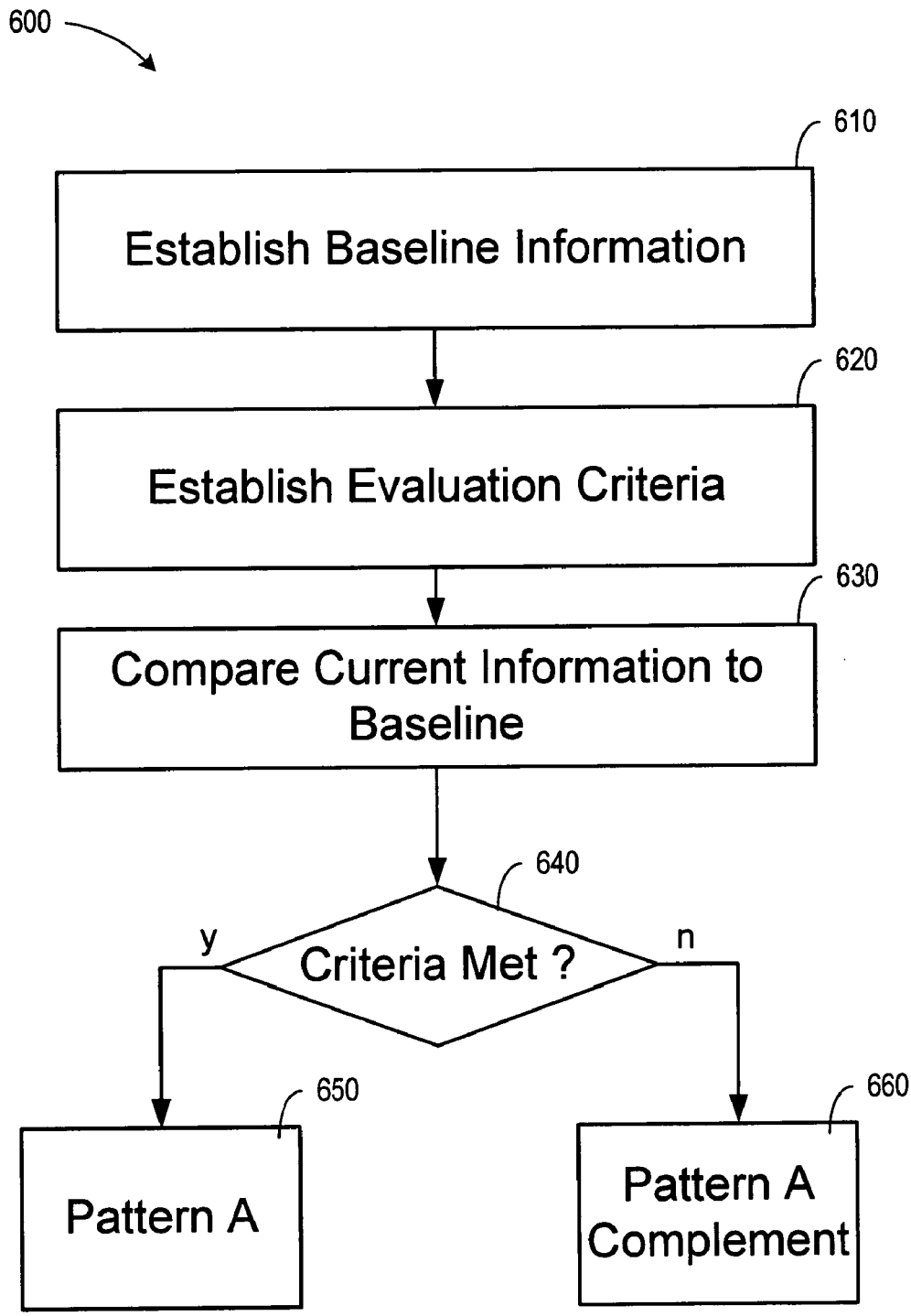
FIG. 6A is a block diagram of a method of detecting a change in one or more cardiac signal vectors associated with all or a portion of one or more cardiac activation sequences based on a source separation in accordance with the present invention.

FIG. 6A is a block diagram of a method 600 of detecting a change in one or more cardiac signal vectors associated with all or a portion of one or more cardiac activation sequences based on a source separation in accordance with the present invention. A baseline is established 610, providing information that may be monitored or tracked relative to a patient's electrophysiological signals. The baseline 610 may be established from an initial source separation, that provides initial cardiac signal information as a baseline. Alternately, or additionally, the baseline 610 may be established by a PIMD manufacturer from clinical data, or a patient's baseline 610 may be established by a clinician before, during, or after a PIMD implant procedure. The baseline 610 may be established as a rolling average of recent patient information from prior source separations, for example.

Evaluation criteria is established 620 to provide an index for comparison to the baseline 610. For example, the evaluation criteria 620 may be any parameter or characteristic determinable or measurable from the patient's electrophysiology information. A non-exhaustive, non-limiting list of evaluation criteria 620 includes: an angle change of one or more cardiac signal vectors; a magnitude change of one or more cardiac signal vectors; a variance change of one or more cardiac signal vectors; a power spectral density change of the angle of one or more cardiac signal vectors; a power spectral density change of the magnitude of one or more cardiac signal vectors; a trajectory change of one or more cardiac signal vectors; a temporal profile change of one or more cardiac signal vectors; a rate of change of angle of one or more cardiac signal vectors; a rate of change of magnitude of one or more cardiac signal vectors; a rate of change of variance of one or more cardiac signal vectors; a rate of change of temporal profile of one or more cardiac signal vectors; a trend of the angle of one or more cardiac signal vectors; a trend of the magnitude of one or more cardiac signal vectors; a trend of the variance of one or more cardiac signal vectors; and a trend of the temporal profile of one or more cardiac signal vectors.

For example, an initial source separation may be performed by a PIMD on a patient post-implant. The separation may produce the baseline 610 of the patient's average full cardiac cycle, such as the cardiac vector 240 illustrated in FIG. 2. The vector 240 may have a characteristic, such as the angle, determined as +45 degrees. The evaluation criteria 620 may be, for example, that the patient's average full cardiac cycle vector's angle should be within +40 to +50 degrees.

A comparison 630 is performed to determine the latest patient information relative to the baseline 610. For example, the results of a latest source separation algorithm may provide the latest average full cardiac cycle vector's angle for the patient. Continuing with the above example, the comparison 630 may check the latest angle of the patient's average full cardiac cycle vector's angle against the +40 to +50 degree criteria.

A decision 640 selects an outcome based on the comparison 630. If the criteria is met, for example if the latest angle is within +40 to +50 degrees as outlined above, then a pattern A 650 is considered to be the patient's latest condition. For example, the pattern A 650 may be defined as an insufficient change to require some sort of action by the PIMD. If the criteria 620 is not met at decision 640, then a pattern A complement 660 condition is considered to be the patient's latest condition. The pattern A complement 660 condition may be defined as requiring some sort of action by the PIMD, such as reporting the condition, further evaluating the patient's cardiac rhythms, preparing a defibrillator for a shock, or other desired action.

Figure 6B:
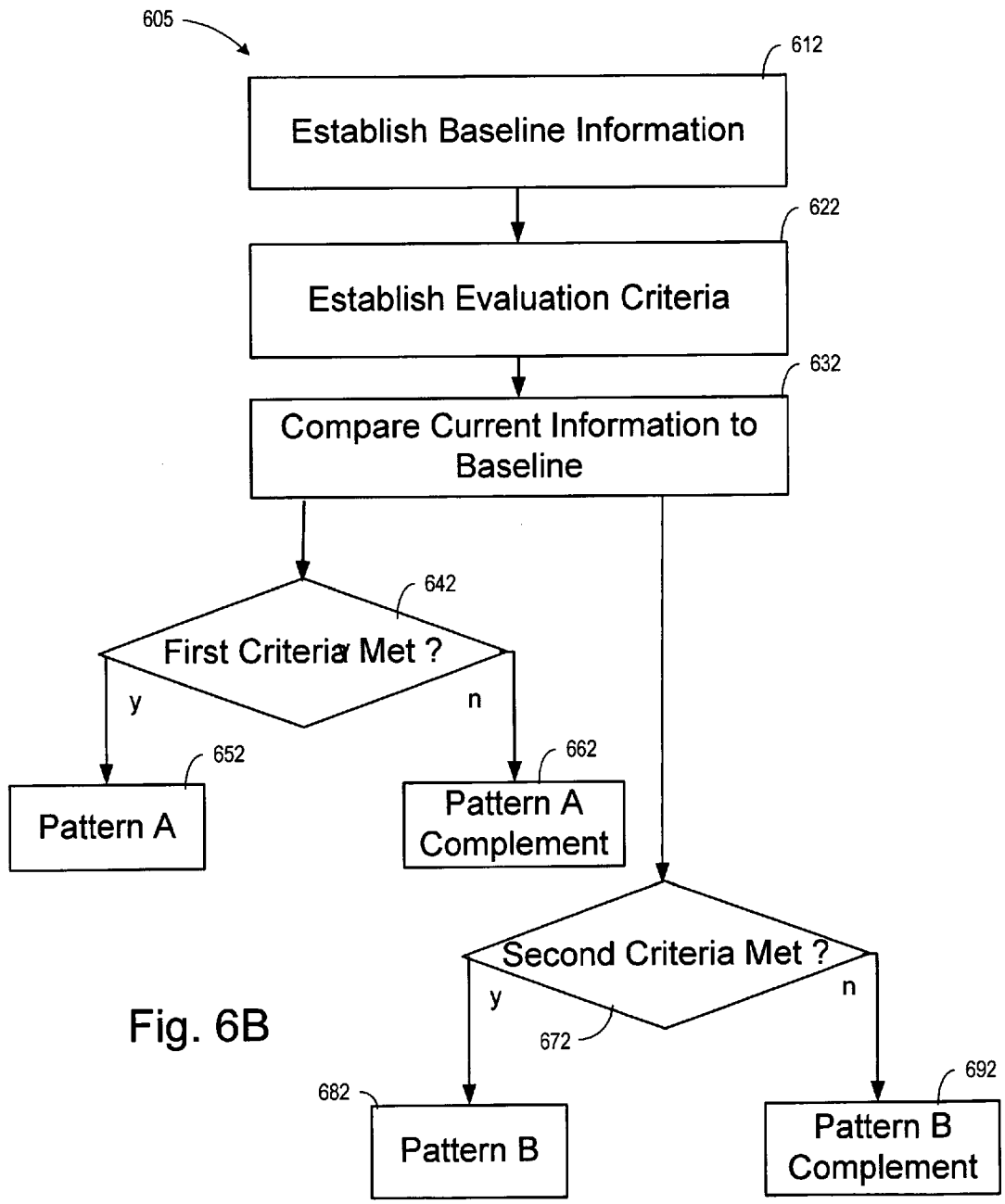
FIG. 6B is a block diagram of another embodiment of a method of detecting a change in one or more cardiac signal vectors associated with all or a portion of one or more cardiac activation sequences based on a source separation in accordance with the present invention.

FIG. 6B is a block diagram of another embodiment of a method 605 of detecting a change in one or more cardiac signal vectors associated with all or a portion of one or more cardiac activation sequences, when the criteria for baseline shift includes two criteria. It is contemplated that any number of criteria may be used or combined in accordance with the present invention. The use of two criteria with reference to FIG. 6B is for purposes of explanation as to how to extend methods of the present invention to multiple criteria, and is not intended as a limiting example.

A baseline is established 612, providing information that may be monitored or tracked from a patient's electrophysiological signals. The baseline 612 may be established from an initial source separation, that provides initial cardiac signal information as a baseline. Alternately, or additionally, the baseline 612 may be established by a PIMD manufacturer from clinical data, or a patient's baseline 612 may be established by a clinician before, during, or after a PIMD implant procedure. The baseline 612 may be established as a rolling average of recent patient information from prior source separations, for example.

Evaluation criteria are established 622 to provide indices for comparison to the baseline 612. For example, the evaluation criteria 622 may be any parameters or characteristics determinable or measurable from the patient's electrophysiology information. A non-exhaustive, non-limiting list of evaluation criteria 622 includes those described previously with respect to FIG. 6A. It is further contemplated that a single criterion may be compared with respect to multiple baselines, and/or that multiple criteria may each be compared with respect to their own unique baseline established for each particular criterion.

Baselines may be pre-defined using, for example, clinical data, and/or baselines may be established using initial source separations. For example, and described in more detail below, a source separation may provide an orthogonal coordinate system, with vectors described using a series of coefficients matched to a series of unit direction vectors. One or more angles may be calculated using trigonometric identities to indicate a vector's direction relative to other vectors in the coordinate system. Subsequent source separations provide revised sets of coefficients, from which changes in vector direction may be determined using the same trigonometric identities. In an n-dimensional space, (n−1) angles may be resolved and used for comparison and tracking in accordance with the present invention.

For example, an initial source separation may be performed by a PIMD on a patient post-implant. The separation may produce the baseline 612 of the patient's cardiac cycle, such as the QRS-vector 310 and the P-vector 320 illustrated in FIG. 3A. The QRS-vector 310 may have the angle determined as +45 degrees. The P-vector 320 may have the angle determined as +28 degrees. The evaluation criteria 622 may be, for example, that the patient's QRS-vector's angle should be within +40 to +50 degrees and that the patient's P-vector angle should be within +25 to +30 degrees.

A comparison 632 is performed to determine the latest patient information relative to the baseline 612. For example, the results of a latest source separation algorithm may provide the latest angles of the QRS-vector and P-vector for the patient. Continuing with the above example, the comparison 632 may check the latest angles of the patient's QRS-vector and P-vector against the +40 to +50 degree and +25 to +30 degree criteria respectively.

A first decision 642 selects a first outcome based on the comparison 632. If the first criteria is met, for example if the latest angle of the QRS-vector is within +40 to +50 degrees as outlined above, then a pattern A 652 is considered to be the patient's latest condition. For example, the pattern A 652 may be defined as an insufficient change to require some sort of action by the PIMD. If the criteria 622 is not met at decision 642, then a pattern A complement 662 condition is considered to be the patient's latest condition. The pattern A complement 662 condition may be defined as requiring some sort of action by the PIMD, such as reporting the condition, further evaluating the patient's cardiac rhythms, preparing a defibrillator for a shock, or other desired action.

A second criteria decision 672 is performed to check for a second outcome based on the second criteria. If the second criteria is met, for example if the latest angle of the P-vector is within +25 to +30 degrees as outlined above, then a pattern B 682 is considered to be the patient's latest condition. For example, the pattern B 682 may be defined as an insufficient change to require some sort of second action by the PIMD. If the criteria 622 is not met at decision 672, then a pattern B complement 692 condition is considered to be the patient's latest condition. The pattern B complement 692 condition may be defined as requiring some sort of second action by the PIMD.

Table 1 below provides a non-limiting non-exhaustive list of conditions that may be detected by monitoring and/or tracking cardiac activation sequences in accordance with the present invention.

TABLE 1

Conditions associated with QRS Axis Deviations

First Source (Normal −30 to +90 degrees)
Left Axis Deviation: ≧−30°

Left Anterior Fascicular Block (LAFB) axis −45° to −90°
Some cases of inferior myocardial infarction
with QR complex
Inferior Myocardial Infarction +
LAFB in same patient (QS or QRS complex)
Some cases of left ventricular hypertrophy
Some cases of left bundle branch block
Ostium primum Atrial Septal Defect and other endocardial cushion defects
Some cases of Wolff-Parkinson-White syndrome syndrome (large negative delta wave)
Right Axis Deviation: ≧ +90°

Left Posterior Fascicular Block (LPFB):
Many causes of right heart overload and pulmonary hypertension
High lateral wall Myocardial Infarction
with QR or QS complex
Some cases of right bundle branch block
Some cases of Wolff-Parkinson-White syndrome syndrome
Children, teenagers, and some young adults
Bizarre QRS axis: +150° to −90°

Figure 6C:
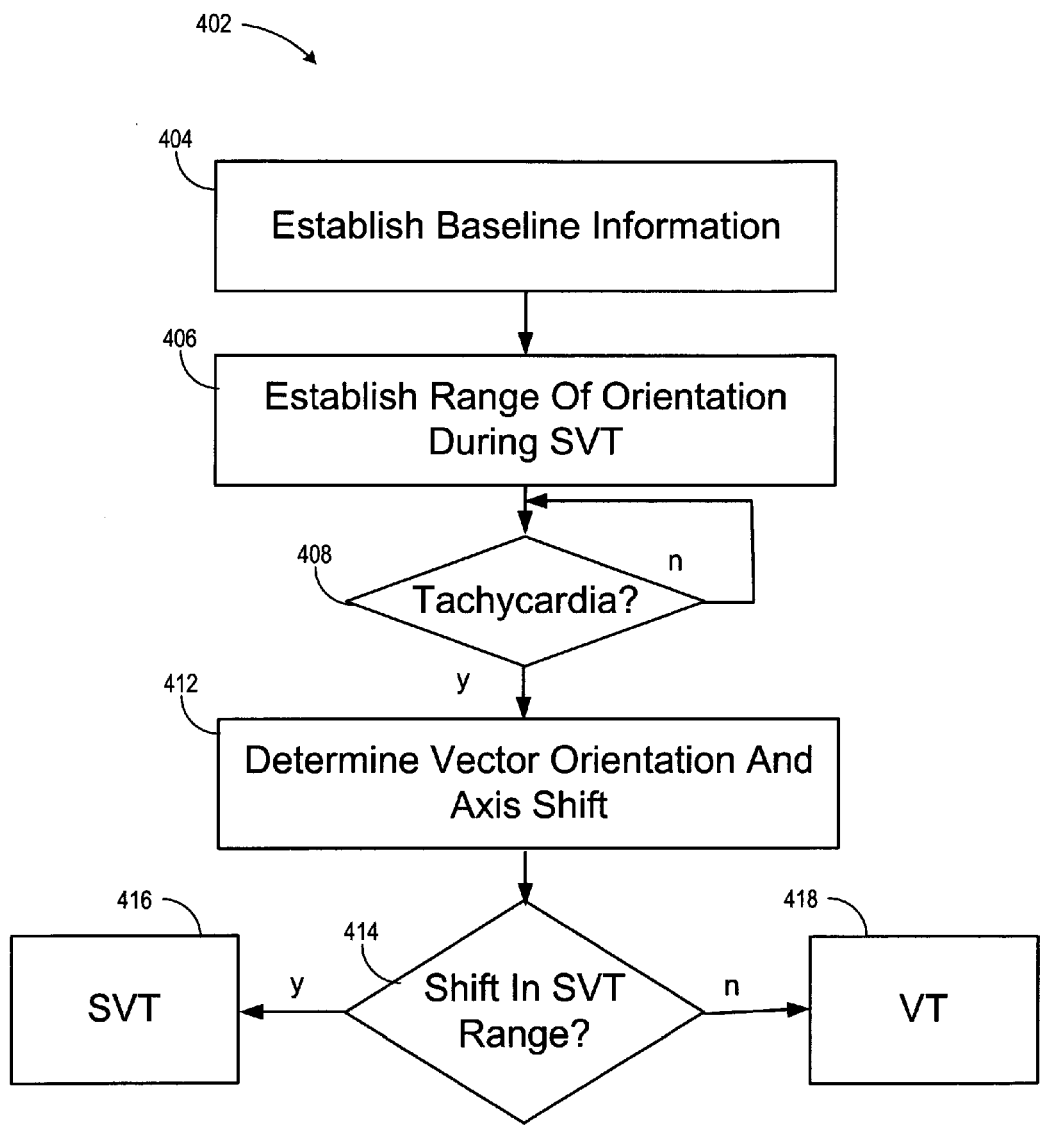
FIG. 6C is a flow chart of a method of differentiating supra-ventricular tachycardia (SVT) from ventricular tachycardia (VT) in accordance with the present invention.

Dextrocardia
Some cases of complex congenital heart disease (e.g., transposition)
Some cases of ventricular tachycardia
Second Source
QRS Axis Deviation Left anterior fascicular block (LAFB)
Right ventricular hypertrophy
Left bundle branch block Acute Myocardial Infarction:
Hypertensive heart disease
Coronary artery disease
Idiopathic conducting system disease
Acute Myocardial Infarction -
inferior left ventricular free wall accessory pathway (Wolff-Parkinson-White syndrome)
Posteroseptal accessory pathway
left posterior fascicular block
Chronic Obstructive Pulmonary Disease (uncommon - 10%)
Other conduction defects:
left ventricular hypertrophy
Right bundle branch block
Elevated diaphragm: R anterior hemiblock
Pregnancy
Pacing of R ventricle
Abdominal mass
Pulmonary conditions TABLE 1-continued Conditions associated with QRS Axis Deviations Ascites
Pulmonary hypertension
Tumor
Chronic Obstructive Pulmonary Disease
Conduction defects: Emphysema/bronchitis
R ventricular (apical) pacing
Pulmonary emboli/infarcts
Systemic hypertension, esp. chronic
Congenital defects
Valvular lesions
Rheumatic heart disease
Pulmonic stenosis
Aortic regurgitation
Mitral regurgitation
Mitral stenosis
Coarctation of the aorta
Tricuspid regurgitation
Hyperkalemia
Pulmonic stenosis
Normal variant in obese and in elderly
Pulmonic regurgitation FIG. 6C is a flow chart of a method 402 of differentiating supra-ventricular tachycardia (SVT) from ventricular tachycardia (VT) in accordance with the present invention. The method 402 establishes baseline information 404 regarding cardiac activation sequence vector information. For example, baselines may be established using clinical trials, providing a range of normal variation for the study population, which then may be used as a representative baseline. In another example, during implantation of a PIMD, a clinician may establish individual baselines for individual patients. In yet another example, surface ECG information may be used to establish individual baselines for a patient before implantation of a PIMD.

The method 402 then establishes ranges of orientation 406 during SVT events. For example, an orientation outside an established range of normal variation from a clinical trial may serve to differentiate an SVT from a VT. For example, discriminating between supra-ventricular tachycardia and ventricular tachycardia may be accomplished by detecting about a 45 degree phase change of a cardiac signal vector representative of a ventricular tachycardia relative to a cardiac signal vector representative of a supra-ventricular tachycardia.

A PIMD utilizing the method 402 may detect a tachycardia 408. If the tachycardia 408 is detected, a vector orientation determination 412 is performed, and a change in axis shift may be found, such as a change in the angle of the cardiac activation sequence axis relative to the baseline 404. If the axis shift is determined to be in the established SVT range of orientation 406, then an SVT condition 416 exists. If the axis shift is determined not to be in the established SVT range of orientation 406, then a VT condition 418 exists.

Figure 6D:
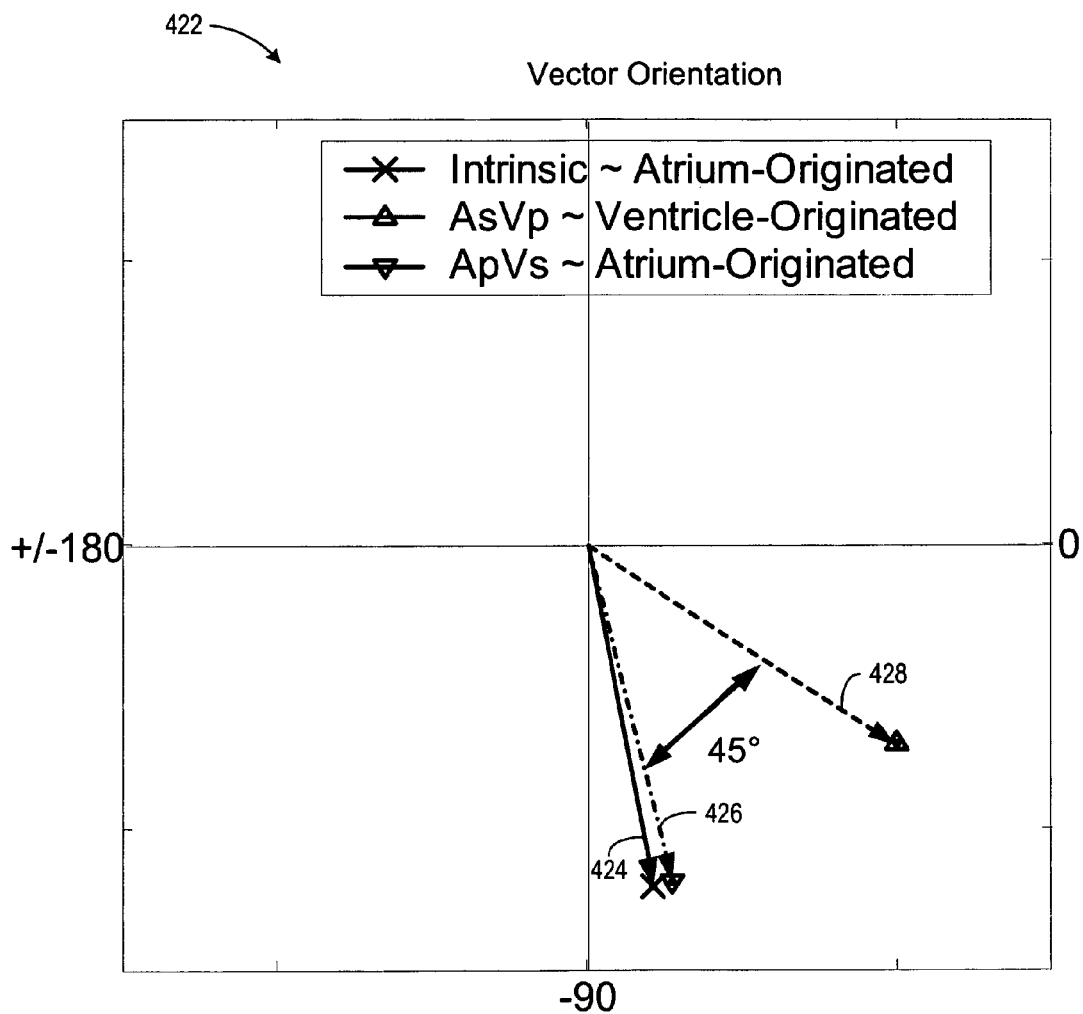
FIG. 6D is a graph of vector angles for an example of cardiac activation sequence orientations showing intrinsic, ventricle originated, and atrium originated orientations.

Referring now to FIG. 6D, a graph 422 illustrating vector angles for cardiac activation sequence orientations of intrinsic, ventricle originated, and atrium originated orientations demonstrates the significant departure of ventricle originated activation sequences from atrium originated activation sequences. The graph 422 follows the same axes conventions as FIGS. 2 and 3A.

An intrinsic atrium-originated activation sequence vector 424 and an atrial paced/ventricular sensed activation sequence vector 426 both lie approximately 45 degrees from an atrial sensed/ventricular paced activation sequence vector 428. The intrinsic atrium-originated activation sequence vector 424 and the atrial paced/ventricular sensed activation sequence vector 426 lie at approximately 80 degrees in the graph 422. The atrial sensed/ventricular paced activation sequence vector 428 lies at approximately 35 degrees in the graph 422. This difference is readily detected using activation sequence monitoring and tracking.

Figure 6E:
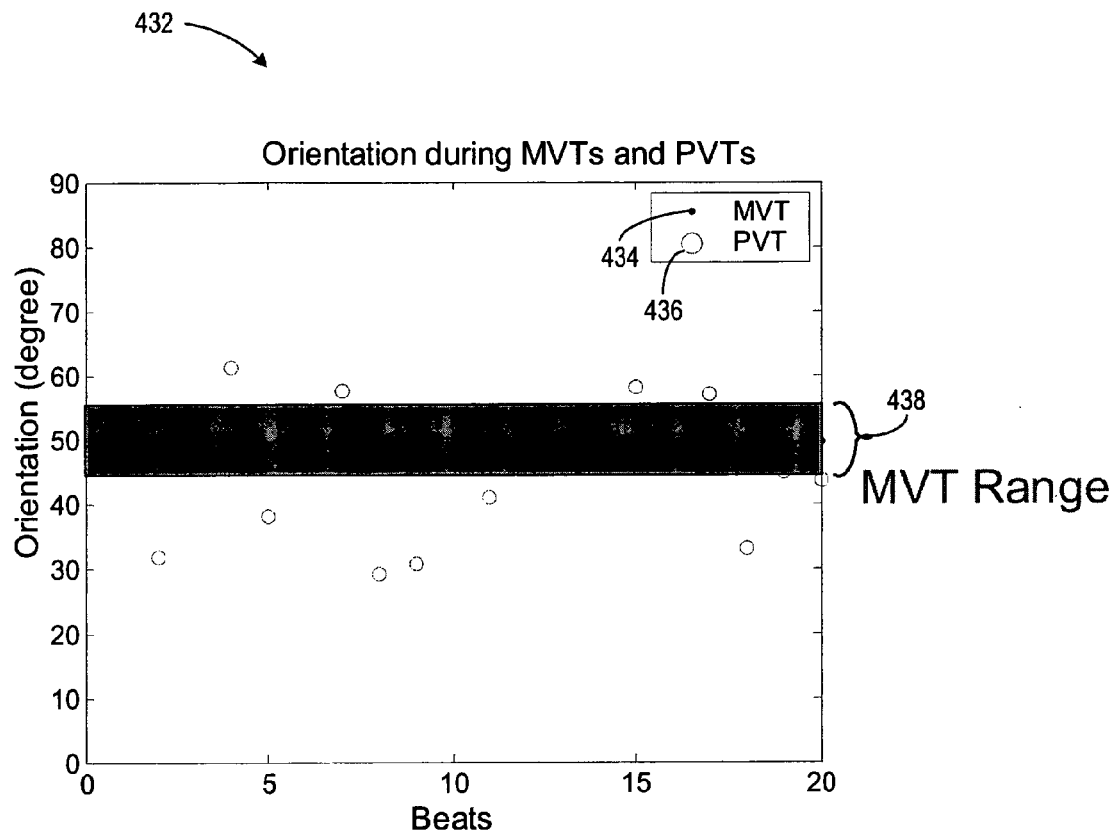
FIG. 6E is a graph illustrating the variance of activation sequence vector angles during monomorphic ventricular tachycardia (MVT) and polymorphic ventricular tachycardia (PVT)

FIG. 6E is a graph 432 illustrating the variance of activation sequence vector angles during monomorphic ventricular tachycardia (MVT) and polymorphic ventricular tachycardia (PVT). The graph 432 has 20 consecutive heartbeats indicated on its abscissa, and orientation of the activation sequence vector, in degrees, on its ordinate. The data depicted in the graph 432 was randomly generated for illustrative purposes. Each point on the graph indicates the dominant orientation vector angle for 20 consecutive beats of a hypothetical MVT condition 434 or a hypothetical PVT condition 436. Data for the MVT condition 434 is seen to lie within a variance range 438. A PVT condition may produce a variance in the range of orientation angle significantly larger than the variance range 438, as is illustrated in the graph of FIG. 6E.

Figure 6F:
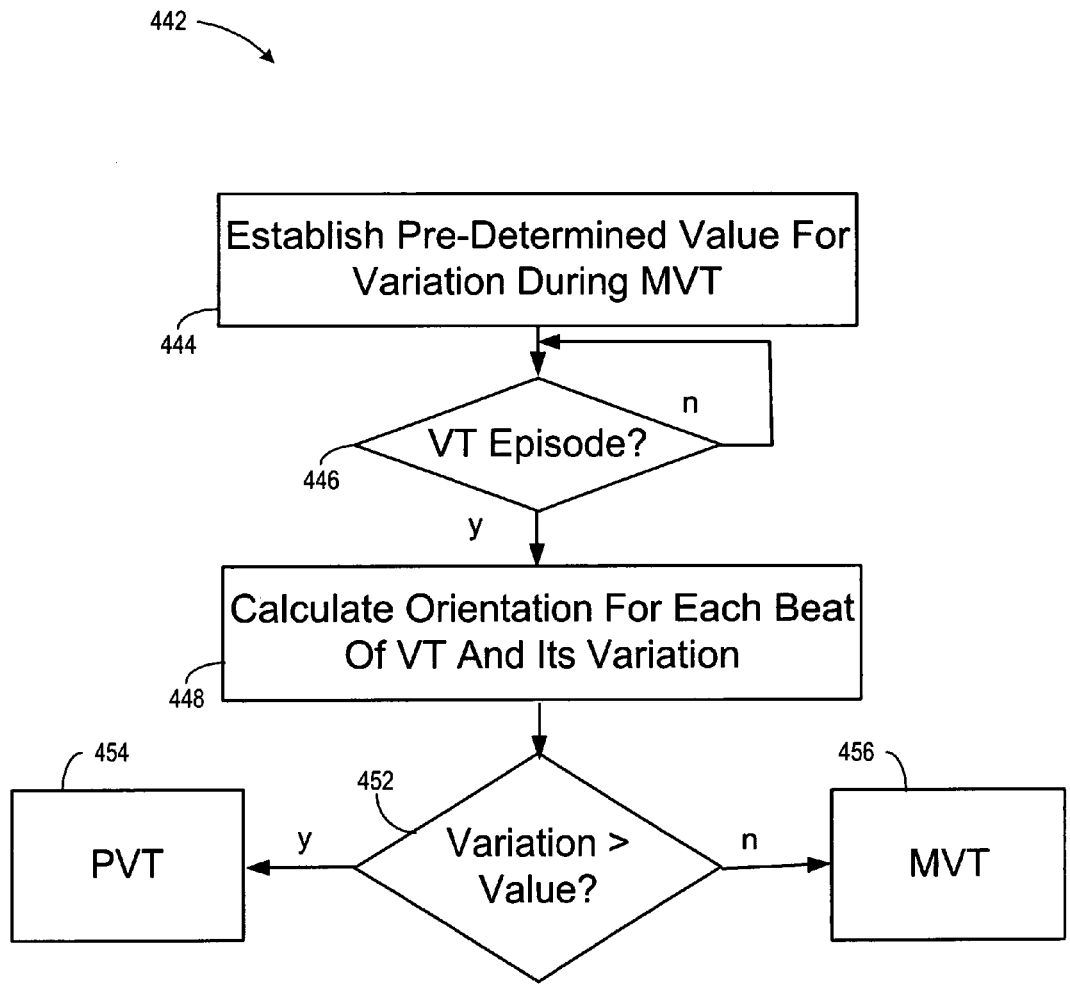
FIG. 6F is a flow chart of a method of differentiating MVT from PVT in accordance with the present invention.

FIG. 6F is a flow chart of a method 442 of differentiating MVT from PVT in accordance with the present invention. The method 442 establishes one or more pre-determined values for MVT, such as by using clinical data or using baselining as was previously described. If VT is detected at detection block 446, a vector orientation calculation 448 is performed for several consecutive beats until a variance is determined. A comparison 452 determines if the variance is greater than the pre-determined value(s) 444. If the variance is greater than the pre-determined value(s) 444, a PVT condition 454 exists. If the variance is less than the pre-determined value(s) 444, a MVT condition 456 exists.

Figure 6G:
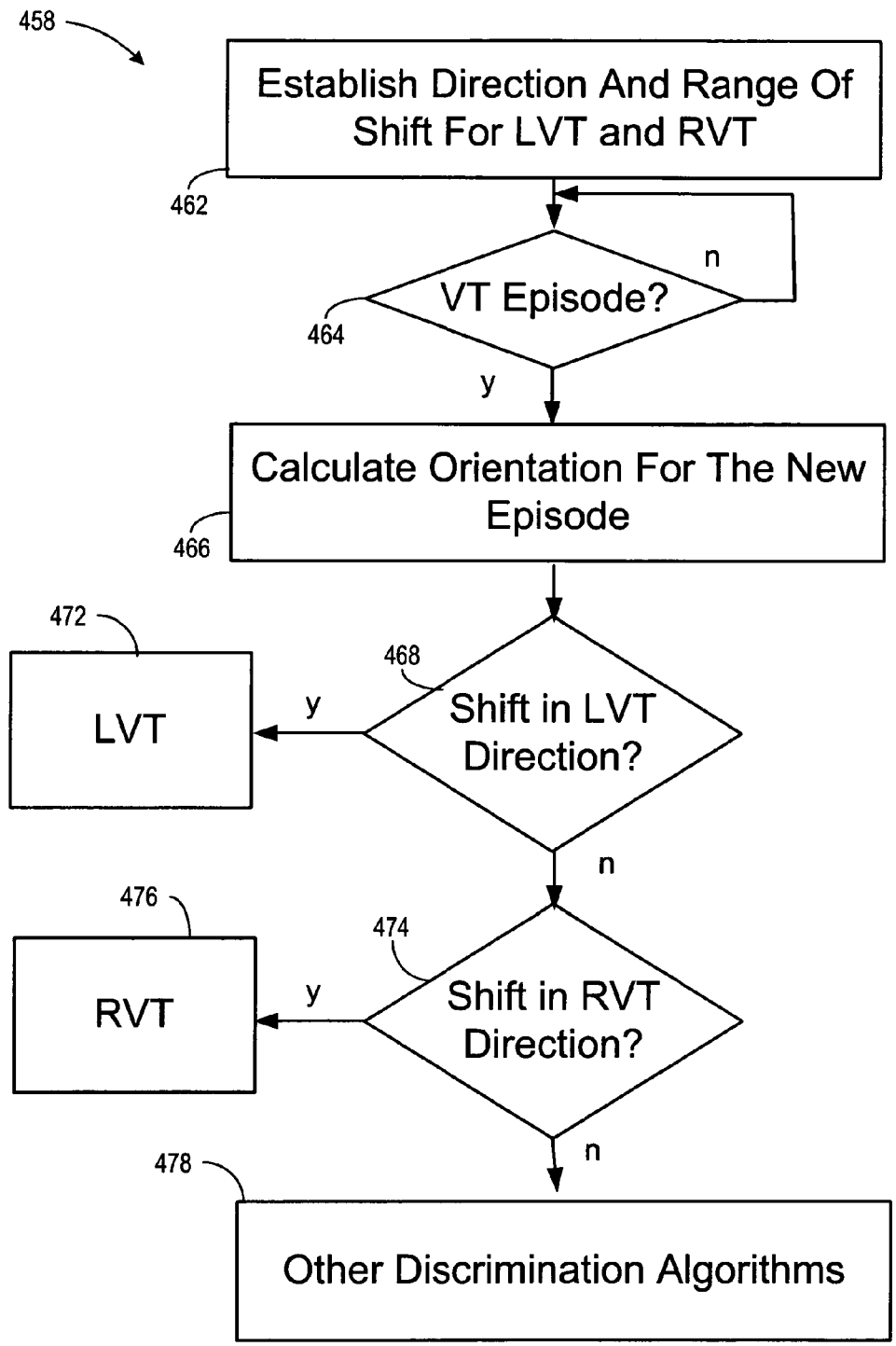
FIG. 6G is a flow chart of a method of differentiating left ventricular tachycardia (LVT) from right ventricular tachycardia (RVT) in accordance with the present invention.

FIG. 6G is a flow chart of a method 458 of differentiating left ventricular tachycardia (LVT) from right ventricular tachycardia (RVT) in accordance with the present invention. The method 458 establishes a direction and range of shift 462 for LVT and RVT regarding cardiac activation sequence vector information. For example, the direction and range of shift 462 for LVT and RVT may be established using clinical trials, providing a range of normal variation for the study population, which may then be used as a representative baseline. In another example, during implantation of a PIMD, a clinician may establish individual directions and ranges of shift 462 of LVT and RVT for individual patients. In yet another example, surface ECG information may be used to establish individual baselines for a patient before implantation of a PIMD.

A PIMD utilizing the method 458 may detect a ventricular tachycardia 464. If the ventricular tachycardia 464 is detected, an orientation for the new vector is calculated 466. A comparison 468 to the directions and ranges of shift 462 of LVT is made, and if the axis shift is determined to be in the LVT direction, then an LVT condition 472 exists. A comparison 474 to the directions and ranges of shift 462 of RVT is made, and if the axis shift is determined to be in the RVT direction, then an RVT condition 476 exists. If no shifts in the LVT or RVT directions are observed, then other discrimination algorithms 478 may be used to discriminate arrhythmias, such as other discrimination methods of the present invention.

Figure 7:
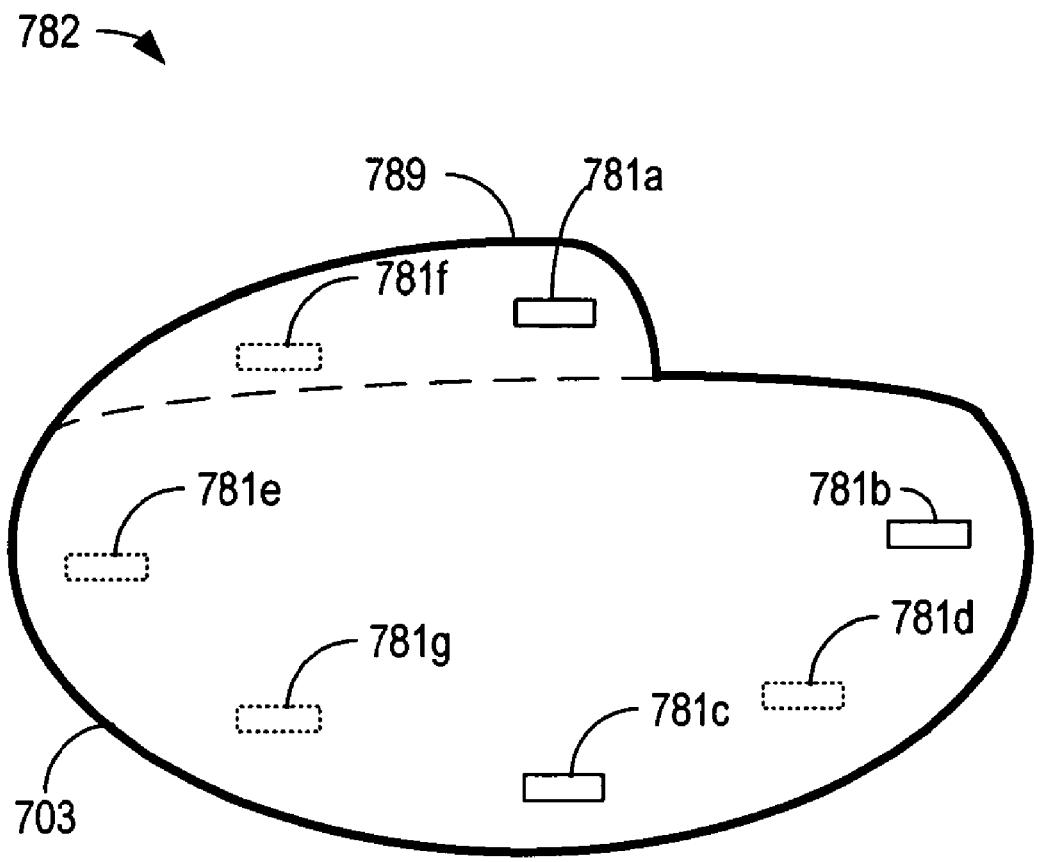
FIG. 7 is a top view of an implantable cardiac device in accordance with the present invention, having at least three electrodes.

FIG. 7 is a top view of a PIMD 782 in accordance with the present invention, having at least three electrodes. Although multiple electrodes are illustrated in FIG. 7 as located on the can, typically the can includes one electrode, and other electrodes are coupled to the can using a lead. The PIMD 782 shown in the embodiment illustrated in FIG. 7 includes a first electrode 781a, a second electrode 781b, and a third electrode 781c provided with a can 703. The PIMD 782 detects and records cardiac activity. The can 703 is illustrated as incorporating a header 789 that may be configured to facilitate removable attachment between one or more leads and the can 703. The can 703 may include any number of electrodes positioned anywhere in or on the can 703, such as optional electrodes 781d, 781e, 781f, and 781g. Each electrode pair provides one vector available for the sensing of ECG signals.

Figure 8:
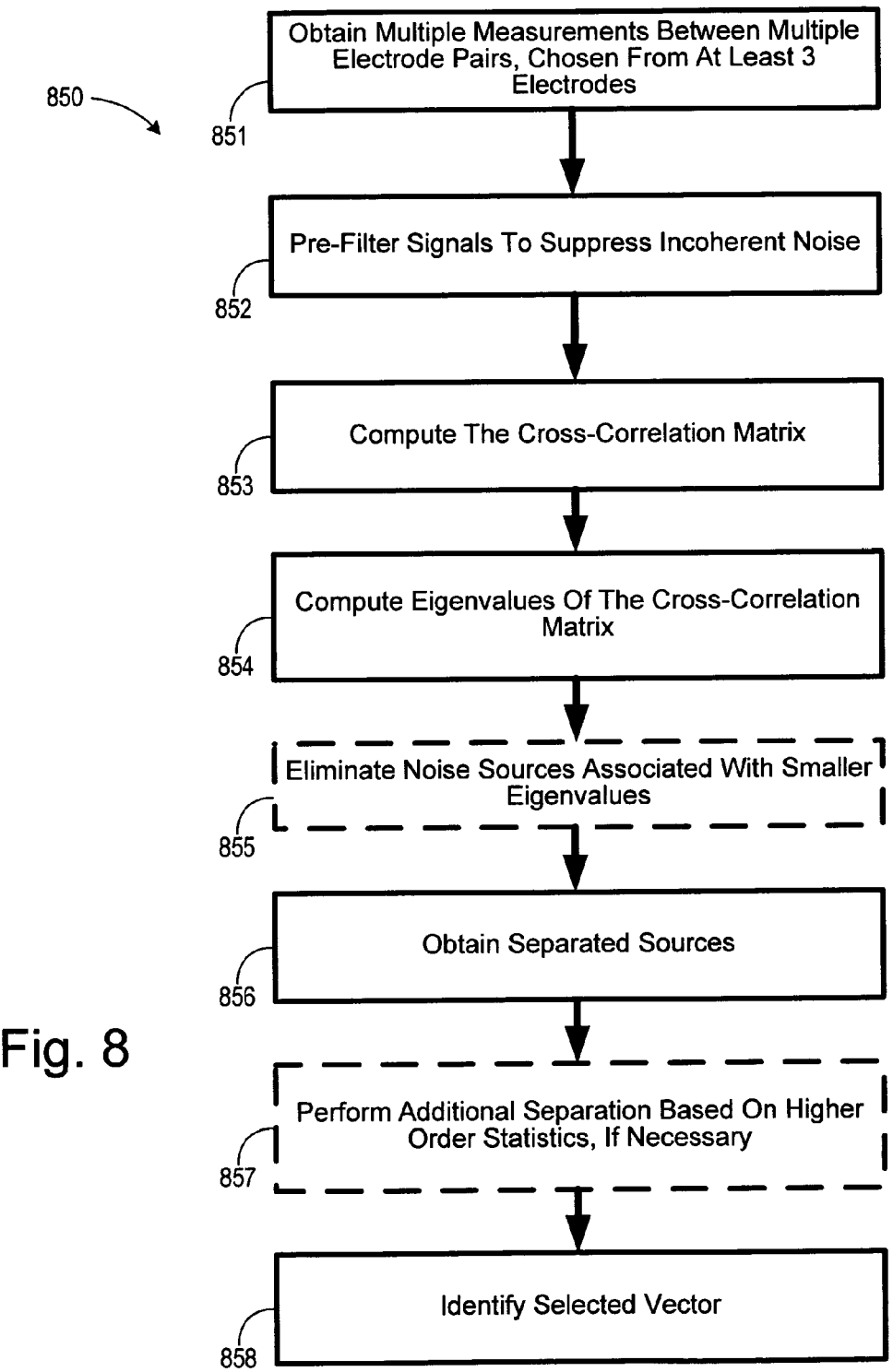
FIG. 8 is a block diagram of a cardiac activation sequence monitoring and/or tracking process in accordance with the present invention.

FIG. 8 is a block diagram of a process 850 useful for extracting vector information for cardiac activation sequence monitoring and tracking in accordance with the present invention. The process 850 starts at block 851, where multiple concurrent measurements are obtained between multiple respective electrode pairs, chosen from at least three electrodes. Block 852 provides for pre-filtering the collected signals with, for example, a linear-phase filter to suppress broadly incoherent noise, and to generally maximize the signal-to-noise ratio.

Block 853 indicates the computation of the cross-correlation matrix, which may be averaged over a relatively short time interval, such as about 1 second. This block enhances the components that are mutually correlated. Block 854 is then provided for computation of the eigenvalues of the cross-correlation matrix. The smaller eigenvalues, normally associated with noise, may then be used at block 855 to eliminate noise, by removing the noise components of the composite signals associated with those eigenvalues.

At block 856, signals may be separated from the composite signals using the eigenvalues. Separated sources may be obtained by taking linear combinations of the recorded signals, as specified in the eigenvectors corresponding to the larger eigenvalues. Optionally, block 857 provides for performing additional separation based on higher order statistics, if the cardiac signal or other signal of interest is not found among the signals separated at block 856.

At block 858, the cardiac signal may be identified based on the selection criteria, along with its associated vector, among the separated signals. Typically, the cardiac signal is found among the signals associated with the largest eigenvalues. Vector selection and updating systems and methods are further described in commonly assigned co-pending U.S. Pat. No. 7,706,866, which is hereby incorporated herein by reference.

For purposes of illustration, and not of limitation, various embodiments of devices that may use cardiac activation sequence monitoring and tracking for arrhythmia discrimination in accordance with the present invention are described herein in the context of PIMD's that may be implanted under the skin in the chest region of a patient. A PIMD may, for example, be implanted subcutaneously such that all or selected elements of the device are positioned on the patient's front, back, side, or other body locations suitable for monitoring cardiac activity and/or delivering cardiac stimulation therapy. It is understood that elements of the PIMD may be located at several different body locations, such as in the chest, abdominal, or subclavian region with electrode elements respectively positioned at different regions near, around, in, or on the heart.

The primary housing (e.g., the active or non-active can) of the PIMD, for example, may be configured for positioning outside of the rib cage at an intercostal or subcostal location, within the abdomen, or in the upper chest region (e.g., subclavian location, such as above the third rib). In one implementation, one or more leads incorporating electrodes may be located in direct contact with the heart, great vessel or coronary vasculature, such as via one or more leads implanted by use of conventional transvenous delivery approaches. In another implementation, one or more electrodes may be located on the primary housing and/or at other locations about, but not in direct contact with the heart, great vessel or coronary vasculature.

In a further implementation, for example, one or more electrode subsystems or electrode arrays may be used to sense cardiac activity and/or deliver cardiac stimulation energy in a PIMD configuration employing an active can or a configuration employing a non-active can. Electrodes may be situated at anterior and/or posterior locations relative to the heart. Examples of useful electrode locations and features that may be incorporated in various embodiments of the present invention are described in commonly owned, co-pending US Patent Publication No. 20040230230; and U.S. Pat. Nos. 7,299,086; and 17,499,750, which are hereby incorporated herein by reference.

Certain configurations illustrated herein are generally described as capable of implementing various functions traditionally performed by an implantable cardioverter/defibrillator (ICD), and may operate in numerous cardioversion/defibrillation modes as are known in the art. Examples of ICD circuitry, structures and functionality, aspects of which may be incorporated in a PIMD of a type that may benefit from cardiac activation sequence monitoring and/or tracking are disclosed in commonly owned U.S. Pat. Nos. 5,133,353; 5,179,945; 5,314,459; 5,318,597; 5,620,466; and 5,662,688, which are hereby incorporated herein by reference.

In particular configurations, systems and methods may perform functions traditionally performed by pacemakers, such as providing various pacing therapies as are known in the art, in addition to cardioversion/defibrillation therapies. Examples of pacemaker circuitry, structures and functionality, aspects of which may be incorporated in a PIMD of a type that may benefit from cardiac activation sequence monitoring and/or tracking methods and implementations are disclosed in commonly owned U.S. Pat. Nos. 4,562,841; 5,284,136; 5,376,106; 5,036,849; 5,540,727; 5,836,987; 6,044,298; and 6,055,454, which are hereby incorporated herein by reference. It is understood that PIMD configurations may provide for non-physiologic pacing support in addition to, or to the exclusion of, bradycardia and/or anti-tachycardia pacing therapies.

A PIMD useful for extracting vector information for cardiac activation sequence monitoring and tracking in accordance with the present invention may implement diagnostic and/or monitoring functions as well as provide cardiac stimulation therapy. Examples of cardiac monitoring circuitry, structures and functionality, aspects of which may be incorporated in a PIMD of a type that may benefit from cardiac activation sequence monitoring and/or tracking methods and implementations are disclosed in commonly owned U.S. Pat. Nos. 5,313,953; 5,388,578; and 5,411,031, which are hereby incorporated herein by reference.

Various embodiments described herein may be used in connection with congestive heart failure (CHF) monitoring, diagnosis, and/or therapy. A PIMD of the present invention may incorporate CHF features involving dual-chamber or bi-ventricular pacing therapy, cardiac resynchronization therapy, cardiac function optimization, or other CHF related methodologies. For example, any PIMD of the present invention may incorporate features of one or more of the following references: commonly owned U.S. Pat. Nos. 6,411,848; 6,285,907; 4,928,688; 6,459,929; 5,334,222; 6,026,320; 6,371,922; 6,597,951; 6,424,865; 6,542,775; and 7,260,432, each of which is hereby incorporated herein by reference.

A PIMD may be used to implement various diagnostic functions, which may involve performing rate-based, pattern and rate-based, and/or morphological tachyarrhythmia discrimination analyses. Subcutaneous, cutaneous, and/or external sensors may be employed to acquire physiologic and non-physiologic information for purposes of enhancing tachyarrhythmia detection and termination. It is understood that configurations, features, and combination of features described in the present disclosure may be implemented in a wide range of implantable medical devices, and that such embodiments and features are not limited to the particular devices described herein.

Figure 9:
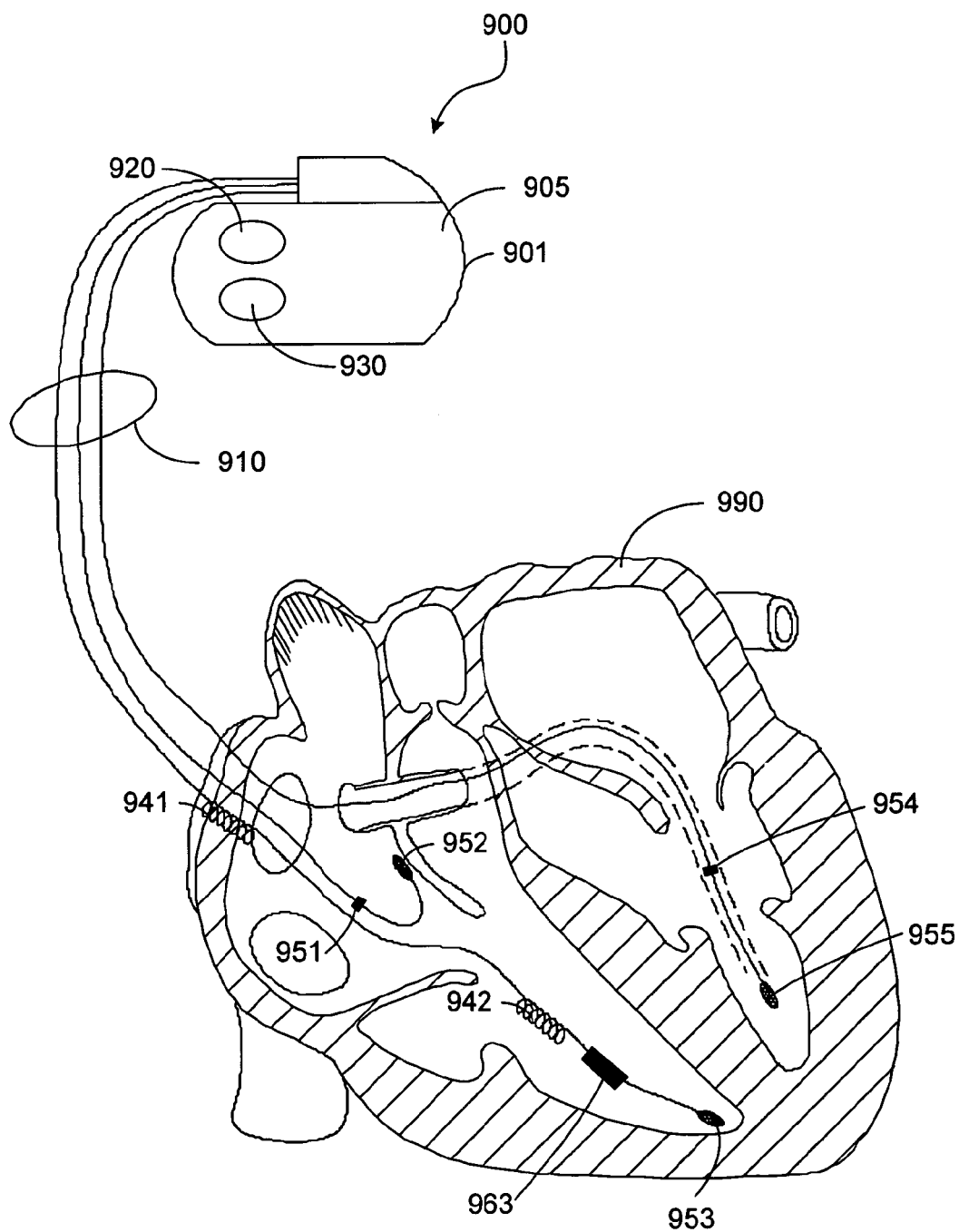
FIG. 9 is an illustration of an implantable cardiac device including a lead assembly shown implanted in a sectional view of a heart, in accordance with embodiments of the invention.

Referring now to FIG. 9, the implantable device illustrated in FIG. 9 is an embodiment of a PIMD that may benefit from cardiac sequence monitoring and tracking in accordance with the present invention. In this example, the implantable device includes a cardiac rhythm management device (CRM) 900 including an implantable pulse generator 905 electrically and physically coupled to an intracardiac lead system 910.

Portions of the intracardiac lead system 910 are inserted into the patient's heart 990. The intracardiac lead system 910 includes one or more electrodes configured to sense electrical cardiac activity of the heart, deliver electrical stimulation to the heart, sense the patient's transthoracic impedance, and/or sense other physiological parameters, e.g., cardiac chamber pressure or temperature. Portions of the housing 901 of the pulse generator 905 may optionally serve as a can electrode.

Communications circuitry is disposed within the housing 901 for facilitating communication between the pulse generator 905 and an external communication device, such as a portable or bed-side communication station, patient-carried/worn communication station, or external programmer, for example. The communications circuitry may also facilitate unidirectional or bidirectional communication with one or more implanted, external, cutaneous, or subcutaneous physiologic or non-physiologic sensors, patient-input devices and/or information systems.

The pulse generator 905 may optionally incorporate a motion detector 920 that may be used to sense patient activity as well as various respiratory and cardiac related conditions. For example, the motion detector 920 may be optionally configured to sense snoring, activity level, and/or chest wall movements associated with respiratory effort, for example. The motion detector 920 may be implemented as an accelerometer positioned in or on the housing 901 of the pulse generator 905. If the motion sensor is implemented as an accelerometer, the motion sensor may also provide respiratory, e.g. rales, coughing, and cardiac, e.g. S1-S4 heart sounds, murmurs, and other acoustic information.

The lead system 910 and pulse generator 905 of the CRM 900 may incorporate one or more transthoracic impedance sensors that may be used to acquire the patient's respiratory waveform, or other respiratory-related information. The transthoracic impedance sensor may include, for example, one or more intracardiac electrodes 941, 942, 951-955, 963 positioned in one or more chambers of the heart 990. The intracardiac electrodes 941, 942, 951-955, 963 may be coupled to impedance drive/sense circuitry 930 positioned within the housing of the pulse generator 905.

In one implementation, impedance drive/sense circuitry 930 generates a current that flows through the tissue between an impedance drive electrode 951 and a can electrode on the housing 901 of the pulse generator 905. The voltage at an impedance sense electrode 952 relative to the can electrode changes as the patient's transthoracic impedance changes. The voltage signal developed between the impedance sense electrode 952 and the can electrode is detected by the impedance sense circuitry 930. Other locations and/or combinations of impedance sense and drive electrodes are also possible.

The lead system 910 may include one or more cardiac pace/sense electrodes 951-955 positioned in, on, or about one or more heart chambers for sensing electrical signals from the patient's heart 990 and/or delivering pacing pulses to the heart 990. The intracardiac sense/pace electrodes 951-955, such as those illustrated in FIG. 9, may be used to sense and/or pace one or more chambers of the heart, including the left ventricle, the right ventricle, the left atrium and/or the right atrium. The lead system 910 may include one or more defibrillation electrodes 941, 942 for delivering defibrillation/cardioversion shocks to the heart.

The pulse generator 905 may include circuitry for detecting cardiac arrhythmias and/or for controlling pacing or defibrillation therapy in the form of electrical stimulation pulses or shocks delivered to the heart through the lead system 910. The pulse generator 905 may also incorporate circuitry, structures and functionality of the implantable medical devices disclosed in commonly owned U.S. Pat. Nos. 5,203, 348; 5,230,337; 5,360,442; 5,366,496; 5,397,342; 5,391,200; 5,545,202; 5,603,732; and 5,916,243; 6,360,127; 6,597,951; and 6,993,389, which are hereby incorporated herein by reference.

Figure 10:
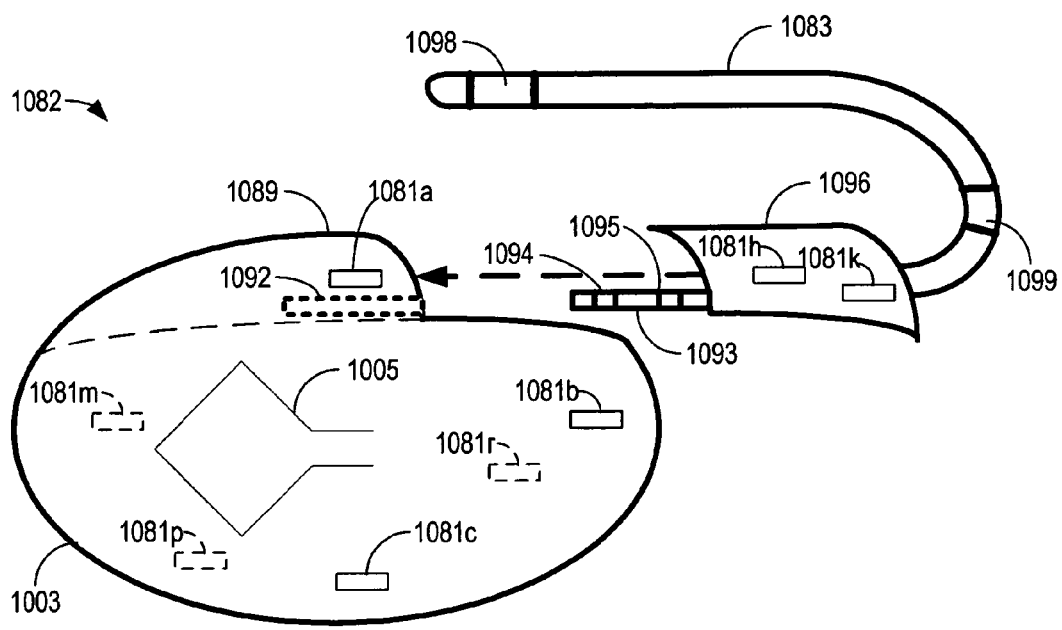
FIG. 10 is a top view of an implantable cardiac device in accordance with the present invention, including an antenna electrode and a lead/header arrangement.

FIG. 10 is a top view of a PIMD 1082 in accordance with the present invention, having at least three electrodes. One electrode is illustrated as an antenna 1005 of the PIMD that may also be used for radio-frequency (RF) communications. The PIMD 1082 shown in the embodiment illustrated in FIG. 10 includes a first electrode 1098 and a second electrode 1099 coupled to a can 1003 through a header 1089, via an electrode module 1096. The first electrode 1098 and second electrode 1099 may be located on a lead 1083 (single or multiple lead, or electrode array), or may be located directly in or on the electrode module 1096.

The PIMD 1082 detects and records cardiac activity. The can 1003 is illustrated as incorporating the header 1089. The header 1089 may be configured to facilitate removable attachment between an electrode module 1096 and the can 1003, as is shown in the embodiment depicted in FIG. 10. The header 1089 includes a female coupler 1092 configured to accept a male coupler 1093 from the electrode module 1096. The male coupler 1093 is shown having two electrode contacts 1094, 1095 for coupling one or more electrodes 1098, 1099 through the electrode module 1096 to the can 1003. An electrode 1081$h$ and an electrode 1081$k$ are illustrated on the header 1089 of the can 1003 and may also be coupled through the electrode module 1096 to the can 1003. The can 1003 may alternatively, or in addition to the header electrodes 1081$h$, 1081$k$ and/or first and second electrodes 1098, 1099, include one or more can electrodes 1081$a$, 1081$b$, 1081$c$.

Recording and monitoring systems and methods that may benefit from cardiac activation sequence monitoring and tracking in accordance with the present invention are further described in commonly assigned co-pending US Patent Publication No. 20050004615 hereby incorporated herein by reference.

Electrodes may also be provided on the back of the can 1003, typically the side facing externally relative to the patient after implantation. For example, electrodes 1081$m$, 1081$p$, and 1081$r$ are illustrated as positioned in or on the back of the can 1003. Providing electrodes on both front and back surfaces of the can 1003 provides for a three-dimensional spatial distribution of the electrodes, which may provide additional discrimination capabilities for cardiac activation sequence monitoring and tracking in accordance with the present invention. Further description of three-dimensional configurations are described in U.S. Pat. No. 7,299,086, previously incorporated by reference.

In this and other configurations, the header 1089 incorporates interface features (e.g., electrical connectors, ports, engagement features, and the like) that facilitate electrical connectivity with one or more lead and/or sensor systems, lead and/or sensor modules, and electrodes. The header 1089 may also incorporate one or more electrodes in addition to, or instead of, the electrodes provided by the lead 1083, such as electrodes 1081$h$ and 1081$k$, to provide more available vectors to the PIMD. The interface features of the header 1089 may be protected from body fluids using known techniques.

The PIMD 1082 may further include one or more sensors in or on the can 1003, header 1089, electrode module 1096, or lead(s) that couple to the header 1089 or electrode module 1096. Useful sensors may include electrophysiologic and non-electrophysiologic sensors, such as an acoustic sensor, an impedance sensor, a blood sensor, such as an oxygen saturation sensor (oximeter or plethysmographic sensor), a blood pressure sensor, minute ventilation sensor, or other sensor described or incorporated herein.

Figure 11:
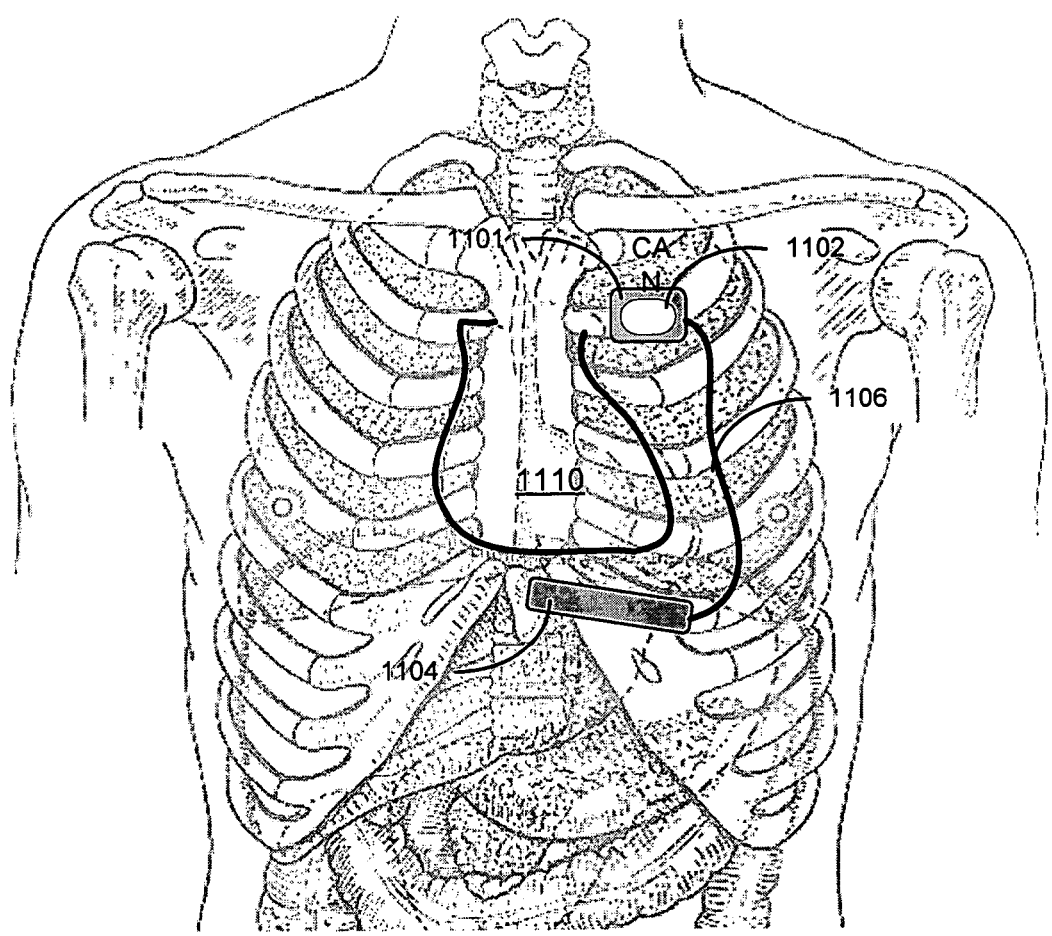
FIG. 11 is a diagram illustrating components of a cardiac monitoring and/or stimulation device including an electrode array in accordance with an embodiment of the present invention.

In one configuration, as is illustrated in FIG. 11, electrode subsystems of a PIMD system are arranged about a patient's heart 1110. The PIMD system includes a first electrode subsystem, including a can electrode 1102, and a second electrode subsystem 1104 that includes at least two electrodes or at least one multi-element electrode. The second electrode subsystem 1104 may include a number of electrodes used for sensing and/or electrical stimulation and is connected to pulse generator 905 via lead 1106.

In various configurations, the second electrode subsystem 1104 may include a combination of electrodes. The combination of electrodes of the second electrode subsystem 1104 may include coil electrodes, tip electrodes, ring electrodes, multi-element coils, spiral coils, spiral coils mounted on non-conductive backing, screen patch electrodes, and other electrode configurations as will be described below. A suitable non-conductive backing material is silicone rubber, for example.

The can electrode 1102 is positioned on the housing 1101 that encloses the PIMD electronics. In one embodiment, the can electrode 1102 includes the entirety of the external surface of housing 1101. In other embodiments, various portions of the housing 1101 may be electrically isolated from the can electrode 1102 or from tissue. For example, the active area of the can electrode 1102 may include all or a portion of either the anterior or posterior surface of the housing 1101 to direct current flow in a manner advantageous for cardiac sensing and/or stimulation.

Portions of the housing may be electrically isolated from tissue to optimally direct current flow. For example, portions of the housing 1101 may be covered with a non-conductive, or otherwise electrically resistive, material to direct current flow. Suitable non-conductive material coatings include those formed from silicone rubber, polyurethane, or parylene, for example.

Figure 12:
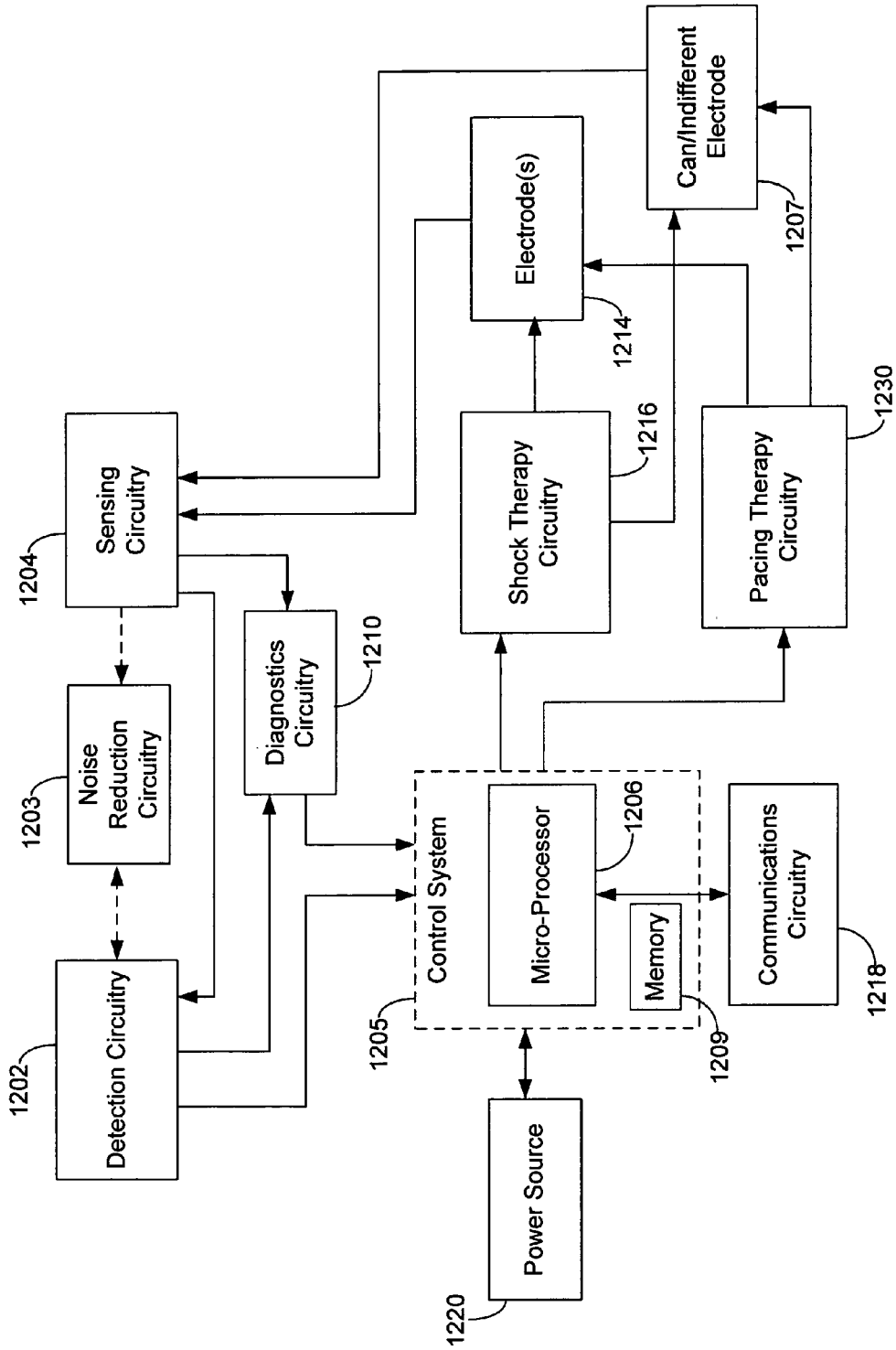
FIG. 12 is a block diagram illustrating various components of a cardiac monitoring and/or stimulation device in accordance with an embodiment of the present invention.

FIG. 12 is a block diagram depicting various componentry of different arrangements of a PIMD in accordance with embodiments of the present invention. The components, functionality, and configurations depicted in FIG. 12 are intended to provide an understanding of various features and combinations of features that may be incorporated in a PIMD. It is understood that a wide variety of device configurations are contemplated, ranging from relatively sophisticated to relatively simple designs. As such, particular PIMD configurations may include some componentry illustrated in FIG. 12, while excluding other componentry illustrated in FIG. 12.

Illustrated in FIG. 12 is a processor-based control system 1205 which includes a micro-processor 1206 coupled to appropriate memory (volatile and/or non-volatile) 1209, it being understood that any logic-based control architecture may be used. The control system 1205 is coupled to circuitry and components to sense, detect, and analyze electrical signals produced by the heart and deliver electrical stimulation energy to the heart under predetermined conditions to treat cardiac arrhythmias and/or other cardiac conditions. The control system 1205 and associated components also provide pacing therapy to the heart. The electrical energy delivered by the PIMD may be in the form of low energy pacing pulses or high-energy pulses for cardioversion or defibrillation.

Cardiac signals are sensed using the electrode(s) 1214 and the can or indifferent electrode 1207 provided on the PIMD housing. Cardiac signals may also be sensed using only the electrode(s) 1214, such as in a non-active can configuration. As such, unipolar, bipolar, or combined unipolar/bipolar electrode configurations as well as multi-element electrodes and combinations of noise canceling and standard electrodes may be employed. The sensed cardiac signals are received by sensing circuitry 1204, which includes sense amplification circuitry and may also include filtering circuitry and an analog-to-digital (A/D) converter. The sensed cardiac signals processed by the sensing circuitry 1204 may be received by noise reduction circuitry 1203, which may further reduce noise before signals are sent to the detection circuitry 1202.

Noise reduction circuitry 1203 may also be incorporated after sensing circuitry 1204 in cases where high power or computationally intensive noise reduction algorithms are required. The noise reduction circuitry 1203, by way of amplifiers used to perform operations with the electrode signals, may also perform the function of the sensing circuitry 1204. Combining the functions of sensing circuitry 1204 and noise reduction circuitry 1203 may be useful to minimize the necessary componentry and lower the power requirements of the system.

In the illustrative configuration shown in FIG. 12, the detection circuitry 1202 is coupled to, or otherwise incorporates, noise reduction circuitry 1203. The noise reduction circuitry 1203 operates to improve the SNR of sensed cardiac signals by removing noise content of the sensed cardiac signals introduced from various sources. Typical types of cardiac signal noise includes electrical noise and noise produced from skeletal muscles, for example. A number of methodologies for improving the SNR of sensed cardiac signals in the presence of skeletal muscular induced noise, including signal separation techniques incorporating combinations of electrodes and multi-element electrodes, are described hereinbelow.

Detection circuitry 1202 may include a signal processor that coordinates analysis of the sensed cardiac signals and/or other sensor inputs to detect cardiac arrhythmias, such as, in particular, tachyarrhythmia. Rate based and/or morphological discrimination algorithms may be implemented by the signal processor of the detection circuitry 1202 to detect and verify the presence and severity of an arrhythmic episode. Examples of arrhythmia detection and discrimination circuitry, structures, and techniques, aspects of which may be implemented by a PIMD of a type that may benefit from cardiac activation sequence monitoring and/or tracking methods and implementations are disclosed in commonly owned U.S. Pat. Nos. 5,301,677, 6,438,410, and 6,708,058, which are hereby incorporated herein by reference. Arrhythmia detection methodologies particularly well suited for implementation in cardiac monitoring and/or stimulation systems are described hereinbelow.

The detection circuitry 1202 communicates cardiac signal information to the control system 1205. Memory circuitry 1209 of the control system 1205 contains parameters for operating in various monitoring, defibrillation, and, if applicable, pacing modes, and stores data indicative of cardiac signals received by the detection circuitry 1202. The memory circuitry 1209 may also be configured to store historical ECG and therapy data, which may be used for various purposes and transmitted to an external receiving device as needed or desired.

In certain configurations, the PIMD may include diagnostics circuitry 1210. The diagnostics circuitry 1210 typically receives input signals from the detection circuitry 1202 and the sensing circuitry 1204. The diagnostics circuitry 1210 provides diagnostics data to the control system 1205, it being understood that the control system 1205 may incorporate all or part of the diagnostics circuitry 1210 or its functionality. The control system 1205 may store and use information provided by the diagnostics circuitry 1210 for a variety of diagnostics purposes. This diagnostic information may be stored, for example, subsequent to a triggering event or at predetermined intervals, and may include system diagnostics, such as power source status, therapy delivery history, and/or patient diagnostics. The diagnostic information may take the form of electrical signals or other sensor data acquired immediately prior to therapy delivery.

According to a configuration that provides cardioversion and defibrillation therapies, the control system 1205 processes cardiac signal data received from the detection circuitry 1202 and initiates appropriate tachyarrhythmia therapies to terminate cardiac arrhythmic episodes and return the heart to normal sinus rhythm. The control system 1205 is coupled to shock therapy circuitry 1216. The shock therapy circuitry 1216 is coupled to the electrode(s) 1214 and the can or indifferent electrode 1207 of the PIMD housing.

Upon command, the shock therapy circuitry 1216 delivers cardioversion and defibrillation stimulation energy to the heart in accordance with a selected cardioversion or defibrillation therapy. In a less sophisticated configuration, the shock therapy circuitry 1216 is controlled to deliver defibrillation therapies, in contrast to a configuration that provides for delivery of both cardioversion and defibrillation therapies. Examples of PIMD high energy delivery circuitry, structures and functionality, aspects of which may be incorporated in a PIMD of a type that may benefit from aspects of the present invention are disclosed in commonly owned U.S. Pat. Nos. 5,372,606; 5,411,525; 5,468,254; and 5,634,938, which are hereby incorporated herein by reference.

Arrhythmic episodes may also be detected and verified by morphology-based analysis of sensed cardiac signals as is known in the art. Tiered or parallel arrhythmia discrimination algorithms may also be implemented using both rate-based and morphologic-based approaches. Further, a rate and pattern-based arrhythmia detection and discrimination approach may be employed to detect and/or verify arrhythmic episodes, such as the approach disclosed in U.S. Pat. Nos. 6,487,443; 6,259,947; 6,141,581; 5,855,593; and 5,545,186, which are hereby incorporated herein by reference.

In accordance with another configuration, a PIMD may incorporate a cardiac pacing capability in addition to, or to the exclusion of, cardioversion and/or defibrillation capabilities. As is shown in FIG. 12, the PIMD includes pacing therapy circuitry 1230 that is coupled to the control system 1205 and the electrode(s) 1214 and can/indifferent electrodes 1207. Upon command, the pacing therapy circuitry 1230 delivers pacing pulses to the heart in accordance with a selected pacing therapy.

Control signals, developed in accordance with a pacing regimen by pacemaker circuitry within the control system 1205, are initiated and transmitted to the pacing therapy circuitry 1230 where pacing pulses are generated. A pacing regimen, such as those discussed and incorporated herein, may be modified by the control system 1205. In one particular application, a sense vector optimization approach of the present invention may be implemented to enhance capture detection and/or capture threshold determinations, such as by selecting an optimal vector for sensing an evoked response resulting from application of a capture pacing stimulus.

The PIMD shown in FIG. 12 may be configured to receive signals from one or more physiologic and/or non-physiologic sensors. Depending on the type of sensor employed, signals generated by the sensors may be communicated to transducer circuitry coupled directly to the detection circuitry 1202 or indirectly via the sensing circuitry 1204. It is noted that certain sensors may transmit sense data to the control system 1205 without processing by the detection circuitry 1202.

Communications circuitry 1218 is coupled to the microprocessor 1206 of the control system 1205. The communications circuitry 1218 allows the PIMD to communicate with one or more receiving devices or systems situated external to the PIMD. By way of example, the PIMD may communicate with a patient-worn, portable or bedside communication system via the communications circuitry 1218. In one configuration, one or more physiologic or non-physiologic sensors (subcutaneous, cutaneous, or external of patient) may be equipped with a short-range wireless communication interface, such as an interface conforming to a known communications standard, such as Bluetooth or IEEE 802 standards. Data acquired by such sensors may be communicated to the PIMD via the communications circuitry 1218. It is noted that physiologic or non-physiologic sensors equipped with wireless transmitters or transceivers may communicate with a receiving system external of the patient.

The communications circuitry 1218 allows the PIMD to communicate with an external programmer. In one configuration, the communications circuitry 1218 and the programmer unit (not shown) use a wire loop antenna and a radio frequency telemetric link, as is known in the art, to receive and transmit signals and data between the programmer unit and communications circuitry 1218. In this manner, programming commands and data are transferred between the PIMD and the programmer unit during and after implant. Using a programmer, a physician is able to set or modify various parameters used by the PIMD. For example, a physician may set or modify parameters affecting monitoring, detection, pacing, and defibrillation functions of the PIMD, including pacing and cardioversion/defibrillation therapy modes.

Typically, the PIMD is encased and hermetically sealed in a housing suitable for implanting in a human body as is known in the art. Power to the PIMD is supplied by an electrochemical power source 1220 housed within the PIMD. In one configuration, the power source 1220 includes a rechargeable battery. According to this configuration, charging circuitry is coupled to the power source 1220 to facilitate repeated non-invasive charging of the power source 1220. The communications circuitry 1218, or separate receiver circuitry, is configured to receive RF energy transmitted by an external RF energy transmitter. The PIMD may, in addition to a rechargeable power source, include a non-rechargeable battery. It is understood that a rechargeable power source need not be used, in which case a long-life non-rechargeable battery is employed.

The detection circuitry 1202, which is coupled to a microprocessor 1206, may be configured to incorporate, or communicate with, specialized circuitry for processing sensed cardiac signals in manners particularly useful in a cardiac sensing and/or stimulation device. As is shown by way of example in FIG. 12, the detection circuitry 1202 may receive information from multiple physiologic and non-physiologic sensors.

The detection circuitry 1202 may also receive information from one or more sensors that monitor skeletal muscle activity. In addition to cardiac activity signals, electrodes readily detect skeletal muscle signals. Such skeletal muscle signals may be used to determine the activity level of the patient. In the context of cardiac signal detection, such skeletal muscle signals are considered artifacts of the cardiac activity signal, which may be viewed as noise.

The components, functionality, and structural configurations depicted herein are intended to provide an understanding of various features and combination of features that may be incorporated in a PIMD. It is understood that a wide variety of PIMDs and other implantable cardiac monitoring and/or stimulation device configurations are contemplated, ranging from relatively sophisticated to relatively simple designs. As such, particular PIMD or cardiac monitoring and/or stimulation device configurations may include particular features as described herein, while other such device configurations may exclude particular features described herein.

The PIMD may detect a variety of physiological signals that may be used in connection with various diagnostic, therapeutic or monitoring implementations. For example, the PIMD may include sensors or circuitry for detecting respiratory system signals, cardiac system signals, and signals related to patient activity. In one embodiment, the PIMD senses intrathoracic impedance, from which various respiratory parameters may be derived, including, for example, respiratory tidal volume and minute ventilation. Sensors and associated circuitry may be incorporated in connection with a PIMD for detecting one or more body movement or body posture or position related signals. For example, accelerometers and GPS devices may be employed to detect patient activity, patient location, body orientation, or torso position.

Figure 13:
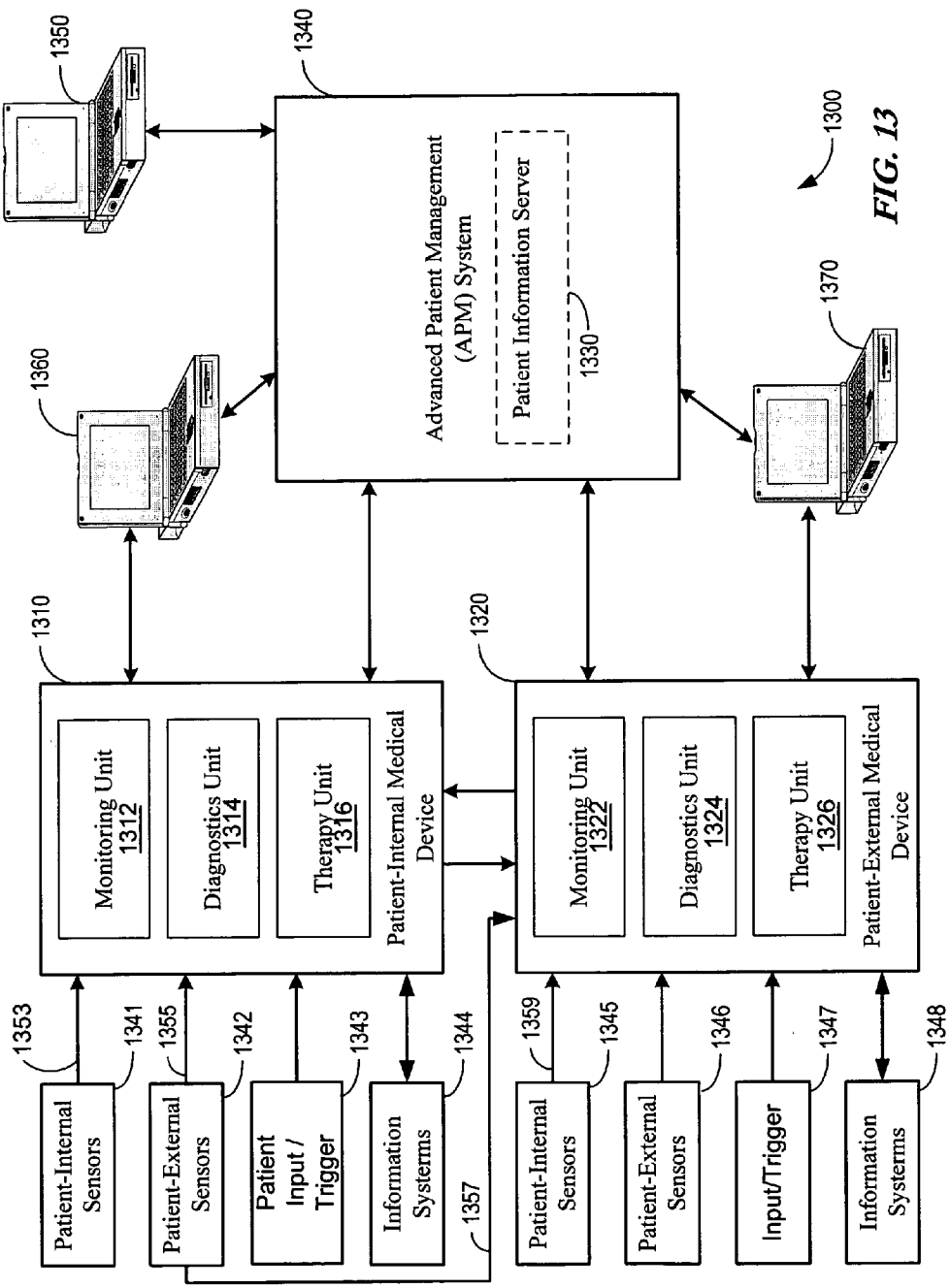
FIG. 13 is a block diagram of a medical system that may be used to implement system updating, coordinated patient monitoring, diagnosis, and/or therapy in accordance with embodiments of the present invention.

Referring now to FIG. 13, a PIMD of the present invention may be used within the structure of an advanced patient management (APM) system 1300. The APM system 1300 allows physicians and/or other clinicians to remotely and automatically monitor cardiac and respiratory functions, as well as other patient conditions. The APM system 1300 may also be used to provide information to the PIMD for incorporation into templates, such as medication information or other patient information useful in accordance with the present invention. The APM system 1300 may also be used to select portions of cardiac waveforms for which templates are desired. The APM system 1300 may also be used to select or eliminate therapies associate with templates. In one example, a PIMD implemented as a cardiac pacemaker, defibrillator, or resynchronization device may be equipped with various telecommunications and information technologies that enable real-time data collection, diagnosis, and treatment of the patient.

Various PIMD embodiments described herein may be used in connection with advanced patient management. Methods, structures, and/or techniques described herein, which may be adapted to provide for remote patient/device monitoring, diagnosis, therapy, or other APM related methodologies, may incorporate features of one or more of the following references: U.S. Pat. Nos. 6,221,011; 6,270,457; 6,277,072; 6,280,380; 6,312,378; 6,336,903; 6,358,203; 6,368,284; 6,398,728; and 6,440,066, which are hereby incorporated herein by reference.

As is illustrated in FIG. 13, the medical system 1300 may be used to implement template generation, template updating, template initialization, template selection, patient measuring, patient monitoring, patient diagnosis, patient therapy, therapy selection, and/or therapy elimination in accordance with embodiments of the invention. The medical system 1300 may include, for example, one or more patient-internal medical devices 1310, such as a PIMD, and one or more patient-external medical devices 1320, such as a monitor or signal display device. Each of the patient-internal 1310 and patient-external 1320 medical devices may include one or more of a patient monitoring unit 1312, 1322, a diagnostics unit 1314, 1324, and/or a therapy unit 1316, 1326.

The patient-external medical device 1320 performs monitoring, and/or diagnosis and/or therapy functions external to the patient (i.e., not invasively implanted within the patient's body). The patient-external medical device 1320 may be positioned on the patient, near the patient, or in any location external to the patient.

The patient-internal and patient-external medical devices 1310, 1320 may be coupled to one or more sensors 1341, 1342, 1345, 1346, patient input/trigger devices 1343, 1347 and/or other information acquisition devices 1344, 1348. The sensors 1341, 1342, 1345, 1346, patient input/trigger devices 1343, 1347, and/or other information acquisition devices 1344, 1348 may be employed to detect conditions relevant to the monitoring, diagnostic, and/or therapeutic functions of the patient-internal and patient-external medical devices 1310, 1320.

The medical devices 1310, 1320 may each be coupled to one or more patient-internal sensors 1341, 1345 that are fully or partially implantable within the patient. The medical devices 1310, 1320 may also be coupled to patient-external sensors positioned on, near, or in a remote location with respect to the patient. The patient-internal and patient-external sensors are used to sense conditions, such as physiological or environmental conditions, that affect the patient.

The patient-internal sensors 1341 may be coupled to the patient-internal medical device 1310 through one or more internal leads 1353. Still referring to FIG. 13, one or more patient-internal sensors 1341 may be equipped with transceiver circuitry to support wireless communications between the one or more patient-internal sensors 1341 and the patient-internal medical device 1310 and/or the patient-external medical device 1320. The patient-internal sensors 1345 may be coupled to the patient-external medical device 1320 through a wireless connection 1359, and/or using communications between the patient-internal medical device 1310 and the patient-external medical device 1320, or may be coupled using a wire or other communications channel.

The patient-external sensors 1342 may be coupled to the patient-internal medical device 1310 through one or more internal leads 1355. Patient-external sensors 1342 may communicate with the patient-internal medical device 1310 wirelessly. Patient-external sensors 1342 may be coupled to the patient-external medical device 1320 through one or more leads 1357 or through a wireless link.

In an embodiment of the present invention, the patient-external medical device 1320 includes a visual display configured to concurrently display non-electrophysiological signals and intracardiac electrogram signals. For example, the display may present the information visually. The patient-external medical device 1320 may also, or alternately, provide signals to other components of the medical system 1300 for presentation to a clinician, whether local to the patient or remote to the patient.

Referring still to FIG. 13, the medical devices 1310, 1320 may be connected to one or more information acquisition devices 1344, 1348, such as a database that stores information useful in connection with the monitoring, diagnostic, or therapy functions of the medical devices 1310, 1320. For example, one or more of the medical devices 1310, 1320 may be coupled through a network to a patient information server 1330.

The input/trigger devices 1343, 1347 are used to allow the physician, clinician, and/or patient to manually trigger and/or transfer information to the medical devices 1310, 1320 and/or from the APM system 1340 and/or patient-external medical device 1320 back to the patient-internal device 1310. The input/trigger devices 1343, 1347 may be particularly useful for inputting information concerning patient perceptions, such as a perceived cardiac event, how well the patient feels, and other information not automatically sensed or detected by the medical devices 1310, 1320. For example, the patient may trigger the input/trigger device 1343 upon perceiving a cardiac event. The trigger may then initiate the recording of cardiac signals and/or other sensor signals in the patient-internal device 1310. Later, a clinician may trigger the input/trigger device 1347, initiating the transfer of the recorded cardiac and/or other signals from the patient-internal device 1310 to the patient-external device 1320 for display and diagnosis.

In one embodiment, the patient-internal medical device 1310 and the patient-external medical device 1320 may communicate through a wireless link between the medical devices 1310, 1320. For example, the patient-internal and patient-external devices 1310, 1320 may be coupled through a short-range radio link, such as Bluetooth, IEEE 802.11, and/or a proprietary wireless protocol. The communications link may facilitate uni-directional or bi-directional communication between the patient-internal 1310 and patient-external 1320 medical devices. Data and/or control signals may be transmitted between the patient-internal 1310 and patient-external 1320 medical devices to coordinate the functions of the medical devices 1310, 1320.

In another embodiment, patient data may be downloaded from one or more of the medical devices periodically or on command, and stored at the patient information server 1330. The physician and/or the patient may communicate with the medical devices and the patient information server 1330, for example, to acquire patient data or to initiate, terminate or modify recording and/or therapy.

The data stored on the patient information server 1330 may be accessible by the patient and the patient's physician through one or more terminals 1350, e.g., remote computers located in the patient's home or the physician's office. The patient information server 1330 may be used to communicate to one or more of the patient-internal and patient-external medical devices 1310, 1320 to provide remote control of the monitoring, diagnosis, and/or therapy functions of the medical devices 1310, 1320.

In one embodiment, the patient's physician may access patient data transmitted from the medical devices 1310, 1320 to the patient information server 1330. After evaluation of the patient data, the patient's physician may communicate with one or more of the patient-internal or patient-external devices 1310, 1320 through an APM system 1340 to initiate, terminate, or modify the monitoring, diagnostic, and/or therapy functions of the patient-internal and/or patient-external medical systems 1310, 1320.

In another embodiment, the patient-internal and patient-external medical devices 1310, 1320 may not communicate directly, but may communicate indirectly through the APM system 1340. In this embodiment, the APM system 1340 may operate as an intermediary between two or more of the medical devices 1310, 1320. For example, data and/or control information may be transferred from one of the medical devices 1310, 1320 to the APM system 1340. The APM system 1340 may transfer the data and/or control information to another of the medical devices 1310, 1320.

In one embodiment, the APM system 1340 may communicate directly with the patient-internal and/or patient-external medical devices 1310, 1320. In another embodiment, the APM system 1340 may communicate with the patient-internal and/or patient-external medical devices 1310, 1320 through medical device programmers 1360, 1370 respectively associated with each medical device 1310, 1320. As was stated previously, the patient-internal medical device 1310 may take the form of an implantable PIMD.

In accordance with one approach of the present invention, a PIMD may be implemented to separate cardiac signals for selection and monitoring of vectors in a robust manner using a blind source separation technique. It is understood that all or certain aspects of the BSS technique described below may be implemented in a device or system (implantable or non-implantable) other than a PIMD, and that the description of BSS techniques implemented in a PIMD is provided for purposes of illustration, and not of limitation. For example, algorithms that implement a BSS technique as described below may be implemented for use by an implanted processor or a non-implanted processor, such as a processor of a programmer or computer of a patient-external device communicatively coupled to the PIMD.

Figure 14:
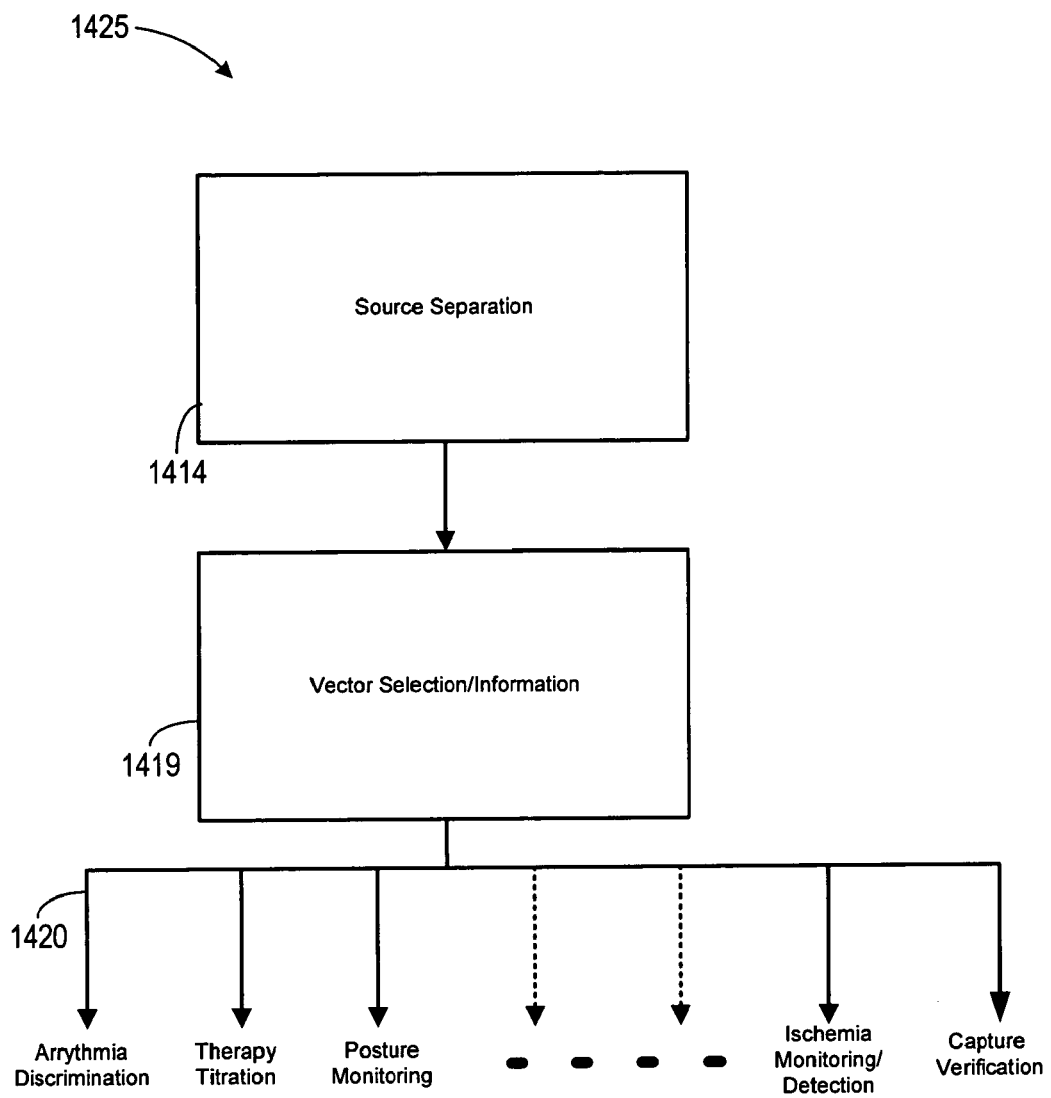
FIG. 14 is a block diagram illustrating uses of cardiac activation sequence monitoring and/or tracking in accordance with the present invention.
Figure 15:
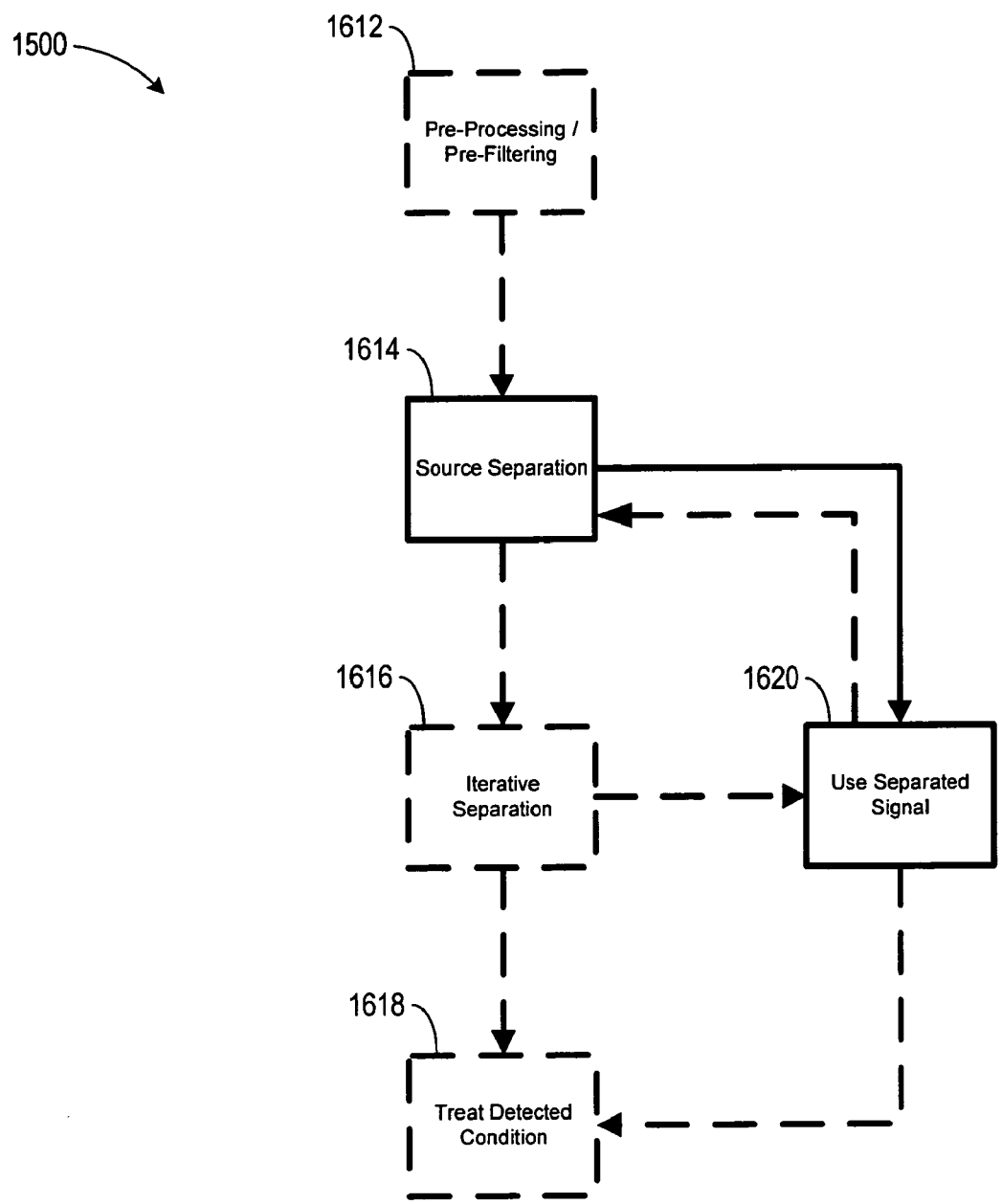
FIG. 15 is a block diagram of a signal separation process in accordance with the present invention.
Figure 16:
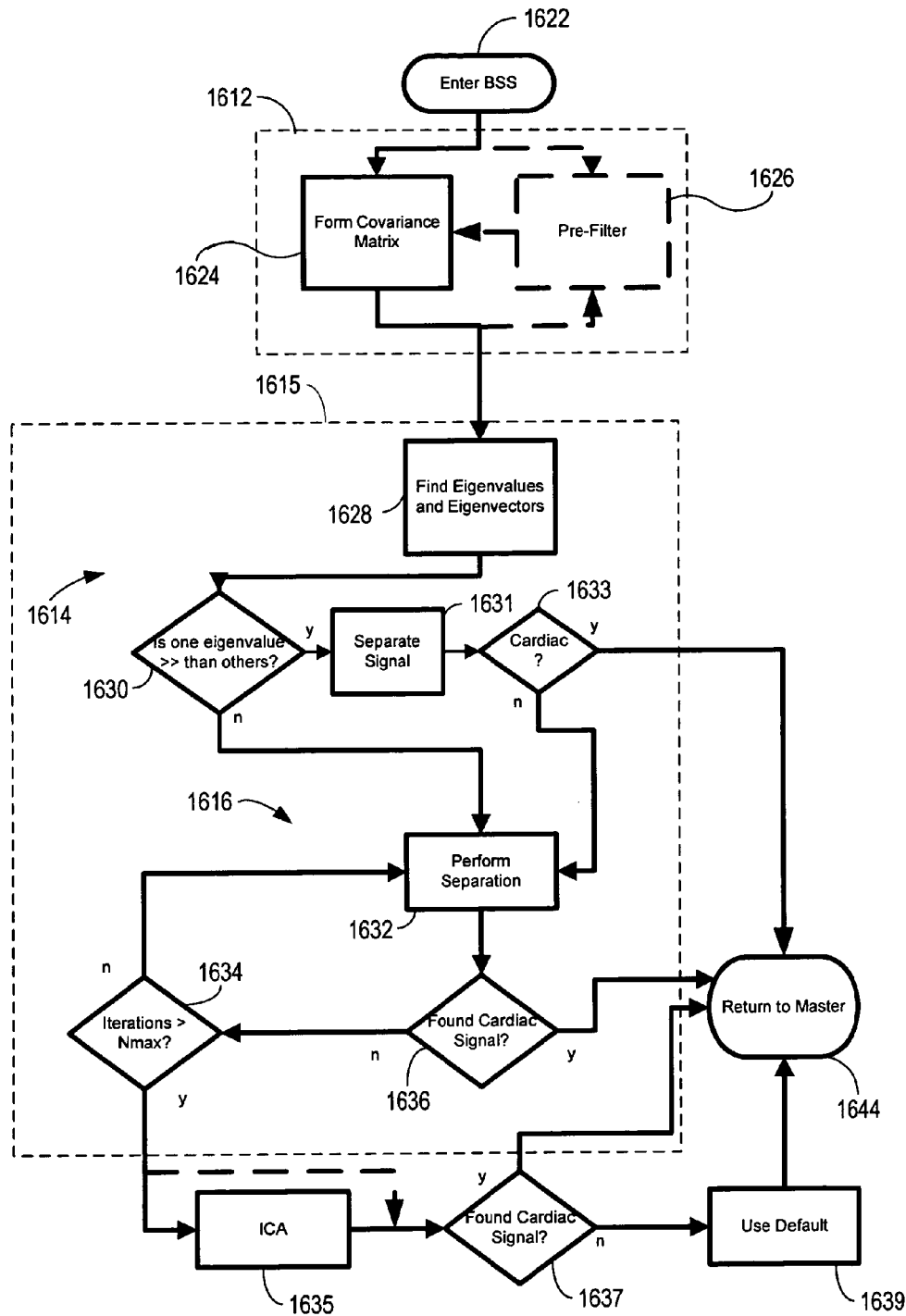
FIG. 16 is an expanded block diagram of the process illustrated in FIG. 15, illustrating an iterative independent component analysis in accordance with the present invention.

Referring now to FIGS. 14 through 16, cardiac monitoring and/or stimulation devices and methods employing cardiac signal separation are described in accordance with the present invention. The PIMD may be implemented to separate signal components according to their sources and produce one or more cardiac signal vectors associated with all or a portion of one or more cardiac activation sequences based on the source separation. To achieve this, the methods and algorithms illustrated in FIGS. 14 through 16 may be implemented.

FIG. 14 illustrates a portion of a cardiac activation sequence monitoring and/or tracking system 1425 in accordance with the present invention. A process 1414 is performed, providing a selected vector 1419 along with vector information including, for example, magnitude, angle, rates of change, trend information, and other statistics. The selected vector 1419 (and associated signal and other vector information) is available for a variety of uses 1420, such as, for example, arrhythmia discrimination, therapy titration, posture detection/monitoring, ischemia detection/monitoring, capture verification, disease diagnosis and/or progress information, or other use. In accordance with the present invention, the process may be used, and repeated, for arrhythmia discrimination, to monitor cardiac activation sequences, track changes in the progression of patient pathology, and to update sense vectors useful for cardiac sensing and/or stimulation, for example.

FIG. 15 illustrates an embodiment of a signal source separation/update process 1500 useful for cardiac activation sequence monitoring and/or tracking in accordance with the present invention. A set of composite signals, including at least two and up to n signals, are selected for separation, where n is an integer. Each electrode provides a composite signal associated with an unknown number of sources. Pre-processing and/or pre-filtering 1612 may be performed on each of the composite signals. It may be advantageous to filter each composite signal using the same filtering function. Source separation 1614 is performed, providing at least one separated signal. If a treatment is desired, an appropriate treatment or therapy 1618 is performed. If continued source separation is desired, the process returns to perform such source separation 1614 and may iteratively separate 1616 more signals until a desired signal is found, or all signals are separated.

The separated signal or signals may then be used 1620 for some specified purpose, such as, for example, to confirm a normal sinus rhythm, determine a cardiac condition, define a noise signal, monitor cardiac activation sequence, determine patient posture, diagnose or monitor a disease state, or other desired use. Electrode arrays and/or the use of multiple electrodes provide for many possible vectors useful for sensing cardiac activity.

Updating the vector to monitor and/or track changes may be performed periodically, on demand, at a predetermined time, upon the occurrence of a predetermined event, continuously, or as otherwise desired. For example, a PIMD may regularly perform an update of the sense vector used for cardiac discrimination, to keep performance of the PIMD improved and/or adjusted and/or optimized and/or to track or monitor progression of changes. Updating may be useful, for example, when pathology, therapy, posture, or other system or patient change suggests a change in vector may be detected and/or useful.

For example, in an APM environment such as described previously, a PIMD in accordance with the present invention may have a controller and communications circuitry that transmits its cardiac composite signals to a bedside signal processor when the patient is asleep. The signal processor may perform a blind source separation and analysis of the composite signals during the patient's sleep cycle. The signal processor may then determine the appropriate vector or vectors for the PIMD, and reprogram the PIMD before the patient awakes. The PIMD may then operate with the latest programming until the next update.

FIG. 16 illustrates further embodiments of a signal source separation process in greater detail, including some optional elements. Entry of the process at block 1622 provides access to a pre-processing facility 1612, illustrated here as including a covariance matrix computation block 1624 and/or a pre-filtering block 1626 such as, for example, a band-pass filtering block. The composite signals processed at pre-processing block 1612 are provided to a signal source separation block 1615, which may include functionality of the source separation block 1614 and iterative source separation block 1616 shown in FIG. 15.

The signal source separation block 1615 includes a principal component analysis block 1628, which produces an associated set of eigenvectors and eigenvalues using a covariance matrix or composite signals provided by pre-processing block 1612. A determination 1630 is made as to whether one eigenvalue is significantly larger than any others in the set, making the dimension associated with this eigenvalue a likely candidate for association with the direction along which the power of the signal is maximized. If such a candidate is identified at block 1630, the candidate signal may immediately be separated 1631 and a determination 1633 made to confirm whether the candidate signal is a cardiac signal, before returning 1644 to the master PIMD routine that called the signal source separation process.

If there is no clear candidate eigenvalue, or if the largest value eigenvalue did not provide a signal of interest, an iterative process may be used to separate 1632 and search 1636 for the signal of interest (e.g., cardiac signal). This process 1632, 1636, 1634 may be repeated until such a signal is found, or no more signals are separable 1634 as determined by exceeding a predefined number of iterations $N_{max}$ or some other termination criterion. An example of such a criterion is an eigenvalue considered at the current iteration being proportionately smaller than the largest eigenvalues by some predetermined amount.

If the iterations 1634 are completed and a cardiac signal is not found at 1636, then an Independent component analysis 1635 may be attempted to further process the signals in an attempt to find the cardiac signal. If a cardiac signal is still not found at decision 1637, after exhausting all possibilities, then a set of default settings 1639 may be used, or an error routine may be initiated.

In another embodiment of the present invention, a method of signal separation involves sensing, at least in part implantably, two or more composite signals using three or more cardiac electrodes or electrode array elements. The method may further involve performing a source separation using the detected composite signals, the source separation producing two or more vectors. A first vector and a second vector may be selected from the set of vectors.

The use of the terms first and second vector are not intended to imply that the vectors are the first and second vectors separated from the composite signal, but that a first vector and a second vector are selected from among any vectors available for a given composite signal. First and second signals may be identified from the detected two or more composite signals using the first and second vectors respectively. The method then involves selecting either the first vector or the second vector as a selected vector based on a selection criterion.

Selection criteria may include finding the optimum vector for cardiac signal identification, finding a vector that provides the largest magnitude cardiac signal, or finding another particular signal of interest. For example, the first vector may be selected and used for cardiac activity monitoring, and the second vector may then be selected and used for skeletal muscle activity monitoring. The skeletal muscle signal may then be used to further discriminate arrhythmias from noise such as is further described in commonly owned U.S. Pat. No. 7,117,035, which is hereby incorporated herein by reference.

With continued reference to FIGS. 14 through 16, one illustrative signal source separation methodology useful with the present invention is described below. Such an approach is particularly well suited for use in a PIMD system. It is to be understood that the example provided below is provided for non-limiting, illustrative purposes only. Moreover, it is understood that signal source separation within the context of the present invention need not be implemented using the specific processes described below, or each and every process described below.

A collected signal may be pre-filtered to suppress broadly incoherent noise and to generally optimize the signal-to-noise ratio (SNR). Any noise suppression in this step has the additional benefit of reducing the effective number of source signals that need to be separated. A Principal Component Analysis (PCA) may be performed on the collected and/or pre-filtered signal, producing a set of eigenvectors and associated eigenvalues describing the optimal linear combination, in a least-squares sense, of the recorded signals that makes the components coming from different sources orthogonal to one another. As an intermediate step to performing the PCA, an estimate of the spatial covariance matrix may be computed and averaged over a relatively short time interval (on the order of 2-3 beats), or over the windowed signal as described previously, to enhance those components that are mutually correlated.

Each eigenvalue corresponds to the power of the signal projected along the direction of each associated eigenvector. The cardiac signal component is typically identified by one of the largest eigenvalues. Occasionally, PCA does not achieve a substantially sufficient level of source independence. In such a case, an Independent Component Analysis (ICA) may be performed to determine the actual source direction, either upon the PCA-transformed signal, or directly upon the collected signal. The ICA consists of a unitary transformation based on higher-order statistical analysis.

For example, separation of two mixed sources may be achieved by rotating the complex variable formed from the signals on an angle that aligns their probability distributions with basis vectors. In another approach, an algorithm based on minimization of mutual information between components, as well as other approaches generally known in the field of ICA, may be used to achieve reconstructed source independence.

A PIMD may, for example, employ a hierarchical decision-making procedure that initiates a blind source separation algorithm upon the detection of a condition under which the target vector may change. By way of example, a local peak density algorithm or a curvature-based significant point methodology may be used as a high-level detection routine. Other sensors/information available to the PIMD may also trigger the initiation of a blind source separation algorithm.

The PIMD may compute an estimate of the covariance matrix. It may be sufficient to compute the covariance matrix for only a short time. Computation of the eigenvalues and eigenvectors required for the PCA may also be performed adaptively through an efficient updating algorithm.

The cardiac signal may be identified among the few (e.g., two or three) largest separated signals. One of several known algorithms may be used. For example, local peak density (LPD) or beat detection (BD) algorithms may be used. The LPD algorithm may be used to identify the cardiac signal by finding a signal that has an acceptable physiologic range of local peak densities by comparing the LPD to a predetermined range of peak densities known to be acceptable. The BD algorithm finds a signal that has a physiologic range of beat rate. In the case where two signals look similar, a morphology algorithm may be used for further discrimination. It may be beneficial to use the same algorithm at different levels of hierarchy: 1) initiation of blind source separation algorithm; 2) iterative identification of a cardiac signal.

Mathematical development of an example of blind source separation algorithm in accordance with the present invention is provided as follows. Assume there are m source signals $s_1(t), \ldots, s_m(t)$ that are detected inside of the body, including a desired cardiac signal and some other independent noise, which may, for example, include myopotential noise, electrocautery response, etc. These signals are recorded simultaneously from k sensing vectors derived from subcutaneous sensing electrodes, where all m signals may be resolved if k>m. By definition, the signals are mixed together into the overall voltage gradient sensed across the electrode array. In addition, there is usually an additive noise attributable, for example, to environmental noise sources. The relationship between the source signals s(t) and recorded signals x(t) is described below:

$$\begin{pmatrix} x_1(t) \\ x_2(t) \\ M \\ x_k(t) \end{pmatrix} = \begin{pmatrix} y_1(t) \\ y_2(t) \\ M \\ y_k(t) \end{pmatrix} + \begin{pmatrix} n_1(t) \\ n_2(t) \\ M \\ n_k(t) \end{pmatrix}$$

-continued $$= \begin{pmatrix} a_{11} & a_{12} & \ldots & a_{1m} \\ a_{21} & a_{22} & \ldots & a_{2m} \\ M & M & O & M \\ a_{k1} & a_{k2} & \ldots & a_{km} \end{pmatrix} \begin{pmatrix} s_1(t) \\ s_2(t) \\ M \\ s_k(t) \end{pmatrix} + \begin{pmatrix} n_1(t) \\ n_2(t) \\ M \\ n_k(t) \end{pmatrix}$$

$$= x(t) = y(t) + n(t) = As(t) + n(t), \quad m < k$$

Here, x(t) is an instantaneous linear mixture of the source signals and additive noise, y(t) is the same linear mixture without the additive noise, n(t) is environmental noise modeled as Gaussian noise, A is an unknown mixing matrix, and s(t) are the unknown source signals considered here to include the desired cardiac signal and other biological artifacts. There is no assumption made about the underlying structure of the mixing matrix and the source signals, except for their spatial statistical independence. The objective is to reconstruct the source signals s(t) from the recorded signals x(t).

Reconstruction of the source signals s(t) from the recorded signals x(t) may involve pre-filtering x(t) to optimize the SNR (i.e., maximize the power of s(t) against that of n(t)). Here, a linear phase filter may be used to minimize time-domain dispersion (tails and ringing) and best preserve the underlying cardiac signal morphology. It is noted that the notation x(t) is substituted for the pre-filtered version of x(t).

An estimate of the spatial covariance matrix R is formed as shown immediately below. This step serves to enhance the components of the signal that are mutually correlated and downplays incoherent noise.

$$R = \frac{1}{T_{(\sim 1 sec)}} \sum_{t=1,T} \begin{pmatrix} x_1(t) \\ x_2(t) \\ \ldots \\ x_k(t) \end{pmatrix} * (x_1(t) \; x_2(t) \; \ldots \; x_k(t))$$

$$= \frac{1}{T_{(\sim 1 sec)}} \sum_{t=1,T} \begin{bmatrix} x_1(t)*x_1(t) & x_1(t)*x_2(t) & \ldots & x_1(t)*x_k(t) \\ x_2(t)*x_1(t) & x_2(t)*x_2(t) & \ldots & x_2(t)*x_k(t) \\ \ldots & \ldots & O & \ldots \\ x_k(t)*x_1(t) & x_k(t)*x_2(t) & \ldots & x_k(t)*x_k(t) \end{bmatrix}$$

Eigenvalues and eigenvectors of the covariance matrix R may be determined using singular value decomposition (SVD). By definition, the SVD factors R as a product of three matrices $R=USV^T$, where U and V are orthogonal matrices describing amplitude preserving rotations, and S is a diagonal matrix that has the squared eigenvalues $\sigma_1 \ldots \sigma_k$ on the diagonal in monotonically decreasing order. Expanded into elements, this SVD may be expressed as follows.

$$R = \begin{pmatrix} u_{11} & u_{12} & \ldots & u_{1k} \\ u_{21} & u_{22} & \ldots & u_{2k} \\ M & M & O & M \\ u_{k1} & u_{k2} & \ldots & u_{kk} \end{pmatrix} \begin{pmatrix} \sigma_1 & 0 & 0 & 0 \\ 0 & \sigma_2 & 0 & 0 \\ M & M & O & M \\ 0 & 0 & K & \sigma_k \end{pmatrix} \begin{pmatrix} v_{11} & v_{12} & \ldots & v_{1k} \\ v_{21} & v_{22} & \ldots & v_{2k} \\ M & M & O & M \\ v_{k1} & v_{k2} & \ldots & v_{kk} \end{pmatrix}$$

The columns of matrix V consist of eigenvectors that span a new coordinate system wherein the components coming from different sources are orthogonal to one another. Eigenvalues $\sigma_1 \ldots \sigma_k$ correspond respectively to columns $1 \ldots k$ of V. Each eigenvalue defines the signal "power" along the direction of its corresponding eigenvector. The matrix V thus provides a rotational transformation of x(t) into a space where each separate component of x is optimally aligned, in a least-squares sense, with a basis vector of that space.

The largest eigenvalues correspond to the highest power components, which typically represent the mixed source signals $y_1(t), \ldots, y_m(t)$. The lower eigenvalues typically are associated with additive noise $n_1(t), \ldots, n_{k-m}(t)$. Each eigenvector may then be viewed as an optimal linear operator on x that maximizes the power of the corresponding independent signal component. As a result, the transformed signal is found as:

$$\hat{y}(t) = \begin{pmatrix} \hat{y}_1(t) \\ M \\ \hat{y}_m(t) \end{pmatrix} = \begin{pmatrix} v_{11} & v_{21} & K & v_{k1} \\ M & M & O & M \\ v_{1m} & v_{2m} & \ldots & v_{km} \end{pmatrix} * \begin{pmatrix} x_1(t) \\ x_2(t) \\ M \\ x_k(t) \end{pmatrix}$$

The component estimates $\hat{y}_1(t), \ldots, \hat{y}_m(t)$ of $y_1(t), \ldots, y_m(t)$ are aligned with the new orthogonal system of coordinates defined by eigenvectors. As a result, they should be orthogonal to each other and thus independent.

In an alternative implementation, eigenvalues and eigenvectors of the covariance matrix R may be determined using eigenvalue decomposition (ED). By definition, the ED solves the matrix equation RV=SV so that S is a diagonal matrix having the eigenvalues $\sigma_1 \ldots \sigma_k$ on the diagonal, in monotonically decreasing order, and so that matrix V contains the corresponding eigenvectors along its columns. The resulting eigenvalues and associated eigenvectors may be applied in similar manner to those resulting from the SVD of covariance matrix R.

In an alternative implementation, eigenvalues and eigenvectors are computed directly from x(t) by forming a rectangular matrix X of k sensor signals collected during a time segment of interest, and performing an SVD directly upon X. The matrix X and its decomposition may be expressed as follows.

$$X = \begin{pmatrix} x_1(t) \\ x_2(t) \\ M \\ x_k(t) \end{pmatrix} = \begin{pmatrix} x_1(t_1) & x_1(t_2) & K & x_1(t_T) \\ x_2(t_1) & x_2(t_2) & \Lambda & x_2(t_T) \\ M & M & O & M \\ x_k(t_1) & x_k(t_2) & \Lambda & x_k(t_T) \end{pmatrix} = USV^T$$

Note that in cases where T>k, a so-called "economy-size" SVD may be used to find the eigenvalues and eigenvectors efficiently. Such an SVD may be expressed as follows, expanded into elements.

$$X = USV^T$$

$$= \begin{pmatrix} u_{11} & u_{12} & \ldots & u_{1T} \\ u_{21} & u_{22} & \ldots & u_{2T} \\ M & M & O & M \\ u_{k1} & u_{k2} & \ldots & u_{kT} \end{pmatrix} \begin{pmatrix} \sigma_1 & 0 & K & 0 \\ 0 & \sigma_2 & K & 0 \\ M & M & O & M \\ 0 & 0 & K & \sigma_k \end{pmatrix} \begin{pmatrix} v_{11} & v_{12} & \ldots & v_{1k} \\ v_{21} & v_{22} & \ldots & v_{2k} \\ M & M & O & M \\ v_{k1} & v_{k2} & \ldots & v_{kk} \end{pmatrix}$$

A similar economy-sized SVD may also be used for the less typical case where k>T. The matrices S and V resulting from performing the SVD of data matrix X may be applied in the context of this present invention identically as the matrices S and V resulting from performing the SVD on the covariance matrix R.

At this point, the mutual separation of $\hat{y}_1(t), \ldots, \hat{y}_m(t)$ would be completed, based on the covariance statistics. Occasionally, information from covariance is not sufficient to achieve source independence. This happens, for example, when the cardiac signal is corrupted with electrocautery, which may cause perturbations from the linearly additive noise model. In such a case, Independent Component Analysis (ICA) may be used to further separate the signals.

The ICA seeks to find a linear transformation matrix W that inverts the mixing matrix A in such manner as to recover an estimate of the source signals. The operation may be described as follows.

$$s(t) = \begin{pmatrix} s_1(t) \\ s_2(t) \\ M \\ s_m(t) \end{pmatrix} = Wy(t) \approx A^{-1}y(t)$$

Here we substitute s(t) for the recovered estimate of the source signals. The signal vector y(t) corresponds to either the collected sensor signal vector x(t) or to the signal ŷ(t) separated with PCA. The matrix W is the solution of an optimization problem that maximizes the independence between the components $s_1(t), \ldots, s_m(t)$ of s(t)=Wy(t). We treat the components of s(t) as a vector of random variables embodied in the vector notation s, so that the desired transformation would optimize some cost function $C(s)=C([s_1(t), \ldots, s_m(t)])$ that measures the mutual independence of these components. Given the joint probability density function (pdf) $f(s)$ and the factorized pdf $\bar{f}(s)=f_1(s_1) f_2(s_2) \ldots f_m(s_m)$, or given estimates of these pdf's, we may solve the following.

$$\min_W C(s) = \min_W \int D(f(s), \bar{f}(s)) ds$$

The function $D(f(s),\bar{f}(s))$ may be understood as a standard distance measure generally known in the art, such as for example an absolute value difference $|f(s)-\bar{f}(s)|$, Euclidean distance $(f(s)-\bar{f}(s))^2$, or p-norm $(f(s)-\bar{f}(s))^p$. The distance measure approaches zero as $f(s)$ approaches $\bar{f}(s)$, which by the definition of statistical independence, occurs as the components of s approach mutual statistical independence.

In an alternative implementation, the distance measure may take the form of a Kullback-Liebler divergence (KLD) between $f(s)$ and $\bar{f}(s)$, yielding cost function optimizations in either of the following forms.

$$\min_W C(s) = \min_W \int f(s) \log \frac{f(s)}{\bar{f}(s)} ds \text{ or}$$
$$= \min_W \int \bar{f}(s) \log \frac{\bar{f}(s)}{f(s)} ds$$

Since the KLD is not symmetric, the two alternative measures are related but not precisely equal. One measure could be chosen, for example, if a particular underlying data distribution favors convergence with that measure.

Several alternative approaches may be used to measure the mutual independence of the components of s. These may include the maximum likelihood method, maximization of negentropy or its approximation, and minimization of mutual information.

In the maximum likelihood method, the desired matrix W is found as a solution of the following optimization problem, $$\max_W \sum_{j=1}^T \sum_{i=1}^m \log f_i(s_i(t_j)) + T\log|\det W| =$$
$$\max_W \sum_{j=1}^T \sum_{i=1}^m \log f_i(w_i^T y(t_j)) + T\log|\det W|$$

where $w_i$ are columns of the matrix W. In the negentropy method, the cost function is defined in terms of differences in entropy between s and a corresponding Gaussian random variable, resulting in the following optimization problem, $$\max_W \{H(s_{gauss}) - H(s)\} =$$
$$\max_W \left\{ -\int f(s_{gauss}) \log f(s_{gauss}) ds_{gauss} + \int f(s) \log(s) ds \right\}$$

where H(s) is the entropy of random vector s, and $s_{gauss}$ is a Gaussian random vector chosen to have a covariance matrix substantially the same as that of s.

In the minimization of mutual information method, the cost function is defined in terms of the difference between the entropy of s and the sum of the individual entropies of the components of s, resulting in the following optimization problem $$\min_W \left\{ -\sum_{i=1}^m \int f(s_i) \log f(s_i) ds_i + \int f(s) \log f(s) ds \right\}$$

All preceding cost function optimizations having an integral form may be implemented using summations by approximating the underlying pdf's with discrete pdf's, for example as the result of estimating the pdf using well-known histogram methods. We note that knowledge of the pdf, or even an estimate of the pdf, may be difficult to implement in practice due either to computational complexity, sparseness of available data, or both. These difficulties may be addressed using cost function optimization methods based upon kurtosis, a statistical parameter that does not require a pdf.

In an alternative method a measure of independence could be expressed via kurtosis, equivalent to the fourth-order statistic defined as the following for the $i^{th}$ component of s $$\text{kurt}(s_i) = E\{s_i^4\} - 3(E\{s_i^2\})^2$$

In this case W is found as a matrix that maximizes kurtosis of s=Wy over all the components of s (understanding y to be a vector of random variables corresponding to the components of y(t)). In all the previous examples of ICA optimization the solution W could be found via numerical methods such as steepest descent, Newton iteration, etc., well known and established in the art. These methods could prove numerically intensive to implement in practice, particularly if many estimates of statistics in s must be computed for every iteration in W.

Computational complexity may be addressed several ways. To begin, the ICA could be performed on the PCA-separated signal ŷ(t) with the dimensionality reduced to only the first few (or in the simplest case, two) principal components. For situations where two principal components are not sufficient to separate the sources, the ICA could still be performed pairwise on two components at a time, substituting component pairs at each iteration of W (or group of iterations of W).

In one example, a simplified two-dimensional ICA may be performed on the PCA separated signals. In this case, a unitary transformation could be found as a Givens rotation matrix with rotation angle $\theta$, $$W(\theta) = \begin{pmatrix} \cos\theta & \sin\theta \\ -\sin\theta & \cos\theta \end{pmatrix}$$

where $s(t)=W(\theta)y(t)$. Here $W(\theta)$ maximizes the probability distribution of each component along the basis vectors, such that the following is satisfied.

$$\theta = \underset{\theta}{\operatorname{argmax}} \sum_{t=1}^{T} \log f(s(t)\mid\theta)$$

This optimal rotation angle may be found by representing vectors y(t) and s(t) as complex variables in the polar coordinate form $$\xi = e^{i4\theta}E(\rho^4 e^{i4\phi'}) = e^{i4\theta}E[(s_1+is_2)^4] = e^{i4\theta}(\kappa_{40}{}^s + \kappa_{04}{}^s)$$

$$y = y_1+iy_2 = \rho e^{i\phi}, s = s_1+is_2 = \rho e^{i\phi'}$$

and finding the relationships between their angles $\phi,\phi'$: $\phi=\phi'+\theta$, where $\theta$ is the rotation that relates the vectors. Then, the angle $\theta$ may be found from the fourth order-statistic of a complex variable $\xi$, where $\kappa^s$ is kurtosis of the signal s(t).

By definition, source kurtosis is unknown, but may be found based on the fact that the amplitude of the source signal and mixed signals are the same.

As a result, $4\theta = \hat{\xi} \operatorname{sign}(\hat{\gamma})$ with $\gamma = E[\rho^4]-8 = \kappa_{40}{}^s = \kappa_{04}{}^s$ and $\rho^2 = s_1{}^2+s_2{}^2 = y_1{}^2+y_2{}^2$ In summary, the rotation angle may be estimated as:

$$\theta = \frac{1}{4}\operatorname{angle}(\hat{\xi}\operatorname{sign}(\hat{\gamma}))$$

where $$\hat{\xi} = \frac{1}{T}\sum_{t=1,T} \rho_t^4 e^{i4\varphi(t)} = \frac{1}{T}\sum_{t=1,T}(y_1(t)+iy_2(t))^4,$$

$$\hat{\gamma} = \frac{1}{T}\sum_{t=1,T}\rho_t^4 - 8 = \frac{1}{T}\sum_{t=1,T}(y_1^2(t)+iy_2^2(t))^4 - 8$$

After the pre-processing step, the cardiac signal is normally the first or second most powerful signal. In addition, there is usually in practice only one source signal that is temporally white. In this case, rotation of the two-dimensional vector $y=y_1+iy_2=\rho e^{i\phi}$ is all that is required. In the event that more than two signals need to be separated, the Independent Component Analysis process may be repeated in pairwise fashion over the $m(m-1)/2$ signal pairs until convergence is reached, usually taking about $(1+\sqrt{m})$ iterations.

A PIMD that implements the above-described processes may robustly separate the cardiac signal from a low SNR signal recorded from the implantable device. Such a PIMD robustly separates cardiac signals from noise to allow for improved sensing of cardiac rhythms and arrhythmias.

The system operates by finding a combination of the spatially collected low SNR signals that makes cardiac signal and noise orthogonal to each other (independent). This combination achieves relatively clean extraction of the cardiac signal even from negative SNR conditions.

A PIMD may operate in a batch mode or adaptively, allowing for on-line or off-line implementation. To save power, the system may include the option for a hierarchical decision-making routine that uses algorithms known in the art for identifying presence of arrhythmias or noise in the collected signal and initiating the methods of the present invention.

Various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. A processor-implemented method, comprising:
   sensing a plurality of composite cardiac signals at a plurality of patient-internal locations for a multiplicity of cardiac cycles;
   performing a plurality of source separations using the sensed composite cardiac signals;
   producing a cardiac signal vector indicative of a cardiac activation sequence of an area of the patient's heart based on each of the plurality of source separations;
   measuring an orientation of the cardiac signal vectors relative to a baseline established for the patient;
   detecting ventricular tachycardia (VT) based on the cardiac signal vector orientation measurements; and
   in response to detecting VT:
     determining variation of the cardiac signal vector orientation measurements, wherein determining the variation of the cardiac signal vector orientation measurements comprises:
       performing a subsequent source separation using sensed composite cardiac signals for each of a plurality of consecutive cardiac cycles after VT is detected;
       producing a subsequent cardiac signal vector based on each of the subsequent source separations;
       measuring an orientation of each subsequent cardiac signal vector relative to the baseline; and
       determining the variation of the subsequent cardiac signal vector orientation measurements; and
     discriminating between polymorphic ventricular tachycardia (PVT) and monomorphic ventricular tachycardia (MVT) based on the variation of the cardiac signal vector orientation measurements, wherein at least some of the method is implemented by a processor.

2. The method according to claim 1, wherein determining the variation comprises determining the variation of cardiac signal vector orientation measurements for a plurality of consecutive cardiac cycles subsequent to VT detection.

3. The method according to claim 1, wherein discriminating between PVT and MVT comprises:
   comparing the variation to a pre-determined value; and
   discriminating between PVT and MVT based on the comparison.

4. The method according to claim 1, wherein discriminating between PVT and MVT comprises:
   comparing the variation to a pre-determined value;
   determining presence of PVT if the variation is greater than the pre-determined value; and determining presence of MVT if the variation is less than the pre-determined value.

5. The method according to claim 1, comprising establishing the baseline by performing an initial source separation using sensed composite cardiac signals.

6. The method according to claim 1, comprising establishing the baseline using clinical data.

7. The method according to claim 1, further comprising differentiating between left ventricular tachycardia (LVT) and right ventricular tachycardia (RVT) in response to detecting MVT.

8. The method according to claim 7, comprising:
determining a shift in orientation of axes of the cardiac signal vectors relative to the baseline; and
differentiating between LVT and RVT based on a direction of the shift of the cardiac signal vector axes.

9. The method according to claim 7, comprising:
determining a directional shift of cardiac signal vector axes relative to the baseline;
determining whether the directional shift of the cardiac signal vector axes falls within a pre-determined LVT range or a pre-determined RVT range;
identifying the VT as LVT in response to the directional shift falling within the LVT range; and
identifying the VT as RVT in response to the directional shift falling within the RVT range.

10. An apparatus, comprising:
a plurality of implantable electrodes configured for sensing composite cardiac signals over a multiplicity of cardiac cycles;
a housing configured for implantation in a patient; and
a processor provided in the housing and coupled to the plurality of implantable electrodes, the processor configured to perform a plurality of source separations using the sensed composite cardiac signals, produce a cardiac signal vector indicative of a cardiac activation sequence of an area of the patient's heart based on each of the plurality of source separations, measure an orientation of the cardiac signal vectors relative to a baseline established for the patient, detect ventricular tachycardia (VT) based on the cardiac signal vector orientation measurements, and, if VT is detected, discriminate between polymorphic ventricular tachycardia (PVT) and monomorphic ventricular tachycardia (MVT) based on the cardiac signal vector orientation measurements;
wherein the processor is configured to perform a subsequent source separation using sensed composite cardiac signals for each of a plurality of consecutive cardiac cycles after VT is detected, produce a subsequent cardiac signal vector based on each of the subsequent source separations, measure an orientation of each subsequent cardiac signal vector relative to the baseline, and determine the variation of the subsequent cardiac signal vector orientation measurements.

11. The apparatus according to claim 10, wherein the processor is configured to determine the variation of cardiac signal vector orientation measurements for a plurality of consecutive cardiac cycles subsequent to VT detection.

12. The apparatus according to claim 10, wherein the processor is configured to compare the variation to a pre-determined value, and discriminate between PVT and MVT based on the comparison.

13. The apparatus according to claim 10, wherein the processor is configured to compare the variation to a pre-determined value, determine presence of PVT if the variation is greater than the pre-determined value, and determine presence of MVT if the variation is less than the pre-determined value.

14. The apparatus according to claim 10, wherein the processor is configured to establish the baseline by performing an initial source separation using sensed composite cardiac signals.

15. The apparatus according to claim 10, wherein the processor is configured to use a baseline based on clinical data.

16. The apparatus according to claim 10, wherein the processor is configured to differentiate between left ventricular tachycardia (LVT) and right ventricular tachycardia (RVT) in response to detecting MVT.

17. The apparatus according to claim 16, wherein the processor is configured to determine a shift in orientation of axes of the cardiac signal vectors relative to the baseline, and differentiate between LVT and RVT based on a direction of the shift of the cardiac signal vector axes.

18. The apparatus according to claim 16, wherein the processor is configured to determine a directional shift of cardiac signal vector axes relative to the baseline, determine whether the directional shift of the cardiac signal vector axes falls within a pre-determined LVT range or a pre-determined RVT range, identify the VT as LVT in response to the directional shift falling within the LVT range, and identify the VT as RVT in response to the directional shift falling within the RVT range.

* * * * *